US012035969B2

(12) United States Patent
Goodrich et al.

(10) Patent No.: US 12,035,969 B2
(45) Date of Patent: Jul. 16, 2024

(54) DEVICES AND SYSTEMS FOR ABLATION THERAPY

(71) Applicant: Nanospectra Biosciences, Inc., Houston, TX (US)

(72) Inventors: Glenn Patrick Goodrich, Bellaire, TX (US); Jon Alexander Schwartz, Sugar Land, TX (US); Andrew Mark Murphy, Campbell, CA (US)

(73) Assignee: NANOSPECTRA BIOSCIENCES, INC., Houston, TX (US)

( * ) Notice: Subject to any disclaimer, the term of this patent is extended or adjusted under 35 U.S.C. 154(b) by 755 days.

(21) Appl. No.: 17/217,905

(22) Filed: Mar. 30, 2021

(65) Prior Publication Data
US 2021/0307829 A1    Oct. 7, 2021

Related U.S. Application Data

(63) Continuation of application No. 16/746,765, filed on Jan. 17, 2020, now Pat. No. 10,993,769, which is a
(Continued)

(51) Int. Cl.
*A61B 18/28* (2006.01)
*A61B 17/34* (2006.01)
(Continued)

(52) U.S. Cl.
CPC .......... *A61B 18/28* (2013.01); *A61B 17/3415* (2013.01); *A61B 18/22* (2013.01);
(Continued)

(58) Field of Classification Search
CPC ..... A61B 18/28; A61B 17/3415; A61B 18/22; A61B 18/24; A61B 18/04;
(Continued)

(56) References Cited

U.S. PATENT DOCUMENTS 4,832,024 A    5/1989   Boussignac et al.
5,267,995 A   12/1993   Doiron et al.
(Continued)

FOREIGN PATENT DOCUMENTS

CN    105682589 A    6/2016
CN    110290757      9/2019
(Continued)

OTHER PUBLICATIONS

U.S. Appl. No. 16/746,765, filed Jan. 17, 2020, Devices and Systems for Ablation Therapy, Issued May 4, 2021.
(Continued)

*Primary Examiner* — Linda C Dvorak
*Assistant Examiner* — Kyle M. Brown
(74) *Attorney, Agent, or Firm* — Knobbe, Martens, Olson & Bear LLP

(57) ABSTRACT

Various methods, systems, and devices for treating tissue ablation are disclosed. Some embodiments disclosed herein pertain to methods of treating tumors, systems used for irradiating tissue and tumors with electromagnetic radiation, components and devices of that system, and kits for providing systems used for irradiating tissue and tumors with electromagnetic radiation. In some embodiments, the system provides sub-ablative infrared radiation that is absorbed by nanoparticles. In some embodiments, the nanoparticles absorb the radiation converting it into heat energy. In some embodiments, though the infrared radiation itself may be sub-ablative, the heat energy generated by the nanoparticles is sufficient to cause thermal coagulation, hyperthermia, and/or tissue ablation.

20 Claims, 30 Drawing Sheets

Related U.S. Application Data continuation of application No. 16/327,292, filed as application No. PCT/US2017/066522 on Dec. 14, 2017, now Pat. No. 10,568,693.

(60) Provisional application No. 62/435,431, filed on Dec. 16, 2016.

(51) Int. Cl.
| | |
|---|---|
| *A61B 18/22* | (2006.01) |
| *A61B 18/24* | (2006.01) |
| *A61K 9/00* | (2006.01) |
| *A61K 9/51* | (2006.01) |
| *A61K 41/00* | (2020.01) |
| *A61M 25/06* | (2006.01) |
| *A61N 5/06* | (2006.01) |
| *A61B 18/00* | (2006.01) |
| *A61B 18/04* | (2006.01) |
| *A61B 18/20* | (2006.01) |
| *A61N 5/067* | (2006.01) |

(52) U.S. Cl.
CPC .......... *A61B 18/24* (2013.01); *A61K 9/0009* (2013.01); *A61K 9/0019* (2013.01); *A61K 9/5115* (2013.01); *A61K 41/0028* (2013.01); *A61K 41/0052* (2013.01); *A61M 25/0662* (2013.01); *A61N 5/0603* (2013.01); *A61N 5/062* (2013.01); *A61B 2018/00011* (2013.01); *A61B 2018/00023* (2013.01); *A61B 2018/00547* (2013.01); *A61B 2018/00577* (2013.01); *A61B 2018/00589* (2013.01); *A61B 18/04* (2013.01); *A61B 2018/2005* (2013.01); *A61B 2018/2205* (2013.01); *A61B 2018/2261* (2013.01); *A61N 5/0625* (2013.01); *A61N 2005/063* (2013.01); *A61N 2005/0659* (2013.01); *A61N 5/067* (2021.08)

(58) Field of Classification Search
CPC .......... A61B 2018/00011; A61B 2018/00023; A61B 2018/00547; A61B 2018/00577; A61B 2018/00589; A61B 2018/00821; A61B 2018/2005; A61B 2018/2205; A61B 2018/2261; A61B 2017/00973; A61B 2018/2253; A61K 9/0009; A61K 9/0019; A61K 9/5115; A61K 41/0028; A61K 41/0052; A61M 25/0662; A61N 5/0603; A61N 5/062; A61N 5/0625; A61N 5/067; A61N 2005/063; A61N 2005/0659; A61N 5/0601; A61N 2005/0612; A61N 1/406; A61P 35/00

See application file for complete search history.

(56) References Cited

U.S. PATENT DOCUMENTS

| | | |
|---|---|---|
| 5,606,975 A | 3/1997 | Liang et al. |
| 5,647,871 A | 7/1997 | Levine |
| 5,782,825 A | 7/1998 | Anderson |
| 5,797,901 A | 8/1998 | Cosmescu |
| 6,039,728 A | 3/2000 | Berlien et al. |
| 6,165,440 A | 12/2000 | Esenaliev |
| 6,283,958 B1 | 9/2001 | Vogl et al. |
| 6,344,272 B1 | 2/2002 | Oldenburg et al. |
| 6,428,811 B1 | 8/2002 | West et al. |
| 6,477,426 B1 | 11/2002 | Fenn et al. |
| 6,530,944 B2 | 3/2003 | West et al. |
| 6,645,517 B2 | 11/2003 | West et al. |
| 6,660,381 B2 | 12/2003 | Halas et al. |
| 6,663,621 B1 | 12/2003 | Winston et al. |
| 6,685,730 B2 | 2/2004 | West et al. |
| 6,685,986 B2 | 2/2004 | Oldenburg et al. |
| 6,699,724 B1 | 3/2004 | West et al. |
| 6,778,316 B2 | 8/2004 | Halas et al. |
| 7,087,040 B2 | 8/2006 | McGuckin, Jr. et al. |
| 7,274,847 B2 | 9/2007 | Gowda |
| 7,371,457 B2 | 5/2008 | Oldenburg et al. |
| 7,438,411 B2 | 10/2008 | Payne et al. |
| 8,057,418 B2 | 11/2011 | Kornling et al. |
| 8,170,657 B1 | 5/2012 | Ehrenreich |
| 8,211,095 B2 | 7/2012 | Gowda |
| 8,267,927 B2 | 9/2012 | Dalal et al. |
| 9,211,419 B2 | 12/2015 | Krishnan et al. |
| 10,568,693 B2 | 2/2020 | Goodrich et al. |
| 10,993,769 B2 | 5/2021 | Goodrich et al. |
| 2003/0060813 A1 | 3/2003 | Loeb et al. |
| 2005/0165462 A1 | 7/2005 | Bays et al. |
| 2005/0222556 A1 | 10/2005 | Ariura et al. |
| 2006/0084960 A1 | 4/2006 | Mester et al. |
| 2006/0189965 A1 | 8/2006 | Litvak |
| 2007/0208400 A1 | 9/2007 | Nadkarni et al. |
| 2008/0160090 A1 | 7/2008 | Oraevsky et al. |
| 2009/0171330 A1 | 7/2009 | Taylor et al. |
| 2009/0240242 A1 | 9/2009 | Neuberger |
| 2011/0052672 A1 | 3/2011 | Krishnan et al. |
| 2012/0059307 A1* | 3/2012 | Harris ............... A61P 31/04 977/773 |
| 2015/0005755 A1 | 1/2015 | Kazic et al. |
| 2015/0018807 A1 | 1/2015 | Kircher et al. |
| 2015/0094698 A1 | 4/2015 | Gowda et al. |
| 2016/0008636 A1 | 1/2016 | Warnking |
| 2016/0022976 A1 | 1/2016 | Peyman |
| 2017/0065343 A1 | 3/2017 | Mickelsen |
| 2017/0105715 A1 | 4/2017 | Kasic |
| 2017/0290629 A1 | 10/2017 | Brown |
| 2018/0280546 A1 | 10/2018 | Tomitaka et al. |
| 2019/0290360 A1 | 9/2019 | Goodrich et al. |
| 2020/0155234 A1 | 5/2020 | Goodrich et al. |

FOREIGN PATENT DOCUMENTS

| | | |
|---|---|---|
| EP | 0195375 A2 | 9/1986 |
| EP | 3554404 | 10/2019 |
| JP | 62-268552 | 11/1987 |
| JP | 2002-017743 A | 1/2002 |
| MX | MX/a/2019/007095 | 6/2019 |
| PT | 891157 E | 9/2001 |
| WO | WO 1997/037601 A1 | 10/1997 |
| WO | WO 2011/020064 A2 | 2/2011 |
| WO | WO 2011/127061 A1 | 10/2011 |
| WO | WO 2015/061883 | 5/2015 |
| WO | WO 2018/112261 | 6/2018 |

OTHER PUBLICATIONS

International Search Report and Written Opinion received in PCT Application No. PCT/US2017/066522, dated Feb. 16, 2018 in 15 Pages.

International Preliminary Report on Patentability received in PCT Application No. PCT/2017/066522, dated Feb. 16, 2018.

* cited by examiner

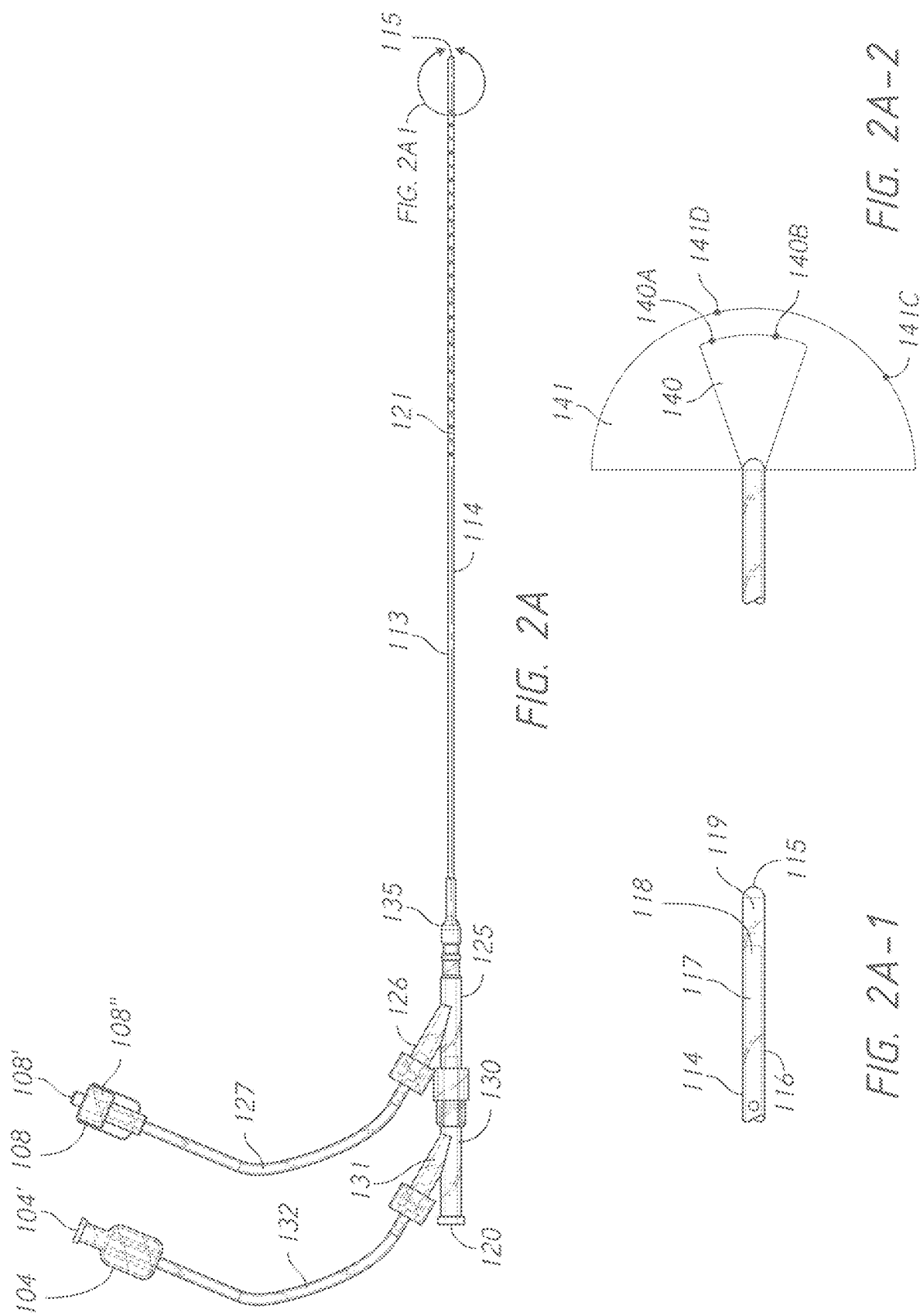

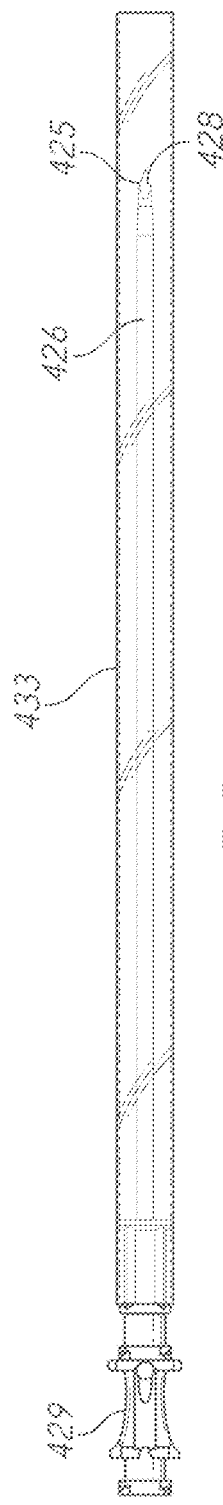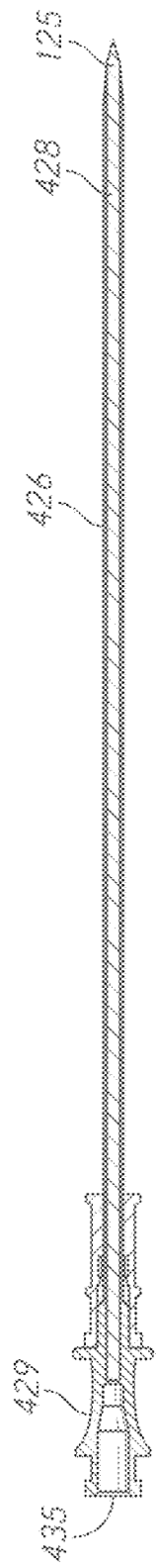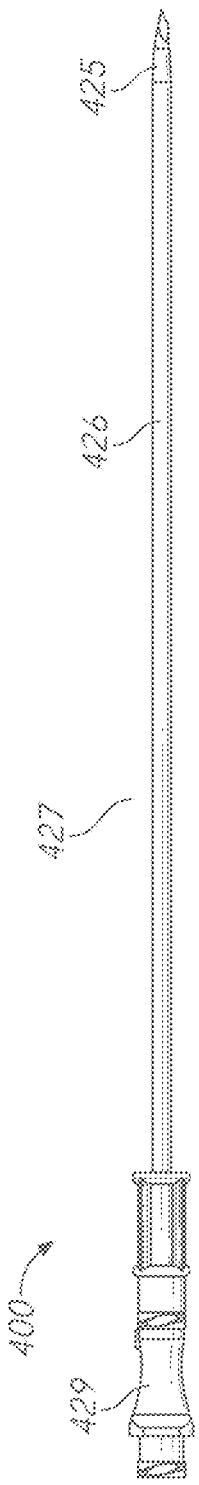
FIG. 6A  FIG. 6A-1  FIG. 6A-2  FIG. 6A-3  FIG. 6A-4

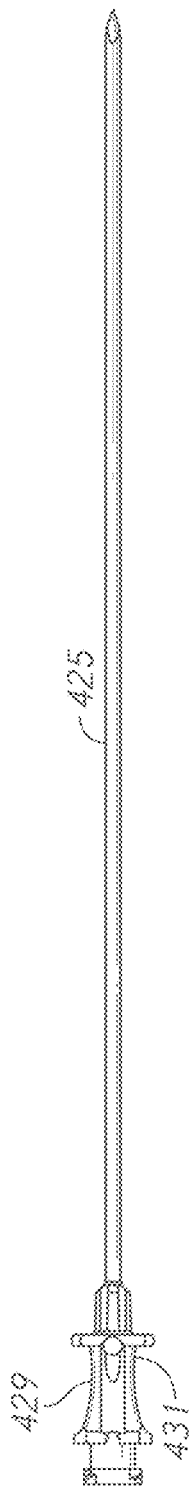
FIG. 6B
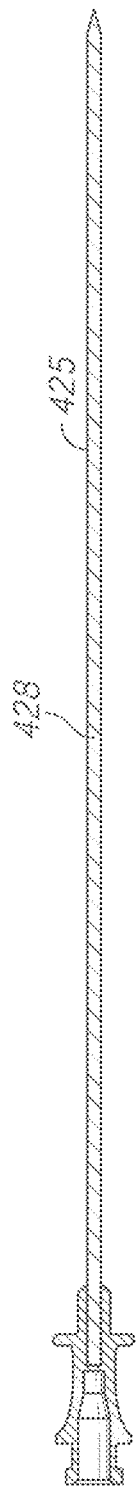
FIG. 6B-1
FIG. 6B-2
FIG. 6B-3
FIG. 6B-4

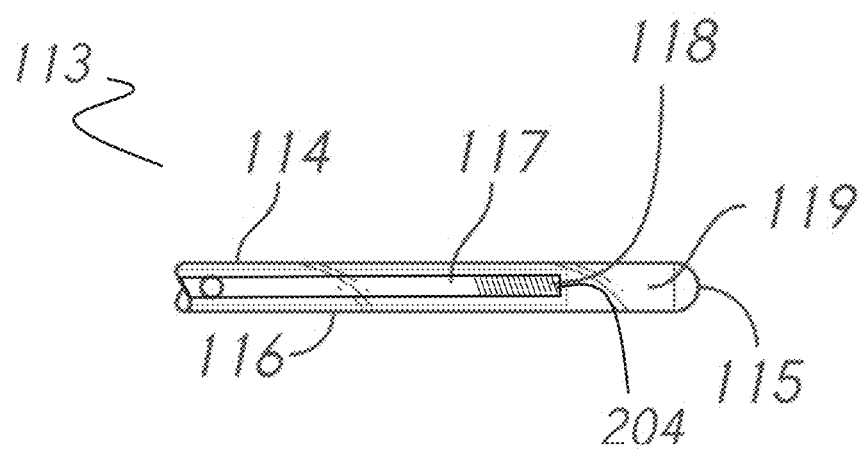
FIG. 7J1

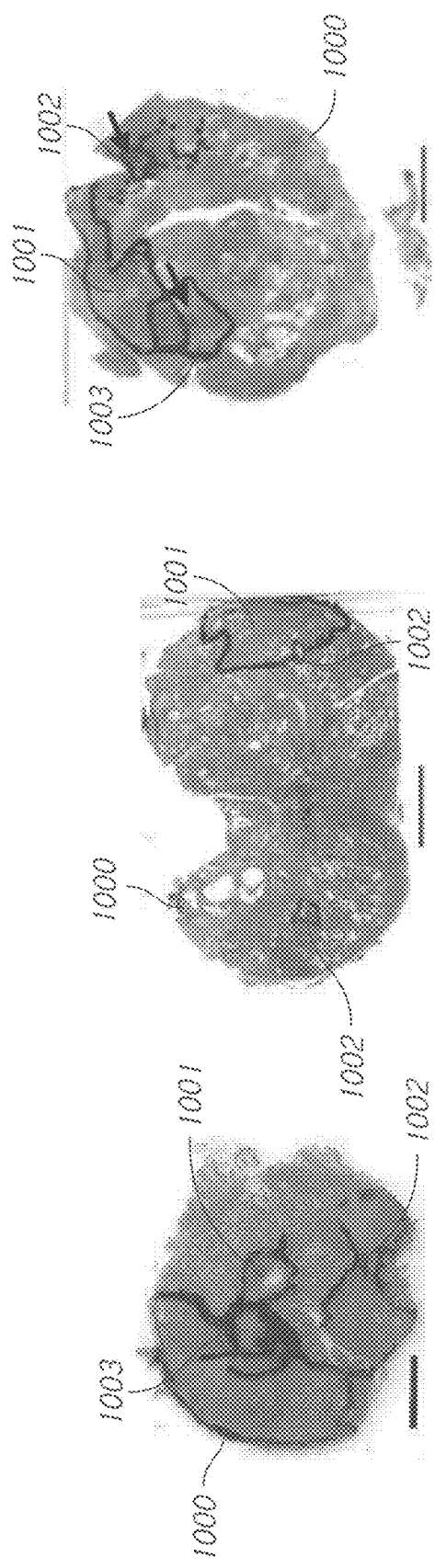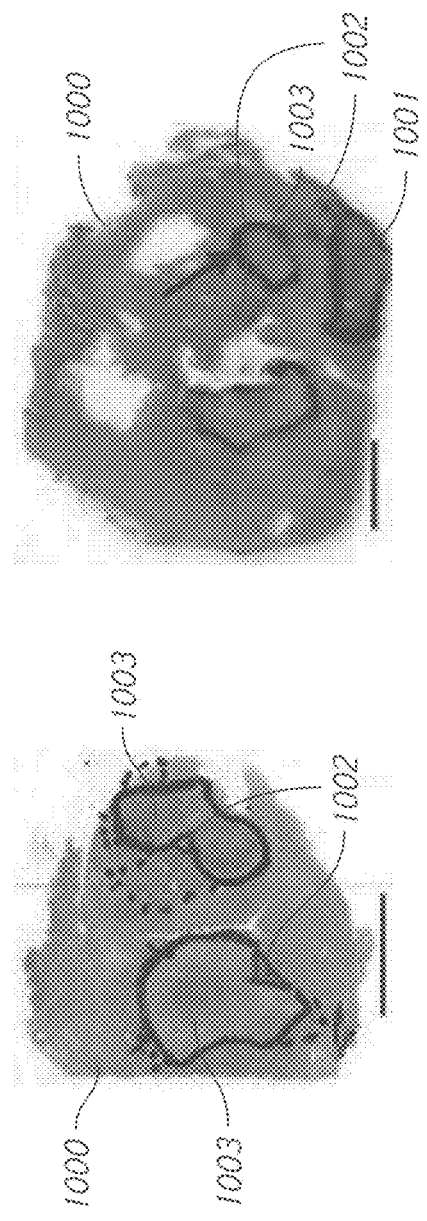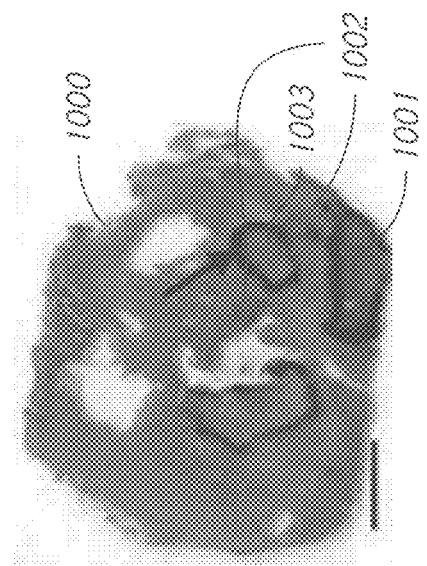
FIG. 14E  FIG. 14F  FIG. 14G  FIG. 14H  FIG. 14I

DEVICES AND SYSTEMS FOR ABLATION THERAPY

CROSS REFERENCE TO RELATED APPLICATIONS

This patent application is a continuation of U.S. application Ser. No. 16/746,765, filed Jan. 17, 2020, which is a continuation of U.S. application Ser. No. 16/327,292, filed Feb. 21, 2019, which is the U.S. National Phase entry of International PCT Application No. PCT/US2017/066522, filed Dec. 14, 2017, which claims the benefit of priority to U.S. Provisional Patent Application No. 62/435,431, filed Dec. 16, 2016. The forgoing applications are hereby incorporated by reference in their entireties for all purposes.

BACKGROUND

Field

Methods, systems, kits, and devices for irradiation of nanoparticles for therapeutic treatments ablation are disclosed.

Description of the Related Art

Thermal and radiative ablation can be used to burn and/or ablate tissues for therapeutic methods. These techniques can be used to ablate cancer tissues and tumors.

SUMMARY

Some embodiments disclosed herein pertain to methods, systems, kits, and devices for therapeutic treatments and/or ablation therapy of tissues. Some embodiments pertain to a laser illuminating system. Any of the embodiments described above, or described elsewhere herein, can include one or more of the following features.

In some embodiments, the laser illuminating system comprises a laser illuminator assembly. In some embodiments, the laser illuminator assembly comprises an elongated introducer probe with a domed, transmissive sealed end.

In some embodiments, the laser illuminating system comprises an optical fiber with a diffuser tip and an optical fiber connector. In some embodiments, the optical fiber connector is configured to engage the laser illuminator assembly. In some embodiments, when the optical fiber connector is engaged with the laser illuminator assembly, the diffuser tip of the optical fiber is positioned within the laser illuminator assembly.

In some embodiments, the laser illuminating system comprises a laser source configured to be in optical communication with the optical fiber. In some embodiments, the laser source is configured to transmit radiation through the optical fiber to the laser illuminator assembly. In some embodiments, when activated, the laser source transmits electromagnetic radiation through optical fiber and through the sealed end.

In some embodiments, the laser illuminating system comprises a coolant reservoir. In some embodiments, the coolant reservoir is in fluidic communication with the laser illuminator assembly. In some embodiments, the laser illuminator assembly comprises a coolant inlet tube configured to convey coolant from the coolant reservoir to the laser illuminator assembly.

In some embodiments, the laser illuminating system comprises a pump configured to convey coolant from the coolant reservoir to the laser illuminator assembly via the coolant inlet tube to cool the optical fiber. In some embodiments, the laser illuminating system comprises a coolant recovery bag in fluidic communication with the laser illuminator assembly and configured to receive coolant from the laser illuminator assembly. In some embodiments, the laser illuminator assembly comprises a coolant outlet tube configured to convey coolant from the laser illuminator assembly to the coolant recovery bag.

In some embodiments, the laser illuminating system comprises an actuator configured to activate and deactivate the laser source. In some embodiments, the actuator is a foot pedal. In some embodiments, the actuator also controls the pump. In some embodiments, the laser and the pump are activated by the actuator substantially simultaneously. In some embodiments, the laser and the pump are deactivated by the actuator substantially simultaneously.

In some embodiments, the coolant inlet tube is tygon material. In some embodiments, the coolant inlet tube is about 4 meters in length. In some embodiments, the coolant inlet tube is configured to allow coolant flow at a low rate. In some embodiments, the coolant inlet tube is configured to allow coolant flow at a rate of about 8 ml/min.

In some embodiments, the laser source provides a radiation having a wavelength that is near infrared wavelength. In some embodiments, the laser source provides a radiation that has a wavelength ranging from about 805 nm to about 810 nm.

In some embodiments, the optical fiber comprises a diffusive portion configured to distribute radiation from the optical fiber and out of the laser illuminator assembly.

In some embodiments, a length of the diffusive portion of the optical fiber ranges from about 1.0 cm to about 1.8 cm. In some embodiments, the diffusive portion of the optical fiber may be of a length equal to or less than about: 50 mm, 30 mm, 18 mm, 10 mm, values between the aforementioned values, or ranges including and/or spanning those values.

Some embodiments disclosed herein pertain to a method of treating a prostate tumor. Any of the embodiments described above, or described elsewhere herein, can include one or more of the following features.

In some embodiments, the method comprises injecting and/or infusing nanoparticles into a patient systemically. In some embodiments, the nanoparticles are adapted to transduce infrared light into heat energy. In some embodiments, the method comprises allowing the nanoparticles to preferentially accumulate in the prostate tumor. In some embodiments, the method comprises inserting a trocar assembly comprising a trocar and a catheter sheathed around the trocar into the patient at a first insertion point. In some embodiments, the method comprises positioning the trocar assembly in the patient by passing the trocar assembly through the prostate tumor such that the trocar assembly passes through a proximal face of the tumor and terminates at a distal side of the tumor creating a first path within the tumor. In some embodiments, the method comprises removing the trocar from the patient and leaving the catheter in the patient within the first path. In some embodiments, the method comprises inserting an introducer probe of a laser illuminator assembly into the catheter. In some embodiments, the laser illuminator assembly comprises an introducer probe, the introducer probe being elongate and comprising a first lumen and terminating in a sealed domed end configured to allow laser light transmission. In some embodiments, the laser illuminator assembly comprises an internal tube located within the first lumen of the introducer probe, the internal tube comprising a second lumen. In some embodiments, the laser illuminator assembly comprises an optical fiber configured to receive photons from a laser source, wherein the optical fiber is positioned within the second lumen of the introducer probe and is configured to transmit laser radiation through the domed end of the introducer probe. In some embodiments, the first lumen is in fluidic communication with the second lumen.

In some embodiments, the method comprises guiding the introducer probe to a first position within the first path in the tumor, wherein the first position is located at or near the distal side of the tumor. In some embodiments, the method comprises activating the laser source when the introducer probe is at the first position within the first path to generate non-ablative infrared radiation at the first position for a first period of time wherein the infrared radiation causes heating of the nanoparticles to an ablative temperature. In some embodiments, the method comprises withdrawing the catheter and the introducer probe to a second position within the first path in the tumor, the second position being proximally located relative to the first position. In some embodiments, the method comprises activating the laser source when the introducer probe is at the second position to generate non-ablative infrared radiation for a second period of time wherein the infrared radiation causes heating of the nanoparticles to an ablative temperature.

In some embodiments, the method comprises removing the catheter and the laser illuminator from the first path. In some embodiments, the method comprises inserting the trocar assembly into the patient at a second insertion point that is laterally disposed on the proximal side of the tumor from the first insertion point. In some embodiments, the method comprises positioning the trocar assembly in the patient by passing the trocar assembly through the prostate tumor such that the trocar assembly passes through the proximal face of the tumor and terminates at the distal side of the tumor and creates a second path through the tumor. In some embodiments, the method comprises inserting the introducer probe into the catheter. In some embodiments, the method comprises guiding the introducer probe to a first position within the second path in the tumor, wherein the first position is located near the distal side of the tumor. In some embodiments, the method comprises activating the laser source when the introducer probe is at the first position within the second path to generate non-ablative infrared radiation at the first position of the second path for a third period of time wherein the infrared radiation causes heating of the nanoparticles to an ablative temperature. In some embodiments, the method comprises withdrawing the catheter and the introducer probe to a second position within the second path in the tumor, the second position being proximally located relative to the first position in the second path. In some embodiments, the method comprises activating the laser source when the introducer probe is at the second position of the second path to generate non-ablative infrared radiation for a fourth period of time wherein the infrared radiation causes heating of the nanoparticles to an ablative temperature.

In some embodiments, the first position and the second position of the first path are about 8 mm apart. In some embodiments, the first position and the second position of the second path are about 8 mm apart. In some embodiments, a template grid is used to position the trocar assembly at the first insertion point and at the second insertion point.

In some embodiments, the method comprises inserting the trocar assembly into the patient at additional insertion points that are laterally disposed on the proximal side of the tumor from the first insertion point and second insertion points.

In some embodiments, the template grid is used to position the trocar assembly at the additional insertion points.

In some embodiments, the laser illuminator assembly comprises a coolant outlet in fluidic communication the first lumen and a coolant inlet in fluidic communication with the second lumen wherein the laser illuminator assembly is configured to allow the passage of a coolant from the coolant inlet through the second lumen into the first lumen and out of the coolant outlet.

In some embodiments, the laser illuminator is activated by an actuator that is controlled by a user. In some embodiments, the user activates the laser illuminator using the actuator, coolant flows into the first inlet of the laser illuminator assembly and wherein when the laser illuminator is not active, coolant does not flow laser illuminator assembly. In some embodiments, the actuator is a foot pedal.

In some embodiments, the laser illuminator emits radiation having a near infrared wavelength. In some embodiments, the laser illuminator emits radiation having a near infrared wavelength ranging from about 805 nm to about 810 nm. In some embodiments, the laser illuminator emits radiation that is of insufficient power and/or intensity to induce photothermal coagulation of tissue. In some embodiments, the optical fiber comprises a diffuser tip that distributes the non-ablative infrared radiation within the tumor. In some embodiments radiation is distributed laterally or sideways from the diffuser tip. In some embodiments, radiation is not transmitted through the tip and/or terminus of the optical fiber and/or diffuser tip. In some embodiments, radiation is transmitted through the tip and/or terminus of the optical fiber and/or diffuser tip and through the sealed domed end. In some embodiments, the laser illuminator emits radiation between about 3.5 W/cm and about 4.5 W/cm of the diffuser tip.

Some embodiments pertain to a laser illuminator device comprising an introducer probe. Any of the embodiments described above, or described elsewhere herein, can include one or more of the following features.

In some embodiments, the introducer probe comprises a first lumen terminating in a sealed domed end configured to allow laser light transmission. In some embodiments, the introducer probe comprises an internal tube located within the first lumen of the introducer probe, the internal tube comprising a second lumen In some embodiments, the introducer probe comprises an optical fiber. In some embodiments, the optical fiber is positioned within the second lumen. In some embodiments, the optical fiber can transmit laser radiation through the domed end of the introducer probe. In some embodiments, the first lumen is in fluidic communication with the second lumen.

In some embodiments, the device comprises a coolant outlet in fluidic communication the first lumen and a coolant inlet in fluidic communication with the second lumen. In some embodiments, the device comprises the laser illuminator assembly is configured to allow the passage of a coolant from the coolant inlet through the second lumen into the first lumen and out of the coolant outlet. In some embodiments, the fluid inlet and the fluid outlet are configured to interact with different connectors to prevent improper routing of coolant through the laser illuminator device. In some embodiments, the fluid inlet and the fluid outlet are of different sexes. In some embodiments, the fluid inlet comprises a male connector and the fluid outlet comprises a female connector.

In some embodiments, the optical fiber comprises a diffusive portion configured to distribute radiation from the optical fiber and out of the laser illuminator assembly. In some embodiments, the length of the diffusive portion of the optical fiber ranges from about 1.0 cm to about 1.8 cm. In some embodiments, the diffusive portion of the optical fiber may be of a length equal to or less than about: 50 mm, 30 mm, 18 mm, 10 mm, values between the aforementioned values, or ranges including and/or spanning those values.

In some embodiments, the outside of the probe is graduated. In some embodiments, the graduations are about 4 mm apart.

Some embodiments pertain to a method of treating a tumor. Any of the embodiments described above, or described elsewhere herein, can include one or more of the following features.

In some embodiments, the method comprises injecting nanoparticles into a patient systemically wherein the nanoparticles are adapted to transduce infrared light into heat energy.

In some embodiments, the method comprises allowing the nanoparticles to preferentially accumulate in the tumor.

In some embodiments, the method comprises inserting a trocar assembly comprising a trocar and a catheter sheathed around the trocar into the patient at a first insertion point.

In some embodiments, the method comprises positioning the trocar assembly in the patient by passing the trocar assembly through the tumor such that the trocar assembly passes through a proximal face of the tumor and terminates at a distal side of the tumor and creates a first path within the tumor.

In some embodiments, the method comprises removing the trocar from the patient and leaving the catheter in the patient within the first path.

In some embodiments, the method comprises inserting an introducer probe of a laser illuminator assembly into the catheter wherein the laser illuminator assembly comprises an introducer probe. In some embodiments, the introducer probe comprises a first lumen and terminating in a sealed domed end configured to allow laser light transmission. In some embodiments, the the introducer probe comprises an internal tube located within the first lumen of the introducer probe, the internal tube comprising a second lumen. In some embodiments, the method comprises the introducer probe comprises an optical fiber configured to receive photons from a laser source. In some embodiments, the optical fiber is positioned within the second lumen and configured to transmit laser radiation through the domed end of the introducer probe. In some embodiments, the first lumen is in fluidic communication with the second lumen.

In some embodiments, the method comprises guiding the introducer probe to a first position within the first path in the tumor, wherein the first position is located near the distal side of the tumor.

In some embodiments, the method comprises activating the laser source when the introducer probe is at the first position within the first path to generate subablative infrared radiation at the first position for a first period of time thereby heating the nanoparticles to an ablative temperature.

In some embodiments, the method comprises withdrawing the catheter and the introducer probe to a second position within the first path in the tumor, the second position being proximally located relative to the first position In some embodiments, the method comprises activating the laser source when the introducer probe is at the second position to generate subablative infrared radiation for a second period of time thereby heating the nanoparticles to an ablative temperature.

Some embodiments pertain to a method of treating a tumor. Any of the embodiments described above, or described elsewhere herein, can include one or more of the following features. In some embodiments, the method comprises obtaining a laser illuminator comprising an introducer probe. In some embodiments, the introducer probe comprises a domed-end and an optical fiber, the optical fiber being in optical communication with a laser source. In some embodiments, the method comprises positioning the introducer probe in a tissue comprising the tumor by passing the introducer probe through a proximal face of the tissue to a distal side of the tissue to a first position. In some embodiments, the method comprises activating the laser source while the introducer probe is at the first position to transmit sub-ablative infrared radiation to the tissue for a first period of time. In some embodiments, the method comprises withdrawing the introducer probe to a second position in the tissue, the second position being proximally located relative to the first position. In some embodiments, the method comprises activating the laser source when the introducer probe is at the second position to transmit sub-ablative infrared radiation to the tissue for a second period of time.

BRIEF DESCRIPTION OF THE DRAWINGS

FIG. 2A illustrates an embodiment of a laser catheter assembly.

FIGS. 2A1 and 2A2 illustrate expanded views of the laser catheter assembly shown in FIG. 2A.

FIGS. 6A-6B4 illustrate views of a trocar sleeve assembly.

FIG. 7A-7J1 illustrate the insertion and illumination of a test tissue using an embodiment of a laser catheter assembly described herein.

FIGS. 14A-14I are photographs of 9 whole-mount sections of patients' prostates (scale bars=1 cm).

DETAILED DESCRIPTION

Figure 1:
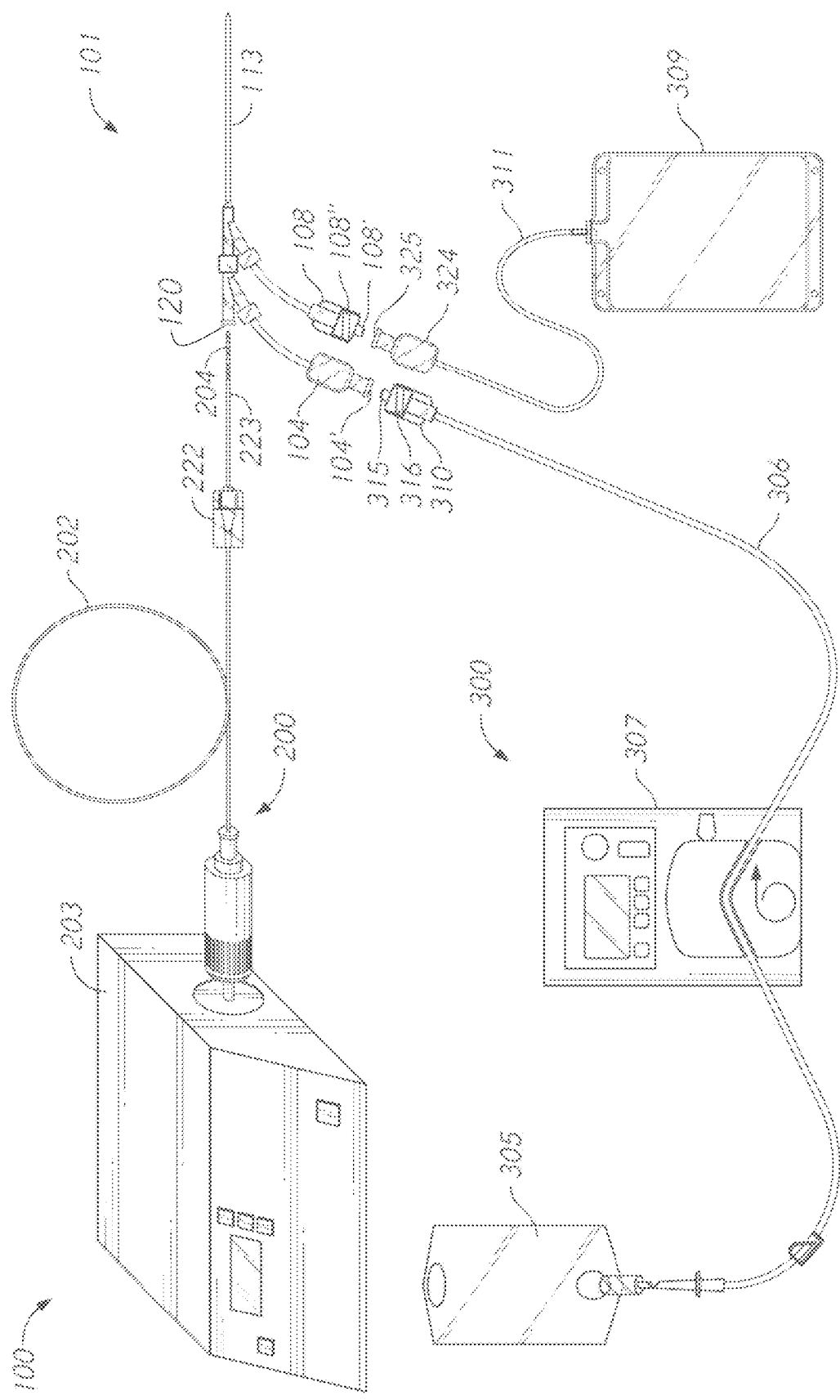
FIG. 1 illustrates an embodiment of a laser illuminating system.

Various methods, systems, and devices for treating tumors are disclosed. Some embodiments disclosed herein pertain to methods of treating tumors, systems used for irradiating tissue and tumors with electromagnetic radiation, components and devices of that system, and kits for providing systems used for irradiating tissue and tumors with electromagnetic radiation. In some embodiments, the system provides non-ablative infrared radiation (e.g., radiation that is of insufficient intensity to ablate tissue by itself and/or sub-ablative radiation) that is absorbed by nanoparticles. In some embodiments, the nanoparticles absorb the radiation converting it into heat energy. In some embodiments, though the infrared radiation itself may be sub-ablative, the heat energy generated by the nanoparticles is sufficient to cause thermal coagulation, hyperthermia, and/or tissue ablation. A variety of methods, devices, systems, and kits for treating tumors and ablating tissue are described below to illustrate various examples that may be employed to achieve one or more desired improvements. These examples are only illustrative and are not intended in any way to restrict the general inventions presented and the various aspects and features of these inventions. Furthermore, the phraseology and terminology used herein is for the purpose of description and should not be regarded as limiting. No features, structure, or step disclosed herein is essential or indispensable. Any of the systems or methods disclosed herein can exclude one or more steps or features described herein.

Optical properties govern how optical wavelength photons interact with biological tissue. These are optical scatter and optical absorption. Scatter results when a photon encounters a change in index of refraction, such as at the membrane of a cell. A scattered photon will continue to travel through the tissue, but in an altered direction. Absorption results in the deposition of the photon's energy into whatever absorbed it, such as a hemoglobin molecule or cell organelle. The energy of the absorbed photon is generally converted into heat, which radiates away from the absorption site.

Absorption of photon energy can cause photocoagulation, which results in the unraveling of proteins, leading to a dramatic increase in optical scatter and reduction in the ability of light to penetrate into tissue. The change of egg white from clear to opaque when heated in a frying pan is a well-known example of this phenomenon. Photothermal coagulation as a therapeutic method can make use of the ability of laser energy to be transmitted through optical fiber in order to deliver particular amounts of energy interstitially into tissue. Laser Interstitial Thermal Therapy (LITT) is the technique of delivering sufficient optical power to directly generate thermal coagulation in tissue. Essentially, optical energy is delivered into tissue at a rate greater than the body's ability to remove the resulting heat. This heat can result in hyperthermia and tissue ablation.

However, the effective treatment depth of LITT and other photon-based therapies can be hindered by light scatter and absorption in tissues (including that caused by thermal coagulation). This scatter and absorption can result in light intensity that diminishes exponentially with increased distance from the light source into tissue. A further constraint is that light intensity, or irradiance (measured in $W/cm^2$), also declines and/or decreases in the radial direction when delivered by a one-dimensional source (e.g., optical fiber diffusers used to deliver laser light interstitially into tissue). The net result is that optical irradiance is higher immediately adjacent to the optical source delivering it and much lower in areas just outside the immediate vicinity of the optical source (e.g., a diffuser). Photon-based processes of phototherapy are also non-specific; the shape of the region of coagulation is a function of the shape of the energy source, and the volume of the region of coagulation is dependent upon the total energy deposited. For example, current laser catheters used for photon-based processes use optical fiber diffusers and 12-15 W of power to generate ellipsoidal coagulation zones around the diffuser. Thus, selectivity to treat target tissue is low.

Further, because current systems require high power irradiance, high laser temperatures occur that can destroy and/or deform laser delivery catheters. Active cooling is used to prevent carbonization of the tissue immediately around the laser delivery catheter and/or to prevent instrument damage. However, these systems do not actively regulate coolant used to cool these laser catheters and typically allow a flow of ~15-20 mL/min of room temperature saline in a thin jacket surrounding the optical fiber diffuser to prevent tissue carbonization on the laser catheter. An uncontrolled coolant flow can lead to cooling of tissues exposed to the cooling source between laser applications.

Some embodiments disclosed herein pertain to methods, devices, systems, and kits for using non-ablative radiation to generate particle-directed photothermal coagulation (e.g., using nanoparticles or other agents). In some embodiments, the disclosed techniques and devices allow improved selectivity in targeting of tissues and in effectively treating tissues. Some embodiments disclosed herein pertain to systems and devices used to generate radiation at a site where photothermal coagulation, hyperthermia, and/or tissue ablation is desired.

In some embodiments, the methods and devices pertain to particle-directed (e.g., with nanoparticles) photothermal coagulation used for treating tumors. In some embodiments, the methods involve injecting nanoparticles into a patient with a tumor (or another tissue that is to be targeted). In some embodiments, the nanoparticles are allowed to accumulate in the tumor over a defined period of time. In some embodiments, once the nanoparticles have accumulated in a site of interest, the laser probe of a laser catheter assembly is positioned (e.g., inserted, placed, etc.) into or near the site of interest (e.g., in or near a tumor). In some embodiments, the laser catheter assembly is activated to deliver electromagnetic radiation (e.g., ultraviolet light, visible light, near-infrared light, far-infrared light, microwave, etc.) to the nanoparticles. In some embodiments, the radiation is infrared radiation. In some embodiments, the laser catheter assembly delivers radiation that is of insufficient intensity to cause photothermal coagulation (e.g., radiation that is non-ablative radiation and/or sub-ablative), hyperthermia, and/or tissue ablation by itself (e.g., in the absence of the nanoparticles). In some embodiments, the radiation intensity is transduced into heat energy by the nanoparticles. In some embodiments, the heat transduced by the nanoparticles is sufficient to cause ablative hyperthermia, tissue coagulation, and/or tissue ablation.

In some embodiments, the nanoparticles used in the disclosed methods are designed to absorb infrared radiation and convert it to heat energy. In some embodiments, gold nanoshells (e.g., AuroShells, etc.) are used as nanoparticles that transduce the sub-ablative infrared radiation to ablative temperatures. While, gold nanoshells (e.g., AuroShells, etc.) are used as a representative nanoparticle for illustration, it should be noted that any nanoparticle (or microparticle) that absorbs infrared photons and transduces those photons to heat energy is envisioned. Without being bound to any particular theory, it is believed that absorption of a photon by a nanoshell effectively annihilates the photon and results in the transduction of its energy into heat, which is emitted into the surrounding tissue. When a photon is scattered by a particle (e.g., not absorbed), the scattered photon is available for absorption elsewhere (e.g., by tissue, another nanoshell, etc.). Transducing nanoparticles include, among others: nanoshells (including gold-shell silica core nanoshells such as Auroshells, gold-gold sulfide nanoshells and other variants), solid nanospheres (gold, silver, etc.), metal nanorods (gold, silver, etc.), nanostars, hollow nanoparticles, nanocages, elliptical "nanorice," carbon particles, fullerenes, carbon fullerenes, metallic nanoparticles, metal colloids, carbon particles, carbon nanotubes, buckyballs, and any combination thereof.

In some embodiments, the methods disclosed herein are used to target tissues for treatment. In some embodiments, the target tissue is tumor tissue. In some embodiments, the tumor targets include tumors caused by cancer. In some embodiments, the tumors are those caused by colorectal cancer, brain cancer, lung cancer, breast cancer, head and neck cancer, pancreatic cancer, ovarian cancer, melanoma cancer, prostate cancer, and other forms of cancer. In some embodiments, the techniques disclosed herein are suitable for treating tumors in a tissue and/or for preserving the function of healthy tissue while destroying the underlying tumor tissue. For example, in some embodiments, the techniques and devices disclosed herein can be used to specifically target tumor tissues or dysfunctional tissues. The loss of function of a particular healthy tissue can have devastating effects for a patient's quality of life. For example, surgical manipulation to remove cancer tumor tissue from the throat can cause loss of speech. Surgical manipulation to remove cancer tumor tissue from the prostate can cause loss of sexual function. In current methods of ablation, tissues are heated based on the placement of a heating instrument in a tumor. The heating element is activated, thereby killing tissue surrounding it, including healthy tissue. In some embodiments, the treatments disclosed herein can partially, substantially, and/or fully preserve the structure and/or function of the non-diseased underlying healthy tissue to promote or substantially preserve normal function of those underlying tissues.

In some embodiments, the methods involve injecting (e.g., infusing) nanoparticles into the patient systemically. Systemic introduction can involve the introduction of nanoparticles into the circulatory system and/or at a site within the body but away from or remote from the target site. In some embodiments, the nanoparticles can be introduced to a patient via parenteral administration routes (e.g., injection via the intravenous, intramuscular, sub-cutaneous, intralesional, intraperitoneal, etc.). These sites can be located in areas of the patient's body that are not proximally located to the site of treatment (e.g., at sites in the body other than the tumor site). For instance, nanoparticles accumulate preferentially within tumors largely as a result of their size and passive extravasation from the leaky, chaotic and immature vasculature of tumors; a phenomenon referred to as the "enhanced permeability and retention" (EPR) effect. In some embodiments, this passive accumulation allows targeted deposition of the radiation transducers and affords photothermal coagulation therapy that is tumor-specific.

In some embodiments, after being introduced to the body, the nanoparticles are allowed to passively accumulate at a tumor. In some embodiments, this passive accumulation is achieved by the passage of a defined period of time. In some embodiments, the nanoparticles are allowed to accumulate in the tumor for a period of time ranging from between equal to or at least about 12 hours and/or less than or equal to about 36 hours after infusion and/or injection. In some embodiments, the nanoparticles are allowed to accumulate in the tumor site for a period of at least: about 12 hours, 24 hours, about 36, or ranges including and/or spanning the aforementioned values.

In some embodiments, the nanoparticles accumulate in the perivascular space of tumor neovasculature and serve as foci for laser energy. In some embodiments, after accumulation at a site of interest, laser and/or electromagnetic energy is used to heat the nanoparticles. In some embodiments, this laser energy (e.g., electromagnetic energy) heats the nanoparticles to a sufficient temperature to cause thermal coagulation, hyperthermia, and/or ablation of target tissue.

In some embodiments, laser energy is generated at a target site for treatment using a laser illuminating system 100 as shown in FIG. 1. In some embodiments, as shown in FIG. 1, the laser illuminating system 100 comprises a laser catheter assembly 101 (e.g., a laser illuminator). In some embodiments, the laser illuminating system further comprises one or more of an illuminating system 200 and a cooling system 300. In some embodiments, the illuminating system 200 comprises an optical fiber 202 and a laser source 203. In some embodiments, the optical fiber 202 is configured to connect to, to be in optical communication with, and/or to receive laser energy from the laser source 203. In some embodiments, as disclosed elsewhere herein, the laser source, the optical fiber, and/or the laser catheter are in optical communication. In some embodiments, the cooling system comprises one or more of a coolant reservoir 305, a coolant pump 307, and/or a coolant recovery bag 309. In some embodiments, as disclosed elsewhere herein, the coolant reservoir, the laser catheter assembly, and/or the coolant recovery bag are configured to be in fluidic communication with each other. In some embodiments, the laser illuminating system includes the laser catheter assembly but lacks one or more of the other features, such as the illuminating system and/or the coolant delivery system and components thereof.

In some embodiments, as shown in FIG. 1, the laser catheter assembly 101 is configured to receive coolant via a coolant inlet connector 104. In some embodiments, the laser illuminating system 100 comprises a coolant reservoir 305 (e.g., a bag, bottle, etc.). In some embodiments, the coolant reservoir 305 is in fluidic communication with the coolant inlet connector 104 via a coolant inlet conduit 306. In some embodiments, coolant from the coolant reservoir 305 is transferred into the laser catheter assembly 101 via the coolant inlet connector 104 using a coolant pump 307. In some embodiments, the coolant inlet conduit 306 has an inlet conduit connector 310 that is configured to interact with the coolant inlet connector 104.

In some embodiments, the laser catheter assembly 101 is configured to expel coolant via a coolant outlet connector 108. In some embodiments, the laser illuminating system 100 comprises a coolant recovery bag 309 (e.g., a bag, bottle, etc.). In some embodiments, the coolant recovery bag 309 is in fluidic communication with the coolant outlet connector 108 via a coolant outlet conduit 311. In some embodiments, coolant from the laser catheter assembly 101 is transferred into the coolant recovery bag 309 via the coolant outlet connector 108. In some embodiments, the coolant outlet conduit 311 has an outlet conduit connector 312 that is configured to interact with the coolant outlet connector 108.

In some embodiments, as shown in FIG. 2A, the inlet and outlet connectors of the laser catheter assembly 101 are of different sex. In some embodiments, this configuration can prevent incorrect connection and/or mismatching of the inlet and outlet connectors of the laser catheter assembly 101 to the coolant supply and recovery attachments (e.g., preventing backward connection). For example, as shown in FIG. 1, the coolant inlet connector 104 can be a female connector with a female receiving portion 104' and the coolant supply inlet 310 can have a male connection with a male protrusion 315 and optionally a shroud 316 (e.g., a hood, a threaded shroud, etc.) while the coolant outlet connector 108 can be a male connector with a male protrusion 108' and optionally a shroud 108" (e.g., a hood, a threaded shroud, etc.) and the coolant outlet conduit connector 324 can have a female connection with a female receiving portion 325. In some embodiments, the coolant inlet connector 104 can be a male connector while the coolant outlet connector 108 can be a female connector (not shown). In some embodiments, instead of or in addition to having different sexes, the inlet connector 104 and outlet connector 108 can be color-coded to match a color on the inlet conduit connector 310 and the outlet conduit connector 324 (not shown). For example, in some embodiments, the inlet connector 104 and the inlet conduit connector 310 could be one color (e.g., red, orange, yellow, green, cyan, blue, indigo, violet, purple, magenta, pink, brown, white, gray, black), and the outlet connector 108 and the outlet conduit connector 324 could be of another different color (e.g., red, orange, yellow, green, cyan, blue, indigo, violet, purple, magenta, pink, brown, white, gray, black). In some embodiments, the male and female connectors can be luer connectors (which in some embodiments can include an ISO 594-compliant luer taper). In some embodiments, the inlet and outlet connectors are not of a different sex.

Figure 2B:
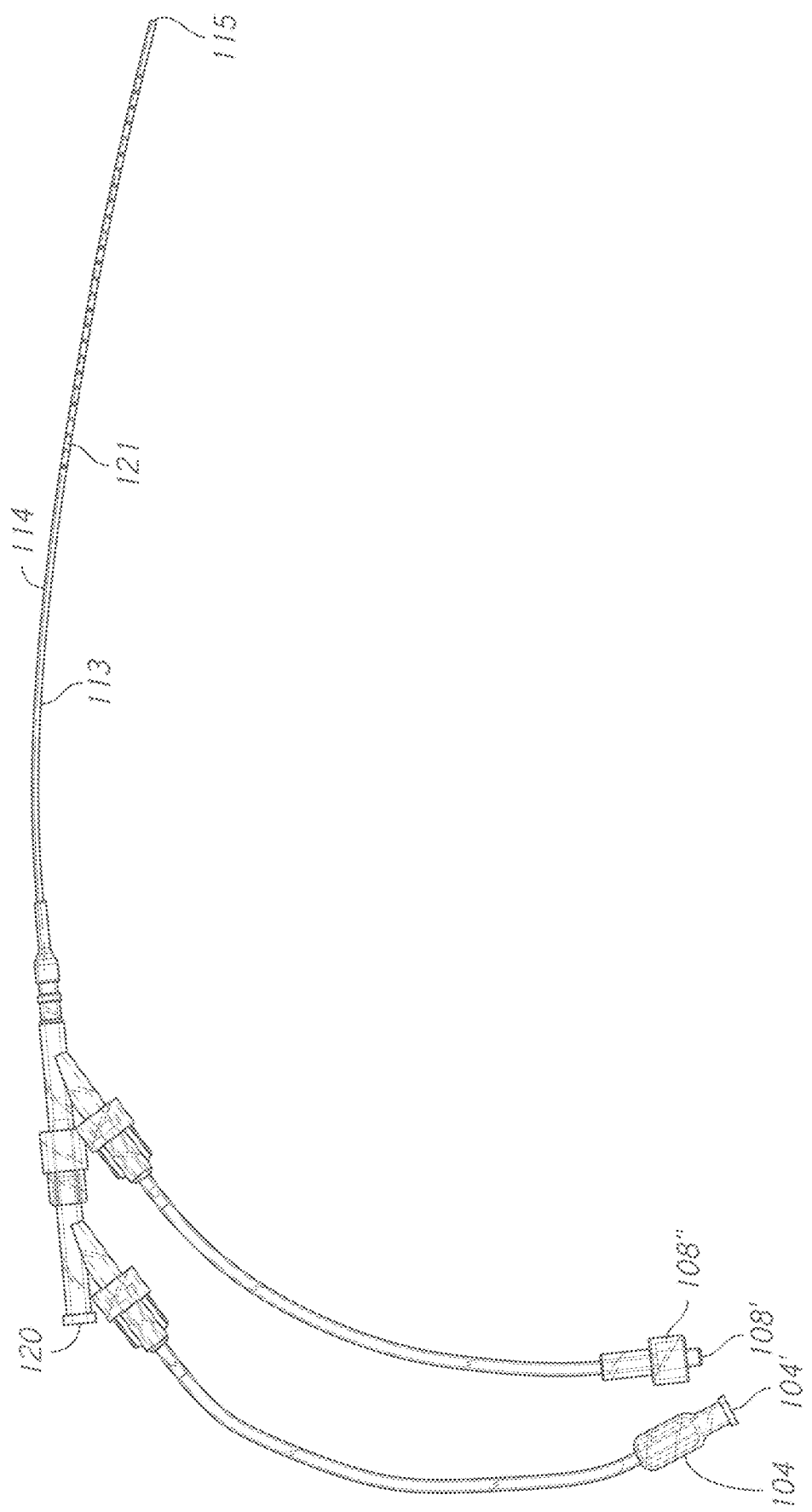
FIG. 2B is a view of a laser catheter assembly as shown in FIG. 2A.

As shown in FIGS. 2A and 2B, in some embodiments, the laser catheter assembly 101 comprises an introducer probe 113. In some embodiments, as shown in FIG. 2A, the laser catheter assembly 101 comprises one or more of an outlet arm unit 125, an outlet arm 126, and inlet arm unit 130, and an inlet arm 131. In some embodiments, the introducer probe 113 is an elongated tube that extends from a proximal introducer probe connector seal 135 (e.g., a seal, sleeve, etc.) to a sealed end 115 of the introducer probe 113.

In some embodiments, the introducer probe 113 comprises an outer tubular section 114. In some embodiments, as shown in FIGS. 2A and 2B, the outer tubular section 114 is a continuous material (e.g., a single piece molded out of a single material, a unitary structure, etc.). In some embodiments, the outer tubular section 114 is transparent or substantially transparent to certain wavelengths of electromagnetic radiation, for example, one or more of ultraviolet light, visible light, near-infrared light, far-infrared light, and/or microwave radiation.

In some embodiments, the outer tubular section 114 comprises a sealed end 115. In some embodiments, the sealed end 115 is clear, optically and/or infrared transparent, and/or substantially optically and/or infrared transparent. In some embodiments, the sealed end 115 is transparent or substantially transparent to certain wavelengths of electromagnetic radiation, for example, one or more of ultraviolet light, visible light, near-infrared light, far-infrared light, and/or microwave radiation. In some embodiments, the sealed end 115 is transmissive. In some embodiments, the sealed end 115 allows electromagnetic radiation from the laser source 203 to be transmitted through it (e.g., via a diffuser tip 204 as disclosed elsewhere herein). In some embodiments, as shown in FIG. 2A2, the sealed end 115 is shaped to distribute light from the optical fiber 202 in line with the introducer probe 113, in a conical distribution 140 expanding outwardly and distally from the sealed end 115, or in a semi-spherical distribution 141 expanding outwardly and distally from the sealed end 115. In some embodiments, the distribution of light (conically or semi-spherically) is diffused such that, within the distribution, the amount of radiation at a given distance is substantially or approximately of the same intensity (e.g., at points 140A and 140B and/or at points 141C and 141D. In some embodiments, the end 115 is configured to allow radiation and/or light to pass through it without substantially absorbing it.

In some embodiments, the optical fiber tip 204 is configured to inhibit the passage of radiation through the tip and/or the optical fiber tip 204 substantially blocks radiation. In some embodiments, the diffuser tip 223 is configured to emit a majority and/or substantially all and/or all of the radiation received via the radiation source laterally (e.g., sideways from the diffuser tip) and not along the path of the optical fiber 202 (e.g., through the optical fiber tip 204). In some embodiments, a diffusive tip that emits radiation laterally (e.g., to the sides) advantageously allows the treatment of tissues adjacent to the diffuser tip 223. In some embodiments, this configuration prevents and/or lowers the amount of heating and/or of irradiation of tissue directly in front of the fiber tip 204.

In some embodiments, as noted elsewhere herein, the diffuser tip 223 is configured to distribute electromagnetic radiation laterally from the introducer probe. In some embodiments, the intensity of electromagnetic radiation from the diffuser is approximately or substantially equal at equal distances from the diffuser tip 223. In some embodiments, light emitted from the introducer probe 113 is distributed and/or not focused. In some embodiments, light emitted from the introducer probe 113 is distributed substantially evenly. In some embodiments, because light is distributed from the diffuser along the surface of the diffuser, the radiation emitted does not cause shadows (e.g., places where the radiation is blocked by a component of the laser catheter, etc.). In some embodiments, the laser catheter assembly and/or the diffuser tip lacks a focusing lens and does not comprise a mirror.

In some embodiments, the sealed end is domed (e.g., hemispherical, having the shape of a hemisphere, semi-spherical, dome-shaped, etc.). In some embodiments, as described elsewhere herein, the sealed-end is transmissive. In some embodiments, transmissive means allowing all, substantially all, or part of the electromagnetic radiation from the diffuser tip 223 to pass. In some embodiments, the outer tubular section 114 is continuous with the sealed end 115 (e.g., the sealed end and the outer tubular section are a single piece molded out of a single material, a unitary structure, etc.). In some embodiments, the transmissive sealed end 115 has the benefit of reducing the build-up of heat in the tip of the probe. This feature helps avoid melting of the probe and also allows the laser to be distributed into tissue along the direction of the probe. In some embodiments, the sealed end is not cone-shaped and/or not a ground material (e.g., a scattering material, an opaque or substantially opaque material, etc.). In some embodiments, it has been found that round and/or cone configurations do not allow radiation to pass through the introducer probe. In some embodiments, it has been found ground and/or conical configurations can concentrate radiation causing hot spots and heating that can lead to warping and/or charring of a probe and/or burning of tissue around the probe.

In some embodiments, the domed tip is prepared using radio frequency. In some embodiments, the domed tip is formed from a nylon extrusion, which is placed over a mandrel, and then inserted into a stainless steel die. In some embodiments, the die is heated with RF energy, while the extrusion is simultaneously pushed into the cavity using pneumatically-actuated grippers, which causes the tip of the extrusion to be reflowed/reshaped over the end of the mandrel." In some embodiments, the RF machine is set with temperature, pressure, and time settings that are specific to extrusion so it can produce very repeatable tips. In some embodiments, the tip is not hemispherically shaped, but is another shape that allows the passage of radiation without substantial build-up of heat or concentration of radiation (e.g., a rounded cubical end shape, a cubical end shape, a rounded cylinder end shape, a cylinder end shape, etc.).

In some embodiments, as shown in FIG. 2A1, the outer tubular section 114 comprises a lumen 116 (e.g., a first lumen). In some embodiments, an internal tube 117 resides within the first lumen 116. In some embodiments, the internal tube 117 comprises a second lumen 118.

In some embodiments, as shown in FIG. 2A and FIG. 2B, the laser catheter assembly 101 is configured to receive coolant via the coolant inlet connector 104, though a catheter inlet conduit 132, through the inlet arm unit 131, and into a body of the inlet arm unit 130. The coolant then travels via the internal tube 117, to the open pool 119, through the first lumen 116, through the outlet arm unit 125, through the outlet arm, into the catheter outlet conduit, and out via the coolant outlet connector 108. In other words, in some embodiments, one or more of the coolant inlet connector 104, the catheter inlet conduit 132, the inlet arm unit 131, the inlet arm unit 130, the internal tube 117, the open pool 119, the first lumen 116, the outlet arm unit 125, the outlet arm, the catheter outlet conduit, and/or the coolant outlet connector 108 are in fluidic communication.

In some embodiments, the introducer probe 113 extends from a proximal end to a distal end, the sealed domed end 115 of the outer tubular section 114 being located at the distal end. In some embodiments, the internal tube 117 terminates a distance away from the sealed domed end 115 leaving an open pool 119 at the distal end of the introducer probe 113. In some embodiments, when the optical fiber is positioned in the introducer probe 113, the terminal end of the diffuser tip 223 terminates at or approximately at the distal end of the internal tube 117. In some embodiments, a portion of the diffuser tip 223 protrudes from the internal tube 117 in the open pool 119. In some embodiments, this protrusion allows a more concentrated amount of electromagnetic radiation to penetrate the sealed end 115 of the introducer probe 113. In some embodiments, the open pool provides an area around which coolant can flow without substantial restriction by the fiber tip 204 (e.g., blocking and/or restricting coolant flow within the lumens).

In some embodiments, as shown in FIG. 1, the laser catheter assembly 101 is configured to receive the optical fiber 202 into the introducer probe 113 via an end aperture 120. In some embodiments, the internal tube 117 is configured to receive the optical fiber 202 within the second lumen 118. In some embodiments, the optical fiber connector 222 couples with features on the end aperture 120 to provide a fluid-tight seal. In some embodiments, the coupling fixes the diffuser tip 223 in a position within the introducer probe 113. In some embodiments, the laser catheter assembly 101 receives only one optical fiber 202 and the introducer probe 113 and internal tube 117 is sized and/or configured to receive only a single optical fiber tip 204 and/or diffuser tip 223.

In some embodiments, as noted elsewhere herein, the second lumen 118 is in fluidic communication with the coolant inlet connector 104. In some embodiments, as noted elsewhere herein, the first lumen 116 is in fluidic communication with the coolant outlet connector 108. In some embodiments, when the optical fiber 202 is positioned within the second lumen 118, the laser catheter assembly is configured to allow the passage of a coolant from the coolant inlet connector 104 through the second lumen 118 into the first lumen 116 and out of the coolant outlet connector 312.

In some embodiments, the lumen of the laser catheter assembly 101 introducer probe 113 can be formed from a material such as nylon, PA12 nylon, or a similar material. In some embodiments, PA12 nylon, as opposed to a material such as polycarbonate, advantageously smooths the introducer probe's 113 passage through introducers and tissue.

In some embodiments, as shown in FIG. 2A, the introducer probe 113 comprises printed "hash" marks 121. In some embodiments, the introducer probe 113 is graduated. In some embodiments, hash marks and/or graduations can clearly mark the depth of penetration of the probe into tissue (and/or the distance the probe has been withdrawn from tissue). In some embodiments, the hash marks are distanced equal to or less than: about 4 mm apart, about 8 mm apart, about 12 mm apart, values between the aforementioned values, or ranges spanning and/or including those values. In some embodiments, alternating hash marks and dots at intervals permit the pullback of the laser catheter assembly 101 through tissue for multiple treatments with various optical diffusers (e.g., 1 cm diffusers, 1.8 cm diffusers, etc.), as discussed elsewhere herein. In some embodiments, these graduations and/or hash marks allow the probe depth to be visualized directly by a user. In some embodiments, these graduations and/or hash marks allow for fine control of the location of the probe allowing effective and/or controlled ablation of tissue. In some embodiments, the introducer probe is of a length equal to or less than about: 50 cm, 30 cm, 20 cm, 10 cm, values between the aforementioned values, or ranges including and/or spanning those values.

In some embodiments, the optical fiber 202 comprises a diffuser tip. In some embodiments, the diffuser tip 223 is a portion of the optical fiber 202 having radiation scattering features (e.g., topography, bumps, roughenings, dimples, etc.) that encourage and/or allow the radiation (e.g., laser light, photons, radiation) to exit the optical tip in different directions (e.g., scatter, diffuse, etc.). In some embodiments, these features are provided as a gradient along the diffuser and are less dense closer to the laser source 203 and denser farther from the laser source 203. In some embodiments, the density gradient encourages a substantially even distribution of radiation along the entire diffuser tip. In some embodiments, the diffusive portion 223 of the optical fiber 202 may be of different lengths. In some embodiments, the diffusive portion of the optical fiber may be of a length equal to or less than about: 50 mm, 30 mm, 18 mm, 10 mm, values between the aforementioned values, or ranges including and/or spanning those values. In some embodiments, the longer diffuser permits the treatment of larger tumor volumes in the same amount of time by using a higher laser power and distributing it along a longer diffuser. In some embodiments, using the smaller diffusive tip allows less laser power to be used and allows treatment of smaller sized tumors with greater specificity. In some embodiments, a single treatment can use various sizes of diffusers to tailor treatment to specific areas of the body and towards specific tumor dimensions. In some embodiments, as shown in FIG. 3B, the optical fiber is supple and/or flexible and is configured to move within the introducer probe without kinking or cracking. In some embodiments, the optical fiber has a length sufficient to allow the laser source to be placed out of the way during an operation. In some embodiments, the length of the optical fiber is that is equal to or less than: 1 m, 2 m, 3 m, 5 m, or ranges including and/or spanning the aforementioned values.

To illustrate one or more improvements achieved using design features of the disclosed laser catheter assembly, the following exemplary illustration is provided. In some embodiments, hash marks located along the introducer probe enable a user to determine the location of the laser catheter diffuser tip and the extent of treatment to a tumor being targeted. In some embodiments, the initial positioning of the introducer probe (e.g., depth to be inserted into the body along a z-axis and lateral positioning along the x and y axes) can be determined using Computer Tomography. Once the initial position is reached, the hash marks can be used to pinpoint treatment locations. The probe can be withdrawn from one position to the next at set spacings determined by the graduations on the probe. The printing on the laser catheter assembly provides a "depth gauge" for the user to know how far the laser catheter assembly has penetrated into tissue or how far the probe has been withdrawn from a starting position. In some embodiments, for example, 8 mm spacing between hash marks and the 8 mm spacing between "dots" halfway between the hash marks provide a 4 mm spaced "ruler" to permit accurate "pullback". In some embodiments, as described elsewhere herein, a grid is used to aid in proper positioning of the diffuser tip of the laser catheter assembly within tissue laterally. In some embodiments, as disclosed elsewhere herein, an 8 mm pullback against a 10 mm grid permit is used. These markings provide a straightforward way for the user to know how deep the laser catheter is situated in the target tumor or tissue and to provide a straightforward means of incrementally pulling back on the catheter in order to produce a contiguous zone of ablation along the catheter track.

Figure 3A:
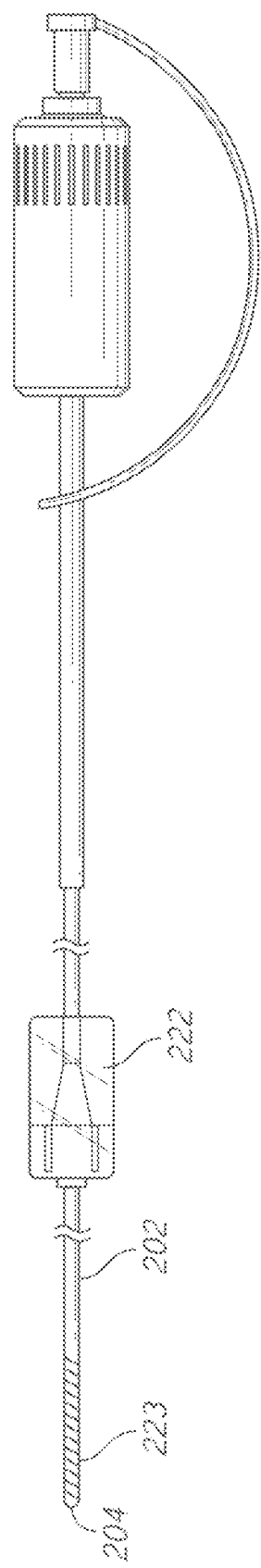
FIG. 3A illustrates an embodiment of an optical fiber that can be inserted into the laser catheter assembly of FIG. 2A.
Figure 3B:
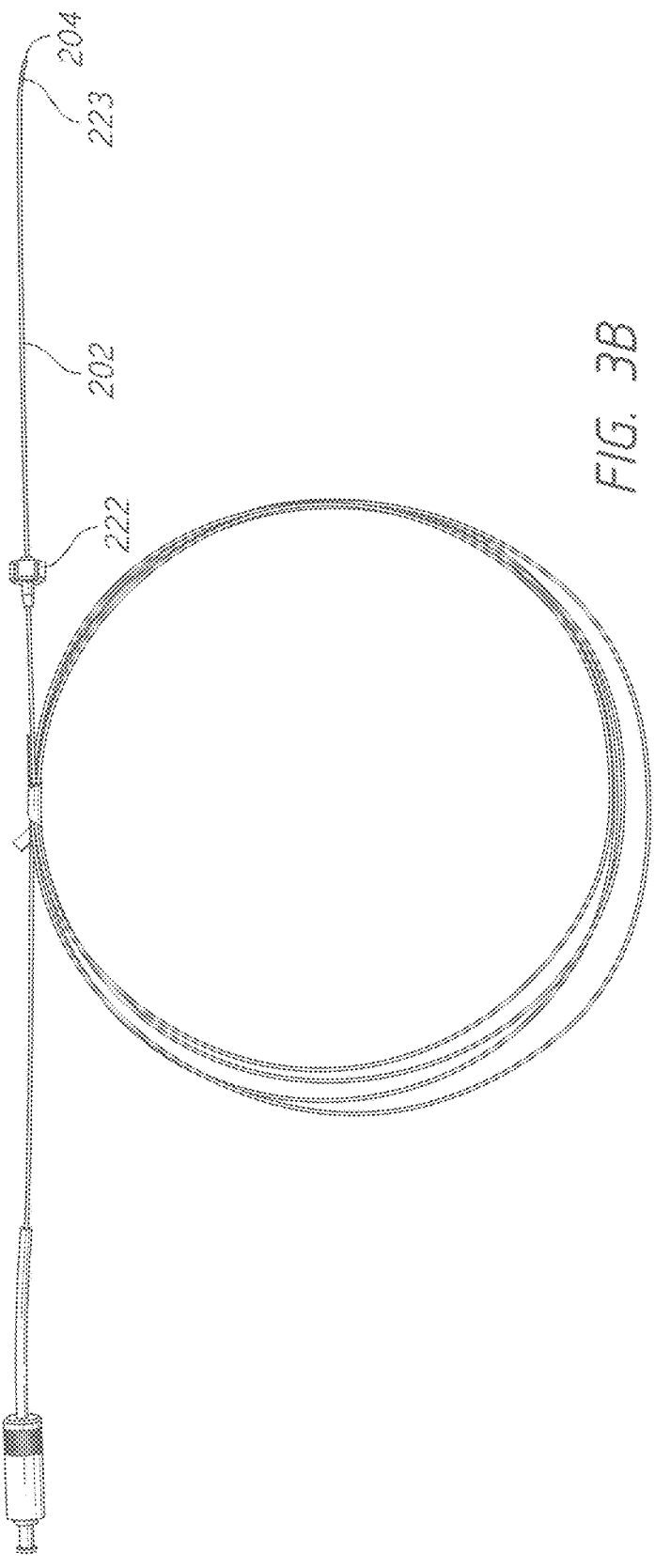
FIG. 3B is a view of an optical fiber as shown in FIG. 3A.

In some embodiments, as shown in FIGS. 3A and 3B, the optical fiber can comprise an optical fiber connector 122 (e.g., a luer connector, which in some embodiments can include an ISO 594-compliant luer taper). In some embodiments, the optical fiber connector is bonded at a fixed distance from the distal end of the optical fiber tip 204. In some embodiments, the optical fiber connector 122 is configured to engage with the end aperture 120 of the laser catheter assembly 101. In some embodiments, the fixed positioning of the optical fiber connector 122 can ensure proper setback of the diffuser tip within the laser catheter assembly 101. In some embodiments, fixing the optical fiber 202 within the laser catheter assembly 101 can help prevent melting of the tip and can ensure proper coolant flow around the diffuser. In some embodiments, fixing the optical fiber can help prevent the diffuser tip from sliding out of the laser catheter assembly 101. In some embodiments, fixing the optical fiber 202 within the laser catheter assembly 101 can help ensure that the laser diffuses properly out of the diffuser tip (e.g., by preventing a portion of the diffuser from exiting the inner internal tube 117 or preventing the diffuser from bottoming out against the probe 113 tip where it could, for example, occlude the flow of coolant and/or cause uneven distribution of light emitted). In some embodiments, fixing the fiber can also advantageously provide sufficient diffusion of light from the tip of the introducer probe 113 allowing treatment of the tissue in front of the tip (in addition to tissue laterally adjacent to the diffuser tip).

In some embodiments, the optical fiber has a total length in meters of less than or equal to about: 2, 3.5, 5, or ranges including and/or spanning the aforementioned values. This length advantageously lessens clutter in the operating room given that, in some embodiments, the entire laser illuminating system as disclosed herein can be of a size that allows it to be housed entirely in the operating room (e.g., in a sterile environment).

In some embodiments, the coolant supply system of the laser illuminating system 100 comprises the coolant reservoir 305, the coolant inlet conduit 306, and the coolant pump 307. In some embodiments, the coolant supply system supplies coolant (e.g., saline, water, etc.) to the laser catheter assembly 101. In some embodiments, the coolant helps prevent early onset of photocoagulation adjacent to the laser catheter assembly 101 introducer probe 113. Early onset photocoagulation could detrimentally limit light penetration of laser radiation into tissue and/or nullify the tumor specificity of the optically excited nanoparticles.

Figure 4:
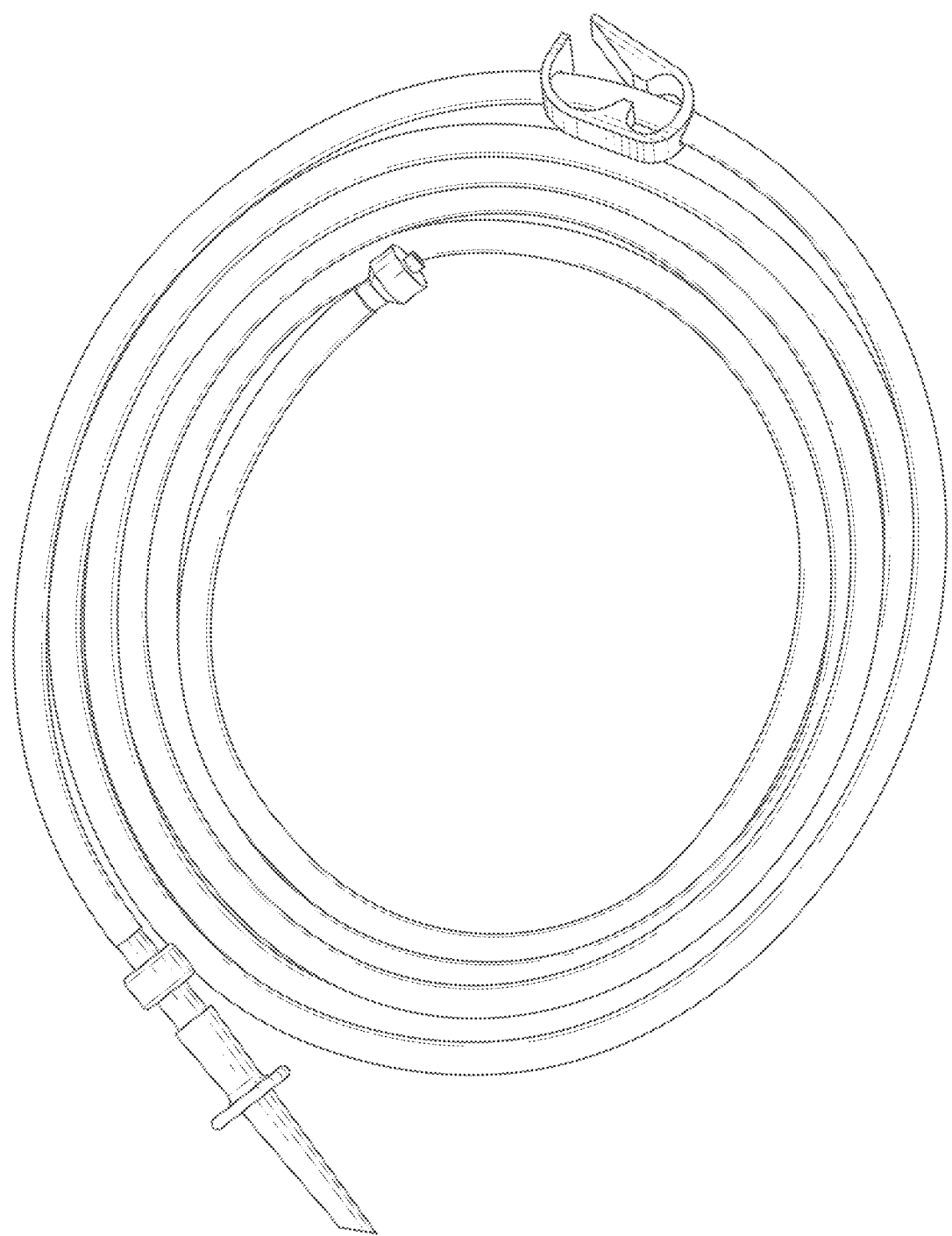
FIG. 4 is a view of an embodiment of a coolant inlet conduit.
Figure 5A:
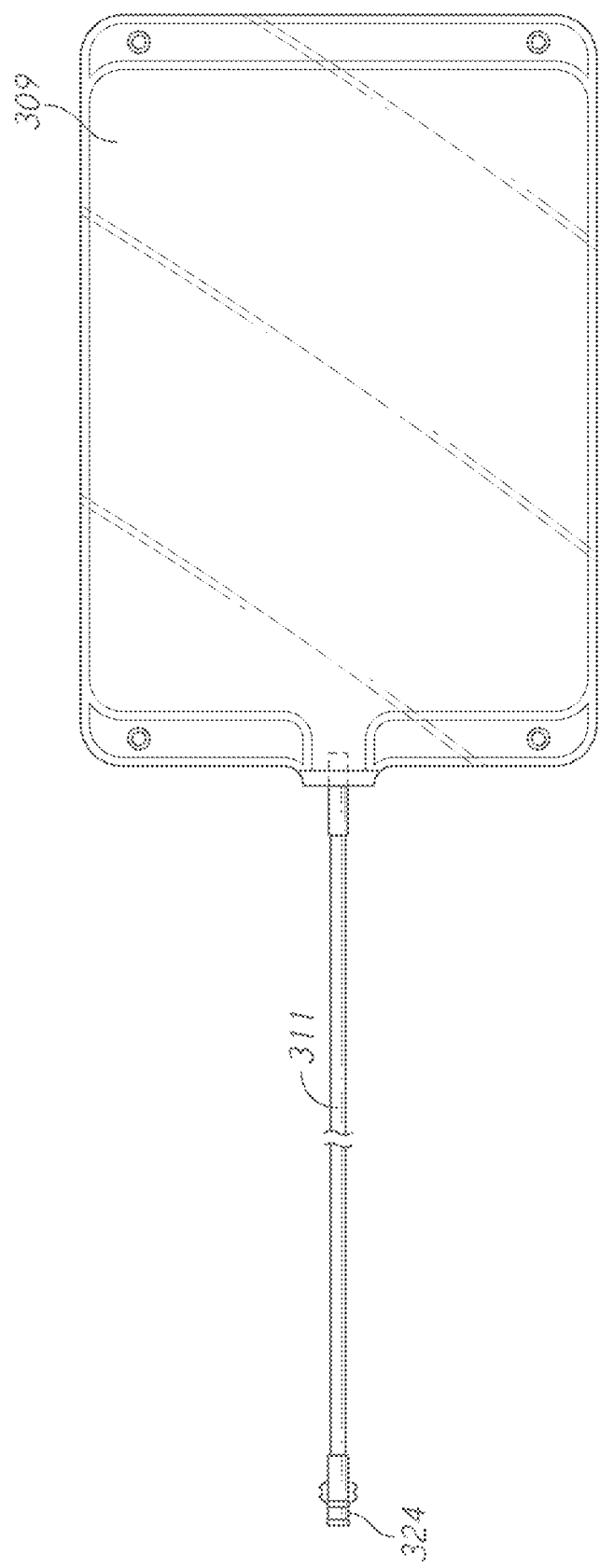
FIG. 5A illustrates an embodiment of a coolant recovery bag.
Figure 5B:
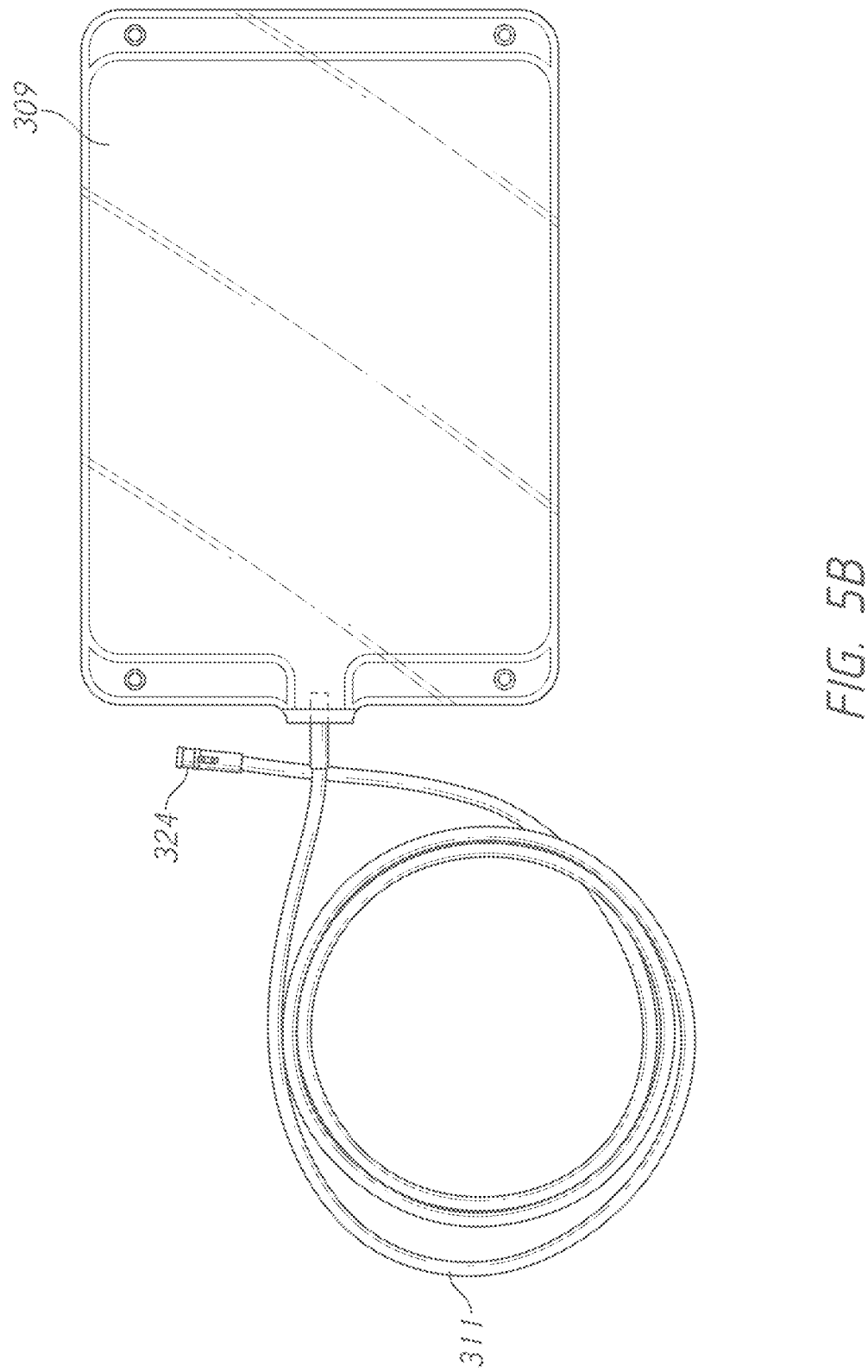
FIG. 5B is a view of a coolant recovery bag as shown in FIG. 5A.

FIG. 4 shows an embodiment of coolant inlet conduit 306. In some embodiments, the length of the coolant inlet conduit 306 can be less than or equal to: about 3 m, about 4 m, about 5 m, about 10 m, values between the aforementioned values, or ranges spanning and/or including those values. In some embodiments, the length of the coolant inlet conduit 306 reduces clutter in the operating setting. In some embodiments, the coolant inlet conduit 306 is composed of flexible Tygon tubing (polyvinyl chloride tubing or the like, e.g., a flexible tubing) enabling it to be clamped into the cooling pump at any location along its length. In some embodiments, the tubing is about ⅛" in diameter. In some embodiments, the diameter of the tubing is less than about: 1/12", ⅛", ¼", or ranges including and/or spanning the aforementioned values. In some embodiments, this diameter permits a smaller pump head spacing, greater control of coolant flow rate, and/or greater consistency of flow rate between tubing sets. In some embodiments, this feature removes the need for an external flow restrictor and meter in the return line. In some embodiments, this feature permits greater precision in controlling the low flow (e.g., equal to or less than about 8 mL/min) coolant flow used during certain methods described herein. In some embodiments, the flow rate in mL/min that can be achieved is less than or equal to 2, 4, 8, 10, or ranges including and/or spanning the aforementioned values. FIGS. 5A and 5B show an embodiment of a coolant recovery bag. As shown in FIG. 5B, the coolant recovery bag can comprise a flexible length of tubing configured to attach to the laser catheter assembly.

In some embodiments, the coolant supply set design disclosed herein advantageously eliminates or reduces the problem of not being able to position a coolant pump relative to a reservoir that supplies the coolant. In some embodiments, the coolant supply system can be fabricated with a continuous length of tubing, thereby reducing the part count and complexity. In some embodiments, the use of polyvinyl chloride tubing of the internal diameters disclosed herein advantageously allows controlling the low flow (e.g., 8 mL/min) coolant flow.

In some embodiments, the coolant pump 307 has a flow rate adjuster that can be calibrated to default to a given speed in order to produce a given flow rate. In some embodiments, the pump is a peristaltic pump (e.g., Langer BT100-1L). In some embodiments, the pump delivers flow rates in mL/min of less than or equal to about: 0.002, 0.01, 0.1, 1, 20, 50, 100, 500, or ranges including and/or spanning the aforementioned values. In some embodiments, the coolant pump 307 has quiet operation features and operates at decibel levels equal to or less than about: 10, 20, 30, 40, 50, 60, 70, 80, or ranges including and/or spanning the aforementioned values. In some embodiments, the quiet features of this pump are beneficial because the disclosed system can be placed in an operating room with the patient.

In some embodiments, the pump 307 can be connected an actuating device (e.g., a footswitch, pedal, panel, button). In some embodiments, the actuating device can be turned on or off by a user (e.g., a physician or technician operating the pump). In some embodiments, the laser source is connected to an actuating device (e.g., a footswitch, pedal, panel, button) that can be the same or different from the actuating device that controls the pump. In some embodiments, where the actuating device of the pump and the laser source is the same, the actuating device can have one or more toggle switches (e.g., buttons or panels) that allow the user to control the flow of coolant through the laser catheter and/or to control the emission of laser by the laser source separately or simultaneously. In some embodiments, where the laser source and the pump are to be activated simultaneously, the actuating device can have a single switch for turning both the laser source and the pump on or off simultaneously. In some embodiments, where the laser source and the pump are to be activated separately, the actuator can have different switches to activate one device at a time.

In some embodiments, the actuator connection allows coolant flow when the laser is active and stops coolant flow when inactive. In some embodiments, in addition to reducing the volume of coolant consumed (e.g., the number of coolant bag changes, etc.), this feature can advantageously prevent pre-cooling of the tissue between laser treatments. In some embodiments, the pump is programmable to have a default flow rate when the laser is in operation. In some embodiments, control of the default flow rate of the pump is helpful for the disclosed methods which can use of a nominally sub-ablative laser dose without using real-time temperature monitoring. In some embodiments, the default flow rate in mL/min is less than or equal to about: 0.002, 0.01, 0.1, 1, 5, or ranges including and/or spanning the aforementioned values. The predetermined flow rate allows the user to remove heat at a pre-determined rate. In some embodiments, the automatic stopping of coolant flow when the laser is off helps avoid chilling tissue. Flowing coolant through the laser catheter assembly between laser treatments (e.g., when the laser is off) chills the surrounding tissue (e.g., from at or around 30-37° C.) to the temperature of the coolant (e.g., at or around 21-23° C.). In some embodiments, this has the effect of producing under-treatment because of the additional temperature gradient that must be overcome in order to produce tissue ablation. In some embodiments, combinations of the disclosed features allow the cooling to be tightly regulated. In some embodiments, this temperature control can advantageously delay tissue coagulation adjacent to the laser catheter until the end of the timed treatment.

In some embodiments, since the increase in optical scatter that arises from coagulation effectively attenuates optical penetration into tissue, the delay of photocoagulation is can aid in treating tumor tissue at longer distances from the laser catheter since nanoparticles are activated only by optical photons.

In some embodiments, the coolant recovery bag 309 collects the coolant after a single pass through the laser catheter assembly 101. In some embodiments, the coolant recovery bag 309 is connected to the laser catheter assembly 101 via a coolant outlet conduit 311 and an outlet conduit connector 324 (see FIGS. 5A-B). In some embodiments, the coolant recovery bag 309 volume is greater than or equal to about 1.5 liters, 2.0 liters, or 3 liters. In some embodiments, this volume allows for the collection throughout the duration of treatment. In some embodiments the treatment duration is equal to or at least about 62 standard 3-minute treatments at 8 mL/min using the footswitch activated pump. In some embodiments, the coolant recovery bag 309 has an integrated 1.5 meter tubing set, which permits it to be placed at the bedside.

In some embodiments, the laser catheter assembly is introduced into a tumor or an organ comprising tumor tissue using a trocar assembly 400 comprising a trocar 425 with a sleeve catheter 426 (a catheter sheath) sheathed around the trocar 425. As shown, in FIG. 2B, in some embodiments, the introducer probe 113 is supple and/or flexible (e.g., a 25 cm length of probe can be looped into a circle without kinking). In some embodiments, the tip is comprised of a material that allows flexing which advantageously allows the tip to around obstructions at tissues. In some embodiments, as disclosed elsewhere herein, the flexible material of the probe advantageously is resistant to adhesion to tissue and/or is non-stick and/or is substantially non-stick. In some embodiments, the introducer probe 113 has a length (e.g., from the proximal to distal end) of less than or equal to about: 300 mm, 240 mm, 200 mm, or ranges including and/or spanning the aforementioned values. In some embodiments, the introducer probe has a width of less than or equal to about: 2 mm, 1 mm, 0.5 mm or ranges including and/or spanning the aforementioned values.

In some embodiments, to facilitate introduction of the introducer probe 113, the introducer probe 113 is inserted into tissue using a trocar sleeve assembly 427 as shown in FIG. 6A-6A2. In some embodiments, as shown in FIG. 6A, the trocar sleeve assembly 427 can comprise the trocar 425 and the sleeve catheter 426. In some embodiments, the trocar 425 comprises a trocar lumen 428. FIG. 6A1 shows a bisected view of the trocar assembly 400 with the lumen 428 exposed. FIG. 6A4 shows an end on view of the catheter sleeve assembly 427. FIGS. 6B and 6B1 show the trocar 425 without the sleeve, where FIG. 6B1 shows a bisected view. In some embodiments, the trocar 425 also comprises a trocar handle 429, as shown. In some embodiments, the trocar handle 429 is ergonomic. In some embodiments, the trocar handle 429 has one or more finger holds 431 that facilitate manipulation of the trocar 425 during placement. In some embodiments, a trocar handle 429 allows placement of the trocar through tissues of the patient and/or positioning of the trocar assembly 427 inside the patient at the site of treatment.

In some embodiments, the trocar 425 comprises a three-sided cannula and/or needle 430. FIG. 6A3 shows an expanded view of the catheter tip 430 with the sheath 426. FIG. 6B2 shows an expanded view of the catheter tip 430 without the sheath 426. FIG. 6B3 shows a front view of the trocar tip 430. In some embodiments, the three-sided trocar tip 430 avoids tissue pull as the trocar is pushed through tissue of a patient. In some embodiments, beveled needles can pull to a side of the bevel as you pass through tissue. In other embodiments, a beveled needle is used as a trocar (not pictured). FIG. 6B4 shows an end view of the trocar 429.

In some embodiments, after insertion into a site of treatment, the trocar 425 is removed from the patient's body. In some embodiments, in removing the trocar 425 the catheter sheath 426 is left inside the patient. In some embodiments, the catheter sheath 426 can then be used to position the laser catheter assembly 101 introducer probe 113 into the site of treatment.

Figure 7A:
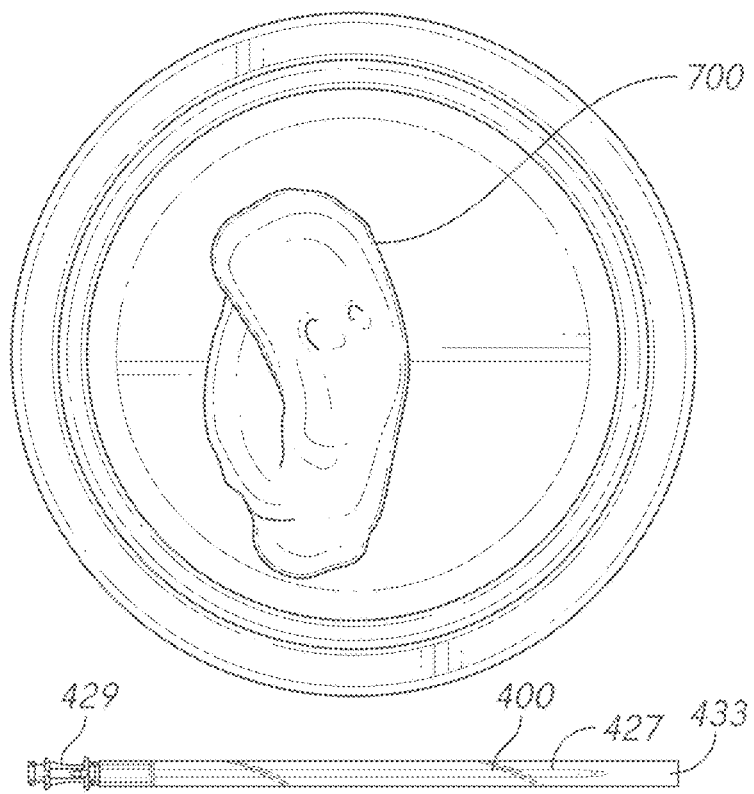
Figure 7B:
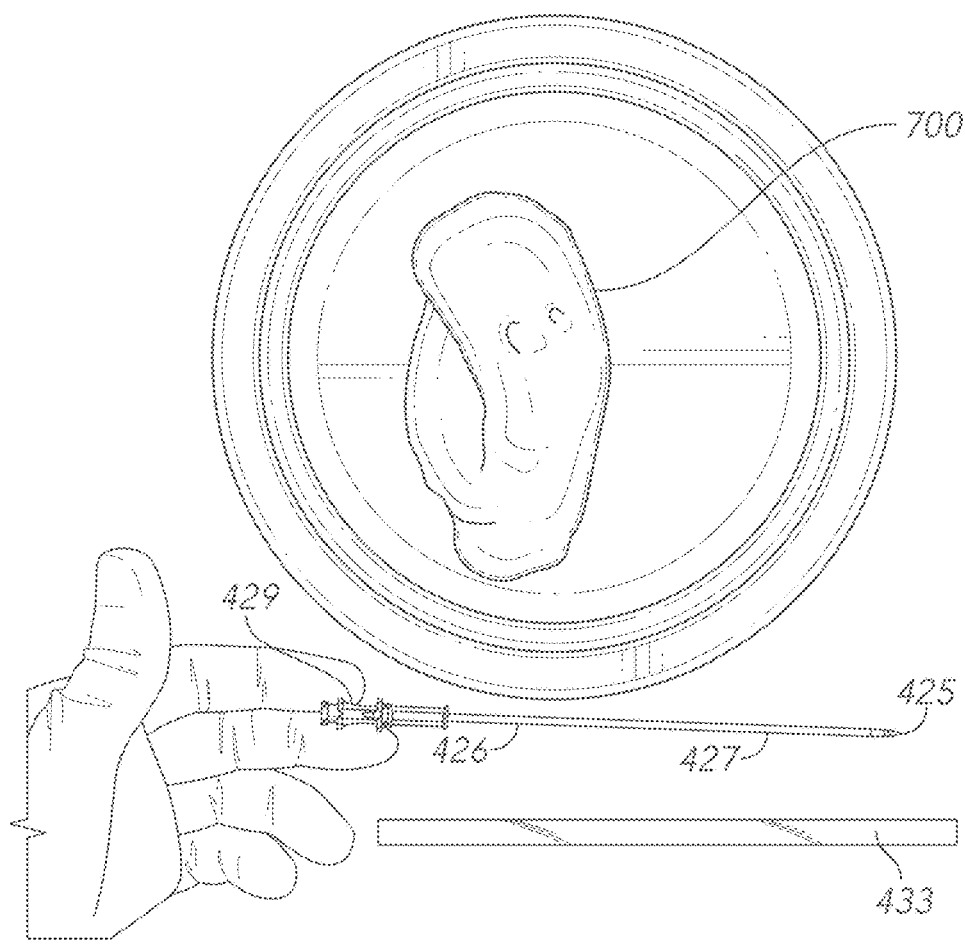
Figure 7C:
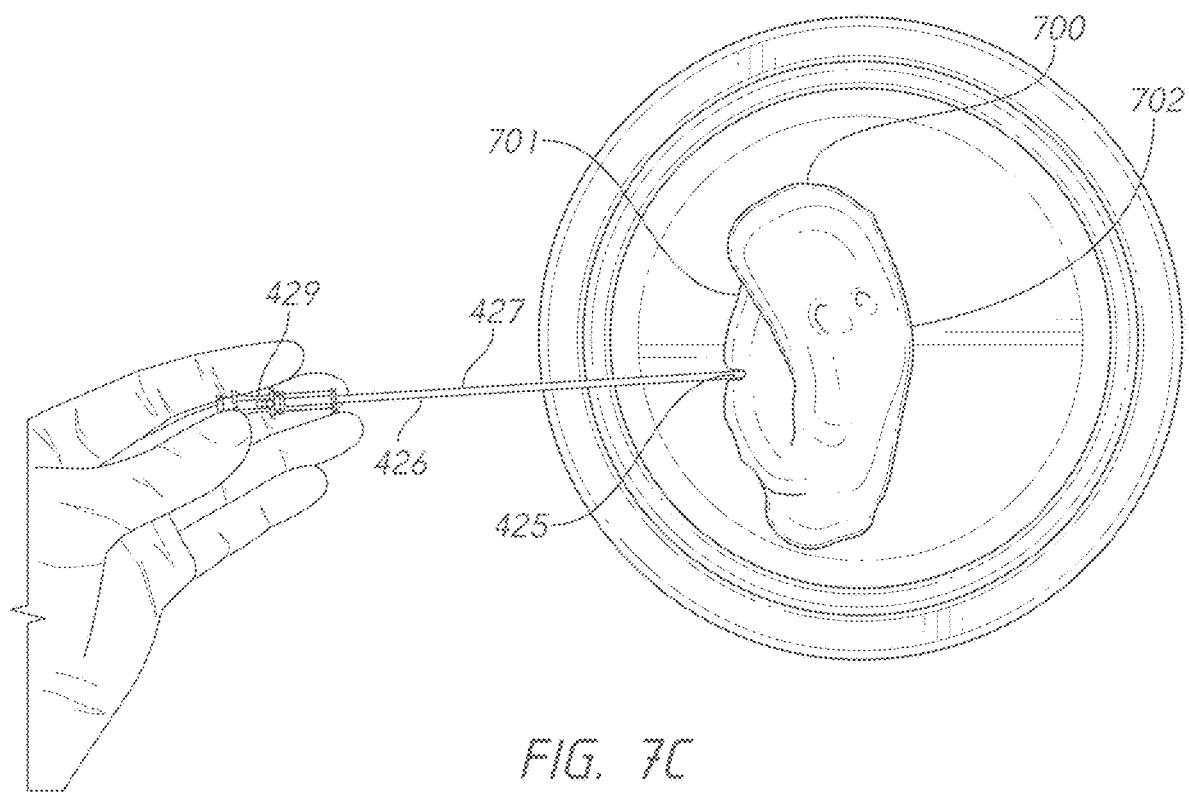
Figure 7D:
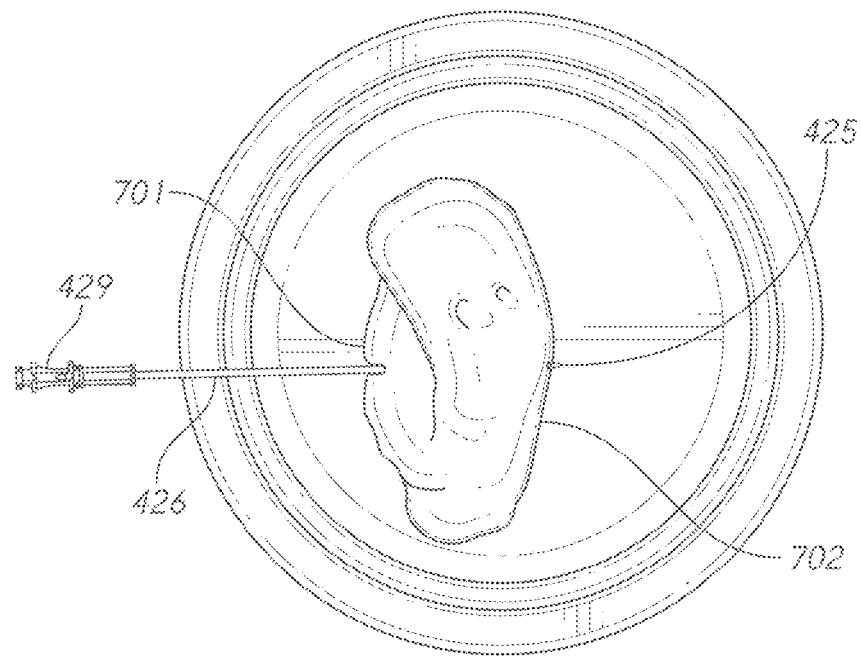

In some embodiments, the methods disclosed herein comprise inserting a trocar assembly 427 comprising a trocar 426 and a catheter sheath 426 sheathed around the trocar 426 into a patient at an insertion point (e.g., a first insertion point). Such an insertion is illustrated in the drawings of FIGS. 7A-J using a test specimen 700 representing a target tissue (e.g., a tumor, etc.). In this case, the test specimen is a raw chicken breast. The test specimen is used as a model for a tumor or for an organ comprising a tumor. FIG. 7A shows the test specimen and a trocar sleeve assembly 427 within a protective cover 433. FIG. 7B shows the trocar sleeve assembly 427 removed from the protective cover 433. As shown in FIG. 7C, in some embodiments, the trocar sleeve assembly 427 can be inserted into a proximal side 701 (where proximal is in reference to the position of the user and/or the insertion point) of the target tissue (e.g., the test specimen 700). In some embodiments, as shown in FIG. 7D, the trocar sleeve assembly 427 is inserted through the body of the target tissue to a distal side 702 or substantially distal side of the target tissue 700. In some embodiments, the trocar sleeve assembly can be placed at a position intermediate of the proximal and distal side of the target tissue. In FIG. 7D, the trocar 425 is visible at the distal side 702 of the target tissue.

Figure 7E:
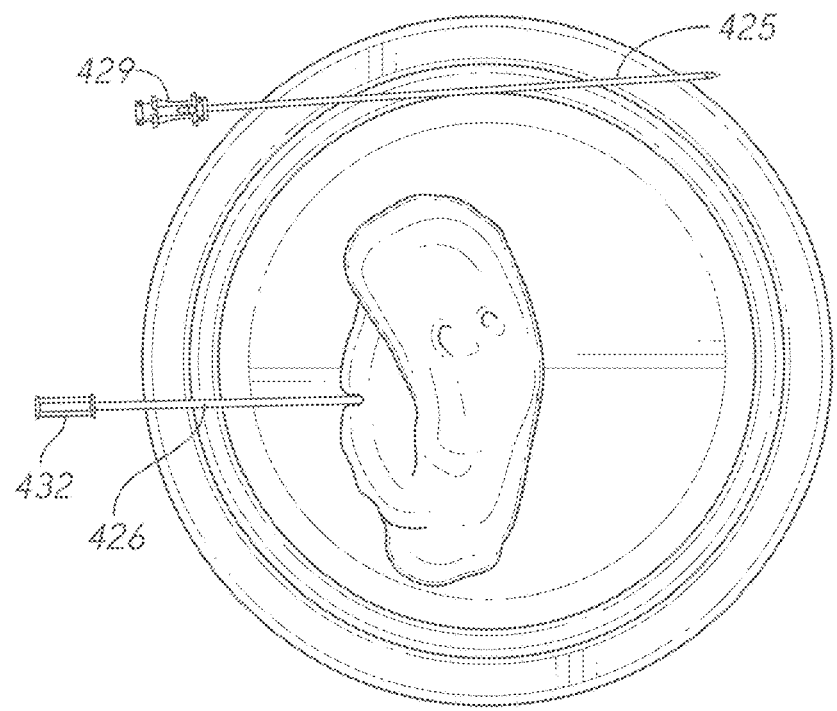

As shown in FIG. 7E, in some embodiments, once the trocar catheter assembly has reached the distal side of the target tissue 702, the trocar 425 can be removed leaving the catheter sheath 426 in place. In some embodiments, proper positioning of the trocar sleeve assembly 427 can be accomplished using MRI, ultrasound, or other real time imaging methods (e.g., Computer Tomography).

Figure 7F:
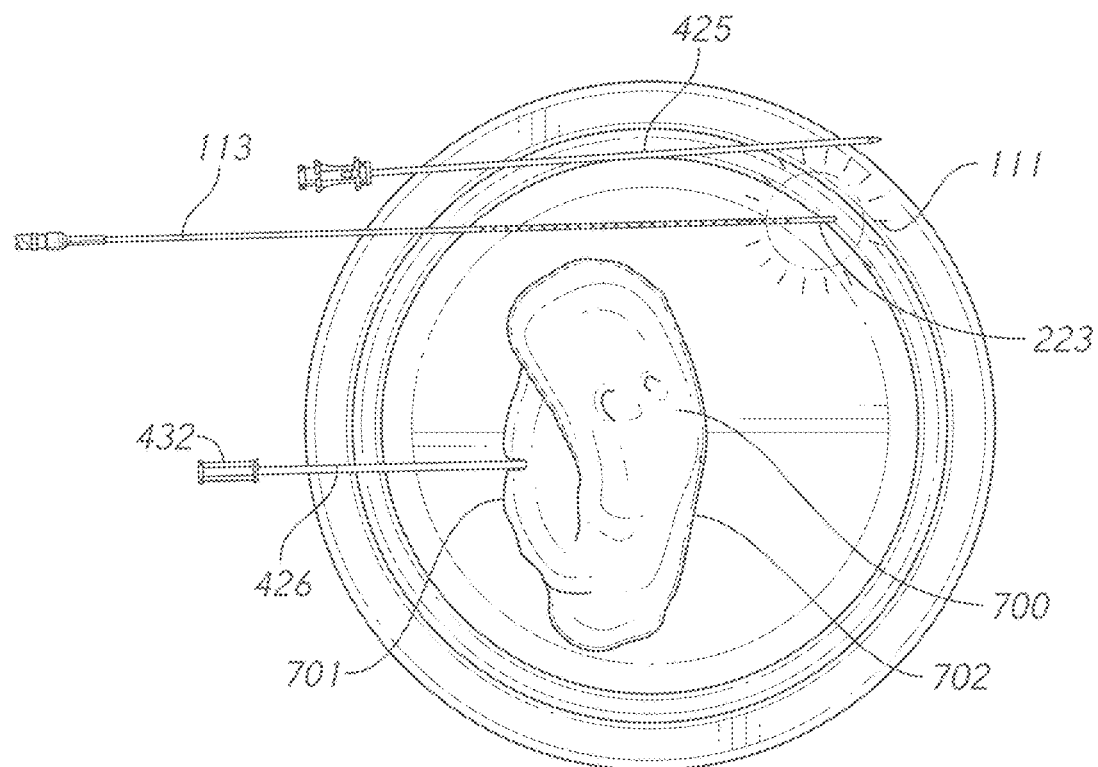

In some embodiments, as shown in FIG. 7F, the introducer probe 113 of the laser catheter assembly 101 can be prepared for insertion into the catheter sheath. As shown, a radius of irradiation 111 is present around the diffuser tip when the laser is activated. In some embodiments, prior to insertion of the introducer probe 113 into the catheter sheath 426, the optical fiber 202 is positioned inside the laser catheter assembly 101. In some embodiments, the optical fiber 202 is fixed in the laser catheter assembly 101 via engagement of the optical fiber connector 222 with the end aperture 220.

Figure 7G:
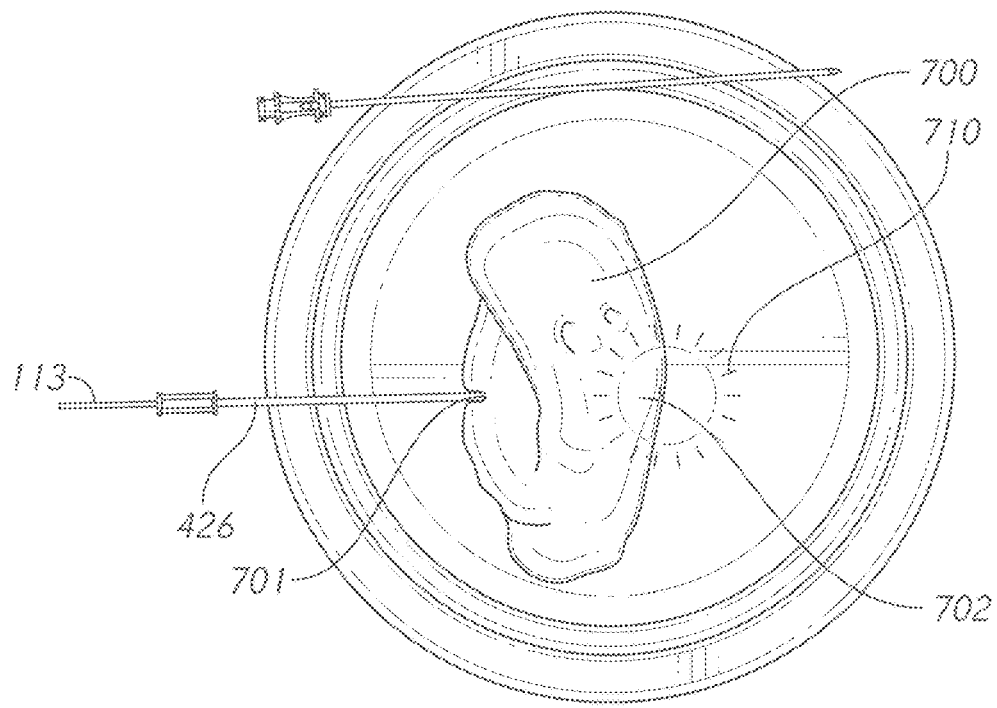
Figure 7H:
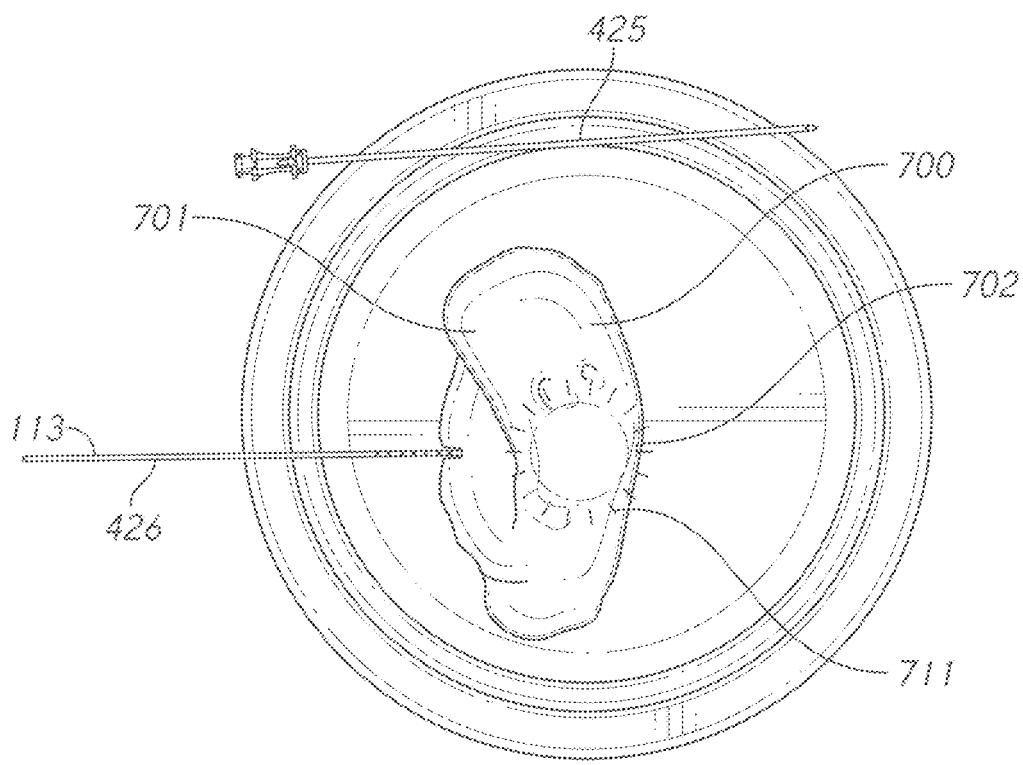

In some embodiments, as shown in FIG. 7G, the introducer probe 113 of the laser catheter assembly 101 can be inserted into the catheter sheath 426. In some embodiments, the catheter sheath 426 comprises an insertion port 432 that facilitates insertion of instruments, such as the introducer probe 113. In some embodiments, after the introducer probe 113 reaches the proper position in the target tissue, the sheath 426 can be withdrawn slightly towards the proximal side of the target tissue 700 exposing the introducer probe 113 and/or the diffuser tip 223. In some embodiments, where the catheter sheath is transparent to the radiation emitted by the laser source, the catheter sheath need not be withdrawn to expose the introducer probe 113. In some embodiments, the graduations of the introducer probe are visible through the catheter sheath 426 to allow depth of insertion into the patient to be easily visualized during a procedure.

Figure 7I:
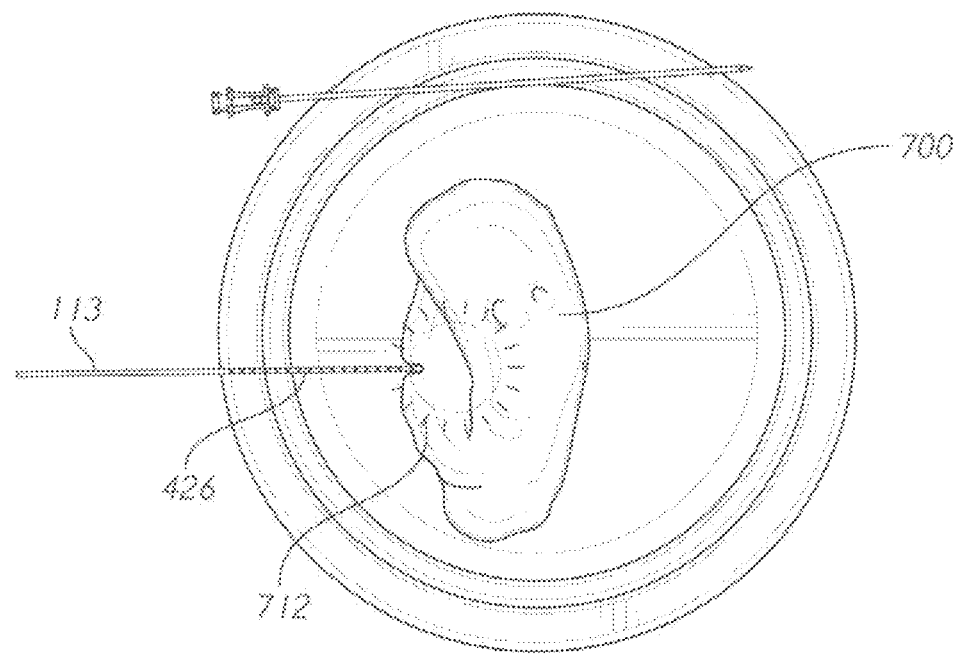

As shown in FIG. 7G, the laser source can be activated to illuminate the diffuser tip 223 creating an irradiated region 710 of the target tissue 700. This first region is irradiated for a defined period of time at which point, the catheter sheath 426 and introducer probe 113 can be withdrawn slightly towards the proximal side 701 and away from the distal side 702 of the target tissue 700 exposing a second region (a second irradiated region 712) of the target tissue to treatment. In some embodiments, the withdraw/irradiate process can be repeated multiple times depending on the size of the target tissue. As shown in FIG. 7I, in some embodiments, a third region (third irradiate position 712) can be irradiated, and so on. In some embodiments, the hash marks 121 of the laser catheter assembly 101 allow the user to determine the proper position for the first, second, third, fourth, etc. regions for irradiation as the introducer probe 113 is withdrawn.

In some embodiments, the introducer probe 113 and/or the introducer probe and the catheter sheath 426 are withdrawn from the target tissue incrementally at distances of equal to or less than: about 4 mm, about 8 mm, about 12 mm, values between the aforementioned values, or ranges spanning and/or including those values. In some embodiments, the distance between irradiated regions of the target tissue are equal to or less than: about 4 mm apart, about 8 mm apart, about 12 mm apart, values between the aforementioned values, or ranges spanning and/or including those values. In some embodiments, the distance between irradiated regions is determined using graduations on the introducer probe. In some embodiments, the trocar sleeve assembly 427 can be reinserted into another region of the target tissue (for example, a laterally disposed second insertion point) and the above irradiation and withdrawal process can be repeated. In some embodiments, the laser assembly is repositioned into different areas of a tumor after irradiation.

Figure 7J:
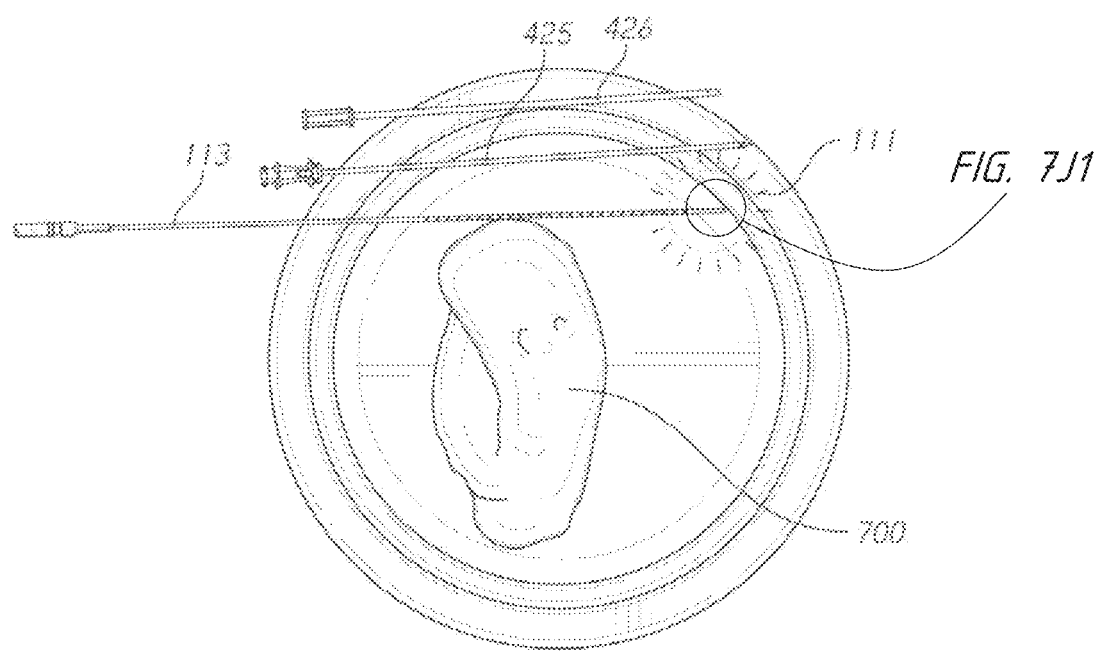

In some embodiments, as for the test sample shown in FIGS. 7A-7J, the method of treating a tumor or tumors in a target region (e.g., a tumor in an organ or gland) can include a step for positioning the trocar sleeve assembly 427 in a patient. In some embodiments, the trocar sleeve assembly is positioned by passing the trocar assembly through, for example, a prostate tumor such that the trocar assembly passes through a proximal face of the tumor (toward the user who is inserting the trocar sleeve assembly) and terminates at a distal side of the tumor (away from the user who is inserting the trocar sleeve assembly). In some embodiments, the insertion of the trocar sleeve assembly from the proximal to the distal side of the tumor and creates a first path within the tumor. In some embodiments, as described with the test specimen of FIGS. 7A-7J, the method of treating a tumor can include a step for removing the trocar from the patient and leaving the catheter (e.g., the catheter sheath 426) in the patient within the first path. In some embodiments, a laser catheter assembly 101 (e.g., a laser illuminator assembly) can be acquired. In some embodiments, as discussed elsewhere herein, the laser catheter assembly 101 can comprise one or more of an introducer probe 113 and an optical fiber 202. In some embodiments, as shown in FIGS. 7J and 7J1, the introducer probe 113 (e.g., the laser introducer probe) comprises a first lumen and terminates in a sealed domed end configured to allow laser light transmission. In some embodiments, as shown in FIG. 7J1, the introducer probe comprises an internal tube located within the first lumen 116 of the introducer probe 113. In some embodiments, the internal tube 117 comprises a second lumen 118. In some embodiments, as shown in FIG. 7J1, the optical fiber 202 can be positioned within the second lumen 118. In some embodiments, when positioned within the second lumen, the optical fiber and its diffusing tip 204 can transmit laser radiation through the domed end 115 of the introducer probe 113. In some embodiments, the first lumen is in fluidic communication with the second lumen when the optical fiber is positioned within the first lumen.

In some embodiments, the method includes a step for inserting the laser illuminator assembly into the catheter sheath 426 and guiding the laser illuminator (e.g., the laser catheter assembly 101) to a first position within the first path in the tumor. In some embodiments, the first position is located near or at the distal side of the tumor. In some embodiments, the catheter can be partially removed to expose the introducer probe, or removed completely. In some embodiments, the method includes a step of activating the laser illuminator at the first position within the first path to generate non-ablative infrared radiation for a first period of time thereby heating the nanoparticles to an ablative temperature.

In some embodiments, the method includes a step for withdrawing the catheter and the laser illuminator to a second position within the first path. In some embodiments, the second position within the first path is closer to the proximal side of the tumor than the first position in the first path. In some embodiments, the laser illuminator is activated at the second position within the first path to generate non-ablative infrared radiation for a second period of time. In some embodiments, the illumination of the laser illuminator heats the nanoparticles to an ablative temperature.

In some embodiments, the method comprises withdrawing the catheter and the laser illuminator from the first path and inserting the trocar assembly into the patient at a second insertion point. In some embodiments, the second insertion point is laterally disposed on the proximal side of the tumor from the first insertion point. In some embodiments, the trocar assembly is positioned in the patient by passing the trocar assembly through the prostate tumor such that the trocar assembly passes through the proximal face of the tumor and terminates at the distal side of the tumor thereby creating a second path through the tumor. In some embodiments, the trocar is removed from the trocar assembly. In some embodiments, the introducer probe of the laser illuminator assembly is then positioned into the catheter. In some embodiments, the introducer probe is guided into place at a first position within the second path in the tumor. The catheter can be partially removed to expose the introducer probe, or removed completely. In some embodiments, the first position is located near the distal side of the tumor. In some embodiments the first position in any pathway could, alternatively, be intermediate between the proximal and distal faces of the target tissue (e.g., tumor).

In some embodiments, the laser illuminator is activated at the first position within the second path to generate non-ablative infrared radiation for a third period. In some embodiments, the activation of the laser illuminator at the first position of the second path heats the nanoparticles to an ablative temperature. In some embodiments, similar to the procedure used in the first path, the laser illuminator can be withdrawn proximally to a second position within the second path. In some embodiments, the laser illuminator can be activated at the second position within the second path to generate non-ablative infrared radiation for a fourth period of time thereby heating the nanoparticles to an ablative temperature.

In some embodiments, the laser illuminator is positioned at 1, 2, 3, 4, 5, 6, or more positions for illumination within each pathway. In some embodiments, the distance between irradiated regions of the target tissue within a pathway are equal to or less than: about 4 mm apart, about 8 mm apart, about 12 mm apart, values between the aforementioned values, or ranges spanning and/or including those values. In some embodiments, the period of time that the laser is active (e.g., the irradiation time) at each position in a pathway is equal to or at least about 1 minute, 3 minutes, 5 minutes, values between the aforementioned values, or ranges spanning and/or including those values.

In some embodiments, the irradiate and/or treat and withdraw method helps prevent seeding agents (e.g., cancer cells, etc.) along the path of the treatment. In some embodiments, the catheter sheath 426 can be withdrawn from the target tissue after placement of the introducer probe 113 at the distal target site. In some embodiments, the withdrawing method also helps cauterize tissue to prevent bleeding as the instruments are withdrawn. In some embodiments, by withdrawing the laser catheter assembly from the distal to the proximal side of the target tissue, blood can be coagulated and/or any bleeding can be substantially or entirely sealed-off. In some embodiments, by withdrawing the laser catheter assembly from the distal to the proximal side of the target tissue, the spread of tumor cells by blood flow, or push through of cancer cells out of the target tissue, etc.

In some embodiments, the insert and withdraw methods and/or other methods disclosed elsewhere herein can be performed on tumor tissues, on glands comprising cancer tissue, on organs comprising cancer tissue, and/or on structures (e.g., the throat) comprising cancer tissue. For instance, when treating the prostate gland, the introducer probe can be inserted through the prostate to a distal side and withdrawn as described elsewhere herein.

In some embodiments, as described elsewhere herein, a grid or template is used to determine the insertion points for the trocar sleeve assembly into the target tissue (e.g., tumor). In some embodiments, the template grid with laterally spaced apart holes is used to guide the trocar sleeve assembly placement. In some embodiments, each insertion point within the tissue of the patient is determined by the spacing of the holes in the template grid. In some embodiments, the lateral distance between insertion points determined by the template grid is equal to or less than: about 4 mm apart, about 8 mm apart, about 12 mm apart, values between the aforementioned values, or ranges spanning and/or including those values. In some embodiments, the lateral distance between insertion points is not determined using a template grid. In some embodiments, the lateral distance between insertion points is equal to or less than: about 4 mm apart, about 8 mm apart, about 12 mm apart, values between the aforementioned values, or ranges spanning and/or including those values. In some embodiments, multiple insertions (e.g., of multiple probes from multiple laser catheters) can be performed simultaneously using a grid. In some embodiments, the insertions can be performed serially using a single laser catheter and a grid.

In some embodiments, because infrared light can penetrate approximately 4 mm laterally from the introducer probe, for tumors or treatment areas having lateral widths greater than 8 mm, multiple insertions of a laser catheter assembly laser introducer probe (or probes) are used. When multiple insertion points are used, freehanded placement of laser introducers (or placement using, for example, a ruler to try and maintain spacing between laser dosing) can result in improper placement of the laser catheter assembly. The likelihood for improper placement can be high for intra-cavity treatments because it may only be possible to set the separation of the laser catheter assembly at the skin surface. In some embodiments, for tumors or treatment areas having lateral dimensions of greater than 8 mm, a device for positioning multiple laser catheter assemblies simultaneously (or repeated individual placements of a single laser catheter assembly) can be used to maintain a fixed separation between penetration points. In some embodiments, this device can be a type of template (e.g., a grid or jig).

Figure 8B:
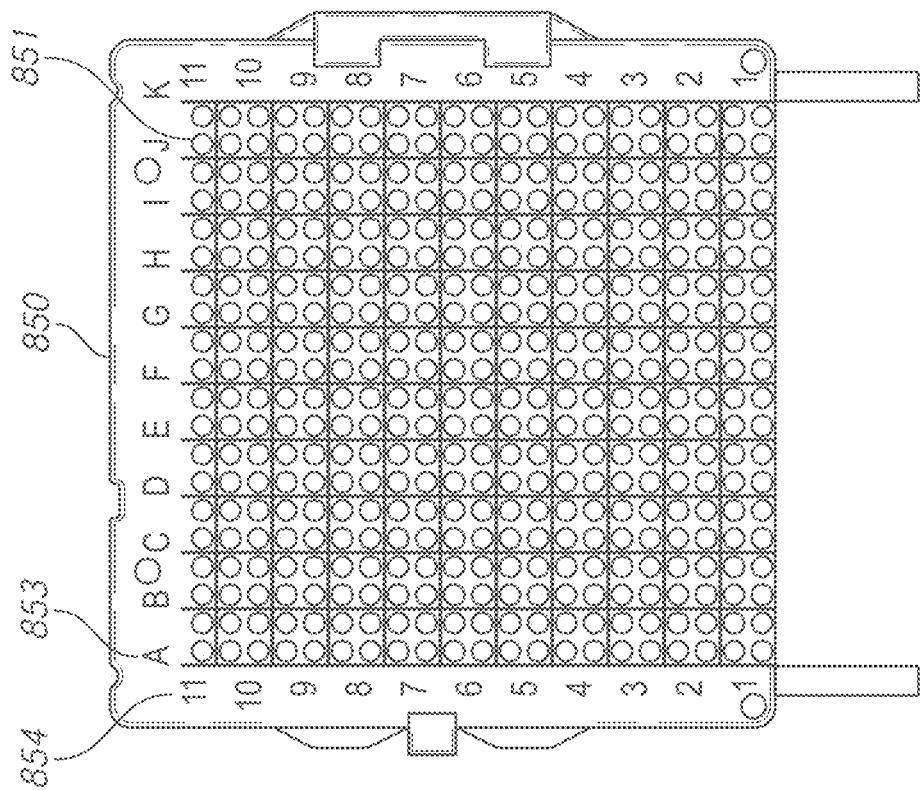
FIG. 8B depicts an embodiment of a square grid template.
Figure 8A:
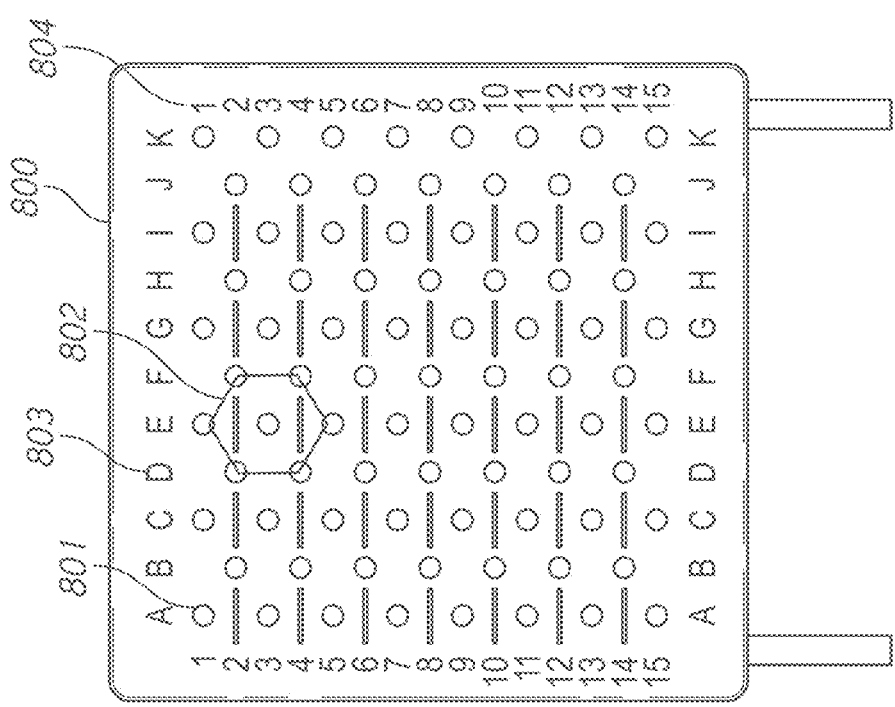
FIG. 8A depicts an embodiment of a hexagonal grid template for laser probe placement.

In some embodiments, a grid template as shown in FIG. 8A can be used to set and/or position laser catheter assemblies at selected separations and/or to maintain parallel alignment of multiple penetrations of laser catheter assembly introducer probes. In some embodiments, use of a grid helps prevent or lessen the amount of untreated margins of a tumor that can occur where the laser dose has been inadequate for particle activation, for example, because of improper probe placement. In some embodiments, the grid comprises a plurality of apertures 801. In some embodiments, each grid aperture 801 is configured to receive a sheathed trocar 425, a catheter sheath 426, and/or an introducer probe 113. In some embodiments, once the trocar 425 is placed in the target tissue, it is removed leaving the catheter sheath 426. The introducer probe 113 of the laser catheter assembly 101 can then be inserted into the sheath 426 and the method of irradiation as disclosed elsewhere herein can be performed. In some embodiments, as described elsewhere herein, a plurality (2, 3, 4, 5, 6, 7, 8, 9, 10, or more) laser catheter assemblies 101 and introducer probes 113 can be inserted into a plurality of sheaths 426 positioned using a grid. Then, the introducer probes 113 can be withdrawn together or serially during treatment (thereby shortening the time it takes to treat a target area). In some embodiments, a guidewire can be used. In some embodiments, a guidewire is not used to position the laser catheter assembly.

In some embodiments, hexagonal grids 802 are used as shown in FIG. 8A. In some embodiments, hexagonal grids 802 can be used to provide equidistant spacing to nearest neighbor probes. A square configuration grid 850 is shown in FIG. 8B. As shown, the grid apertures 851 of the square configuration grid 850 align to provide a square shape 852. As noted in FIGS. 8A and 8B, labeled markers 803, 804, 853, 854 can be used to indicate where a laser catheter should be placed within the grid 800, 850. As shown in FIGS. 8A and 8B, the labeled markers can comprise alphabetical indicators 803, 853 (e.g., A, B, C, D, E, F, G, H, I, J, K, L, M, N, O, P, Q, R, S, T, U, V, W, X, Y, Z, AA, etc.) or numeric indicators 804, 854 (e.g., 1, 2, 3, 4, 5, etc.) on different axes of the grid. Other indicators can be used, such as colors (e.g., red, orange, yellow, green, cyan, blue, indigo, violet, purple, magenta, pink, brown, white, gray, black), shapes (squares, circles, triangles, diamonds, pentagons, hexagons), or mixtures of color-coded shapes.

Figure 8D:
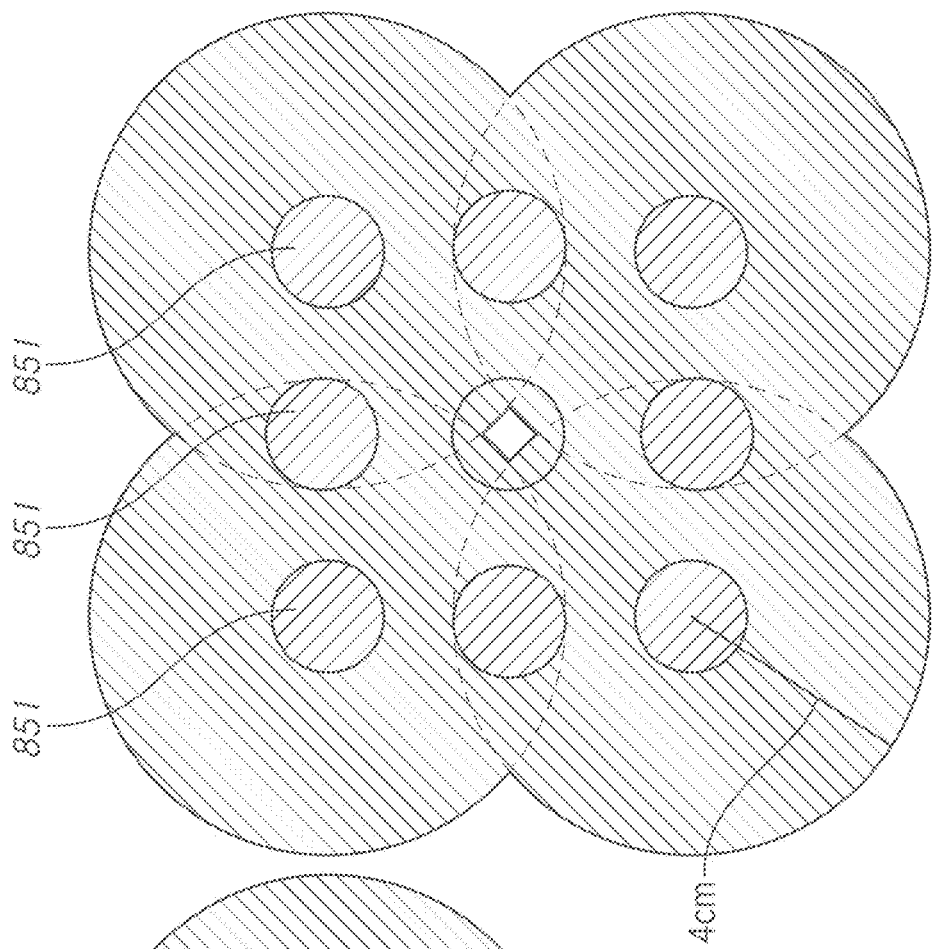
FIG. 8D depicts an embodiment of laser exposure regions using a square grid template with 3 mm spacings between grid apertures.
Figure 8C:
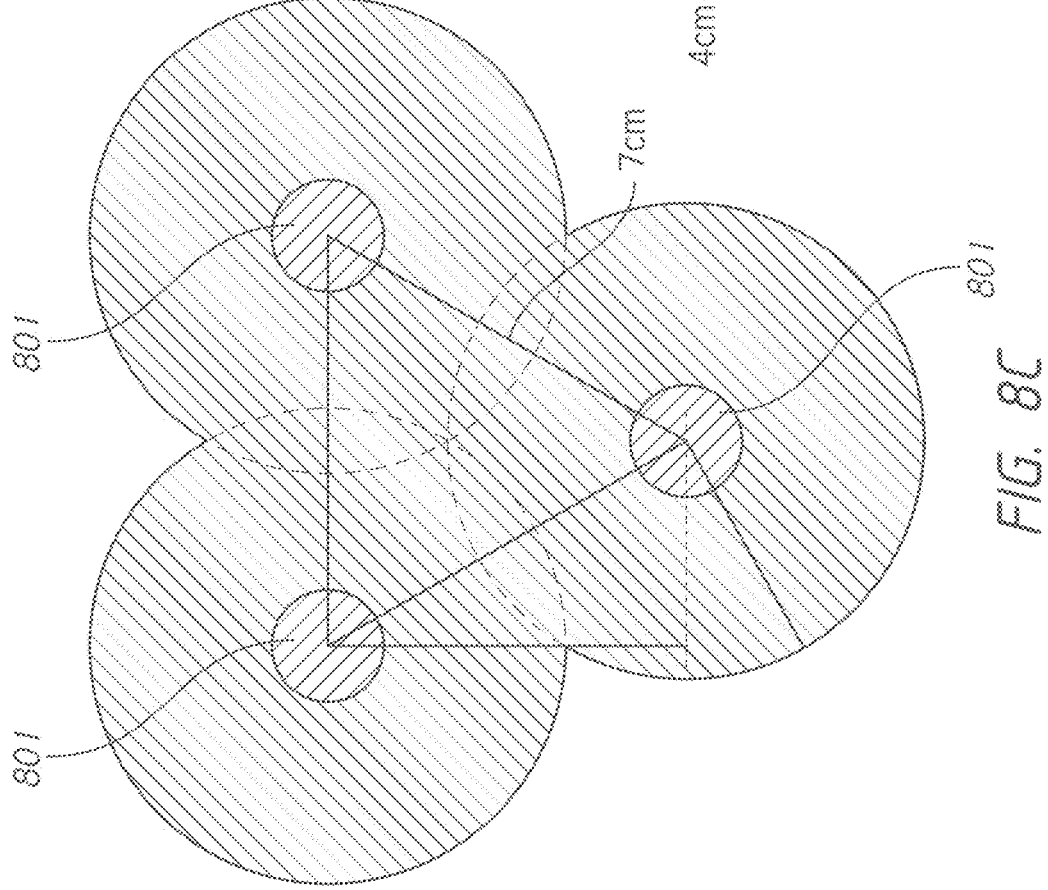
FIG. 8C depicts an embodiment of laser exposure regions using a hexagonal grid template with 7 mm spacings between grid apertures.

While square grids, as shown in FIG. 8B, permit straightforward identification of grid positions, they suffer from certain drawbacks as shown in FIGS. 8C and 8D. FIG. 8C depicts a hexagonal embodiment with a minimum aperture spacing of 7 mm. FIG. 8D shows a square configuration with an aperture spacing of 3 mm. Firstly, for square grids having 3 mm spacings (as shown in FIG. 8D), for example, the grid positions are 3 mm apart in both axes. This means that translation along a diagonal represents a translation of 4.24 mm as shown in FIG. 8D. Thus, in order to completely cover the lateral extent of a tumor for which the optical penetration radius is 4 mm, a square grid requires "over-sampling". That is, for a 3 mm square grid, alternate grid positions should be used along the principal axes, but along a diagonal there will be a potential untreated zone unless each diagonal grid position is used. This is turn leads to time-consuming treatment planning to calculate what grid positions must be used to completely cover the target area, and which positions can be bypassed. As shown in FIG. 8D, a square pattern of 9 grid positions with a 3 mm spacing showing the non-overlapping region (white) if a lateral position is not filled.

In some embodiments, the adoption of a hexagonal grid arrangement, a portion of which is shown in FIG. 8C, obviates these difficulties because each nearest neighbor position is equidistant. In some embodiments, once the boundary of the treatment zone is defined, then all of the interior grid positions are used, completely covering the target zone with minimal overlap. This leads to the dual advantage of decreasing the number (and/or minimizing) of introducer penetrations into the patient and decreasing the number (and/or minimizing) the treatment time. In some embodiments, a 7 mm spacing between grid apertures can be used to assure a maximum of 4 mm distance from any grid position. FIG. 8C shows 3 grid positions with a 7 mm spacing showing the convergence of the 4 mm radius treatment zones. As seen in FIG. 8C, in some embodiments, the maximum distance, at the center of each triad of holes is set at 4 mm. As a consequence, using adjacent holes for laser placement assures continuous coverage of a region with minimal redundancy, permitting the most efficient use of treatment time. In some embodiments, the spacing between adjacent grid apertures is less than or equal to about: 5 mm, 4 mm, 3 mm, 2 mm, values between the aforementioned values, or ranges spanning those values.

Figure 8E:
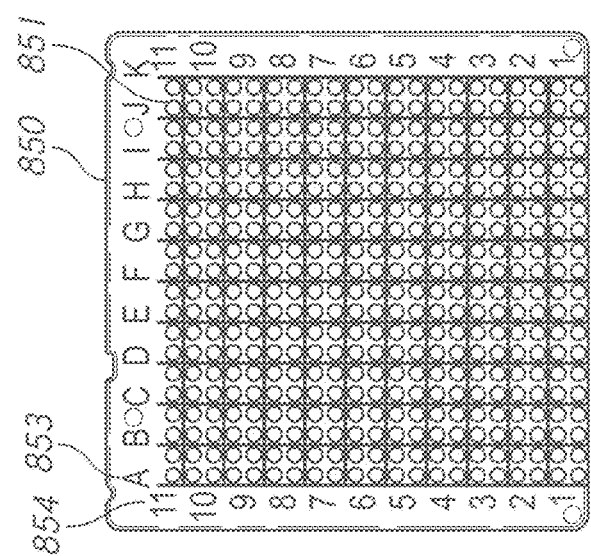
FIG. 8E shows a view of a disassembled three-part square grid.
Figure 8E:
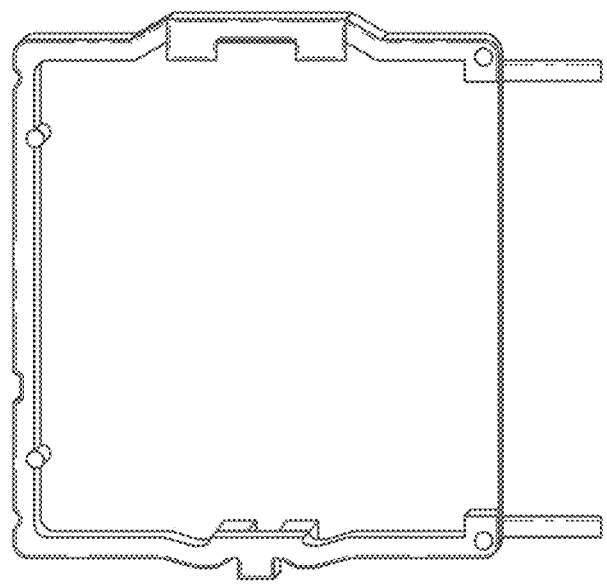
Figure 8E:
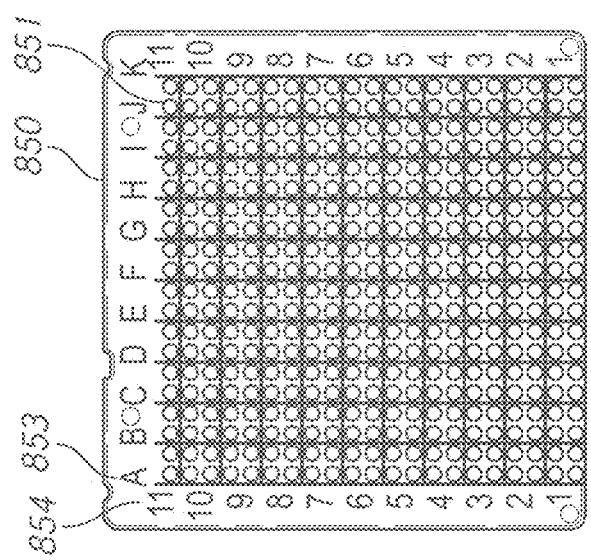

In some embodiments, the grid is prepared using a monolithic construction (e.g., a one piece design). In some embodiments, the grid is machined by computer numerical controlled milling from a single piece of plastic. In some embodiments, lettering and numbering (e.g., indicators) are etched into the plastic and/or printed onto the surface. In some embodiments, a monolithic design is distinct from the 3-piece template grids shown in FIG. 8E. In some embodiments, the apertures size is less than or equal to about: 20 gauge, 14 gauge, 12 gauge, values between the aforementioned values, or ranges spanning those values.

Figure 8G:
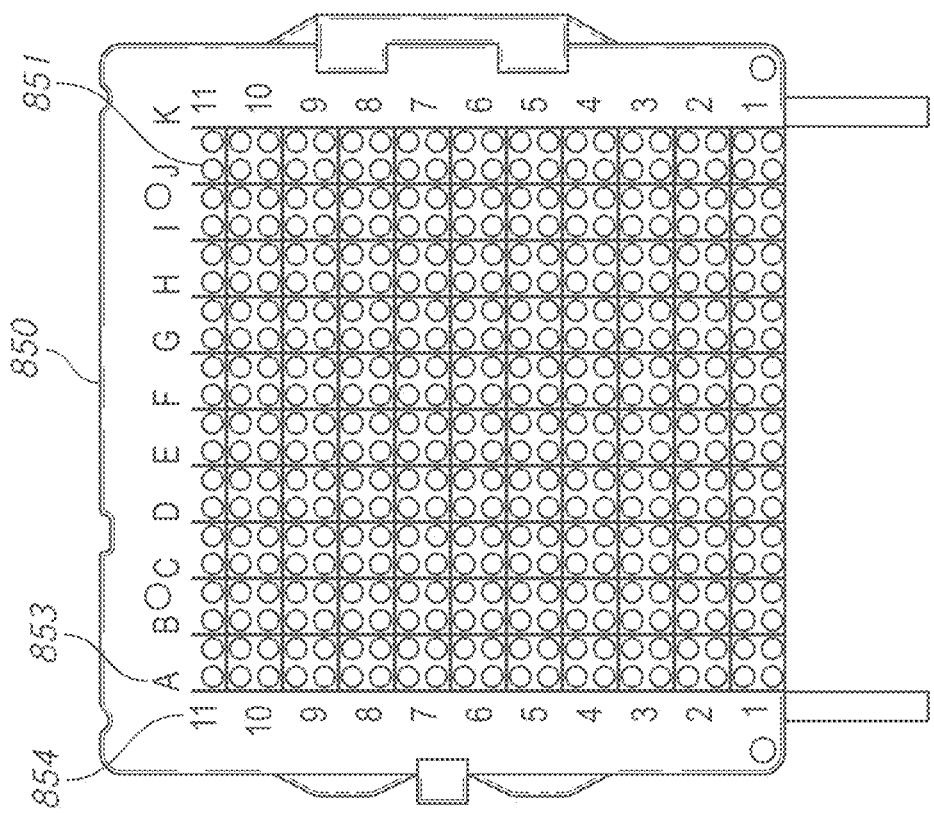
FIG. 8G is a view of an embodiment of a three-part square grid.
Figure 8F:
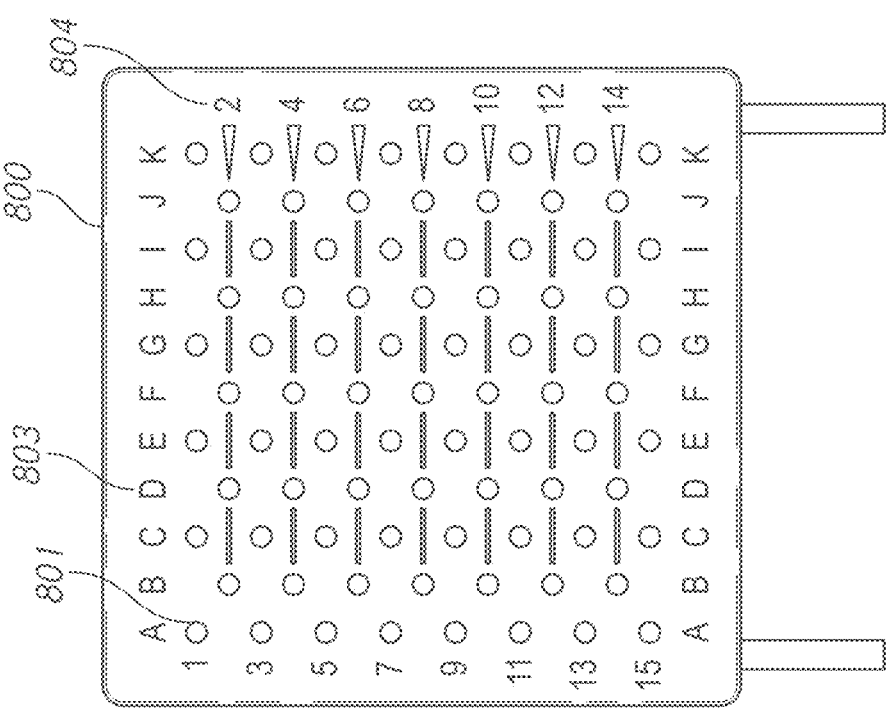
FIG. 8F is a view of an embodiment of a monolithic hexagonal grid.

In some embodiments, each number and letter designation in a square grid covers two holes, both vertically and horizontally, leading to a two-fold ambiguity in both axes for a given callout. In some embodiments, a 7 mm spacing of the hexagonal grid (as shown in FIG. 8A) permits unambiguous identification for every position as well as printed or inscribed horizontal lines on alternate rows of holes in order to facilitate accurate identification. Drawings of embodiments of a hexagonal grid and a square grid are shown in FIGS. 8F and 8G, respectively.

In some embodiments, during the treatment the laser illuminator can be activated by an actuator that is controlled by a user. In some embodiments, when the user activates the laser illuminator using the actuator, coolant automatically flows into the first inlet of the laser illuminator assembly. In some embodiments, when the laser illuminator is not active and not irradiating a tissue, coolant does not flow into the laser illuminator assembly. In some embodiments, the actuator is a foot pedal.

In some embodiments, as discussed elsewhere herein, laser power is absorbed by nanoparticles within a tissue. In some embodiments, upon absorption, the nanoparticle heat to sufficiently high temperatures to induce photothermal coagulation of tissue. In some embodiments, photothermal therapy using nanoparticles can be performed using a laser that is of sufficiently low power so that it does not in and of itself induce coagulative hyperthermia (e.g., 3.5-4.5 W/cm of diffuser). In some embodiments, the power of the laser is less than or equal to about: 2 W/cm, 3 W/cm, 4 W/cm, 5 W/cm, 6 W/cm, or ranges spanning and/or including those values. In some embodiments, coagulative hyperthermia occurs when the nanoparticles absorb the radiative energy. In some embodiments, non-coagulative hyperthermia can be induced at a temperature below about 45° C., about 35° C., about 30° C., or ranges spanning and/or including those values. In some embodiments, coagulative temperatures include tissue temperatures equal to or greater than about 45° C. In some embodiments, the laser can be activated for a period of about 3 to about 5 minutes without inducing temperatures that cause photothermal coagulation.

In some embodiments, the laser illuminator emits radiation having a near infrared wavelength. In some embodiments, the nanoparticles can be designed to have light absorption maxima in radiation in the near-infrared region (e.g. ranging from about 670 nm to about 1200 nm wavelengths) that allow the penetration of this energy through normal tissue. In some embodiments, upon the application of a laser emitting within these wavelengths, the nanoparticles absorb and convert this energy into heat to elevate the temperature of the tumor to an ablative level. In some embodiments, the effect of the nanoparticle-induced hyperthermia is to create a temperature elevation confined to the tumor and the region immediately adjacent thereto, localizing the area of tissue ablation and reducing damage on surrounding healthy tissue. In some embodiments, the laser illuminator emits radiation having a near infrared wavelength ranging from about 805 nm to about 810 nm. In some embodiments, a wavelength of about 805 to about 810 nm allows lower absorption by tissue (and hemoglobin), while increasing the absorption of the nanoparticles. In some embodiments, a wavelength of about 1000 nm can be used.

In some embodiments, the laser illuminator emits radiation that is of insufficient power to induce photothermal coagulation of tissue. In some embodiments, the optical fiber comprises a diffuser tip that distributes the non-ablative infrared radiation within the tumor. In some embodiments, the laser illuminator emits radiation between about 3.5 W/cm and about 4.5 W/cm of the diffuser tip.

Figure 9A:
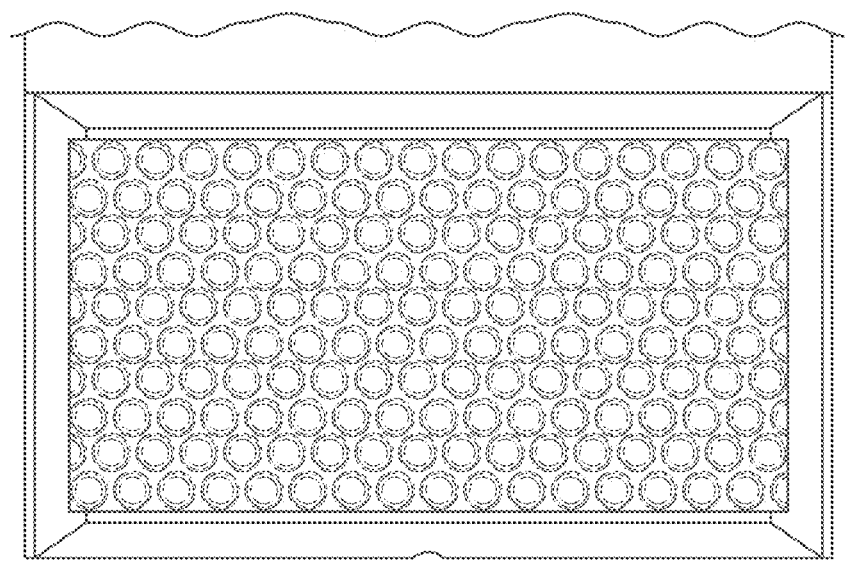
FIGS. 9A-9G illustrate components of an embodiment of a laser illuminating system kit.
Figure 9B:
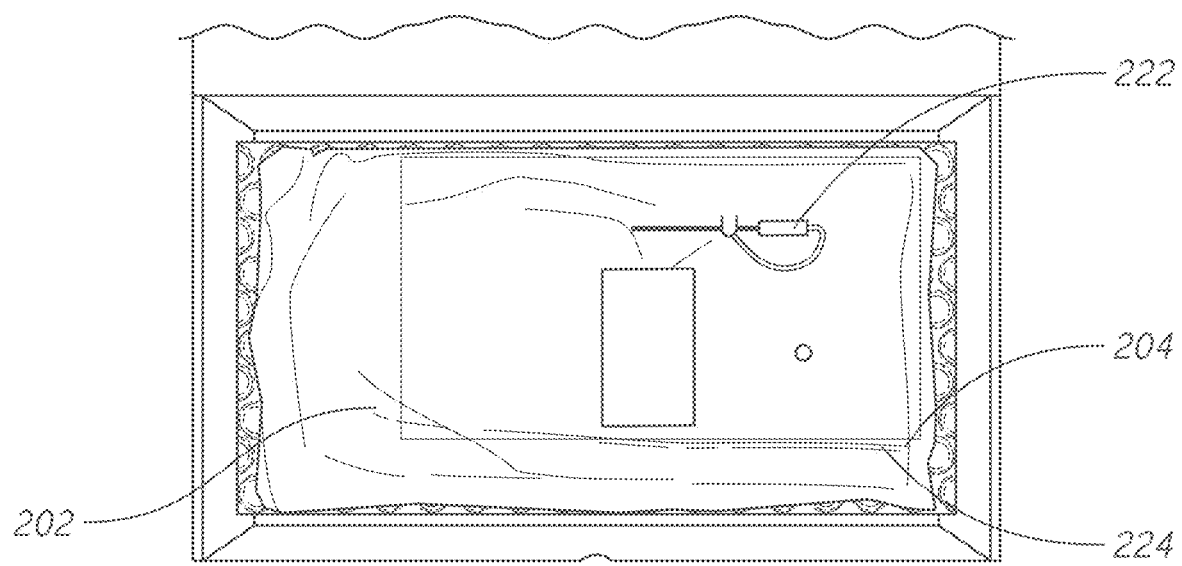
Figure 9C:
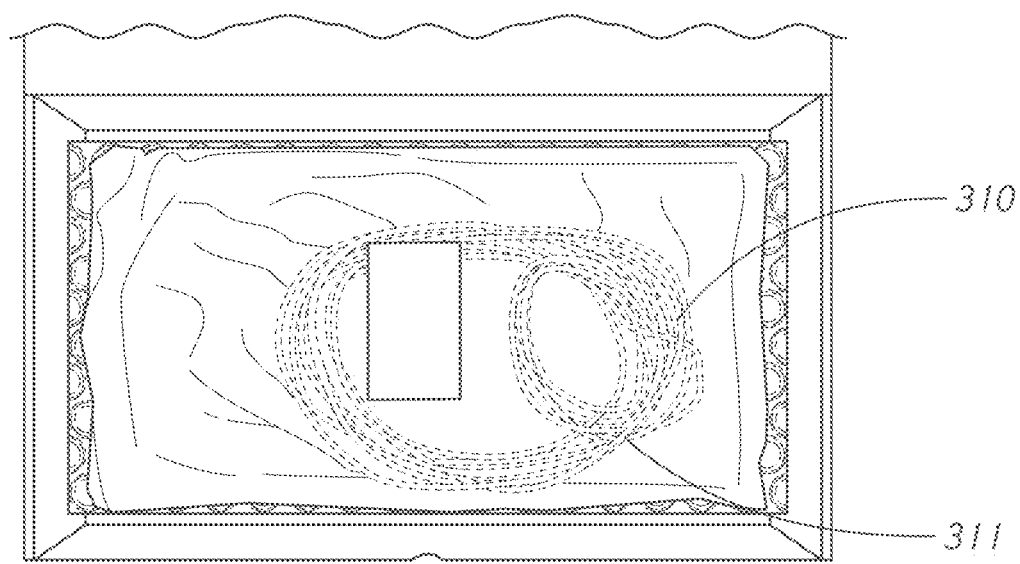
Figure 9D:
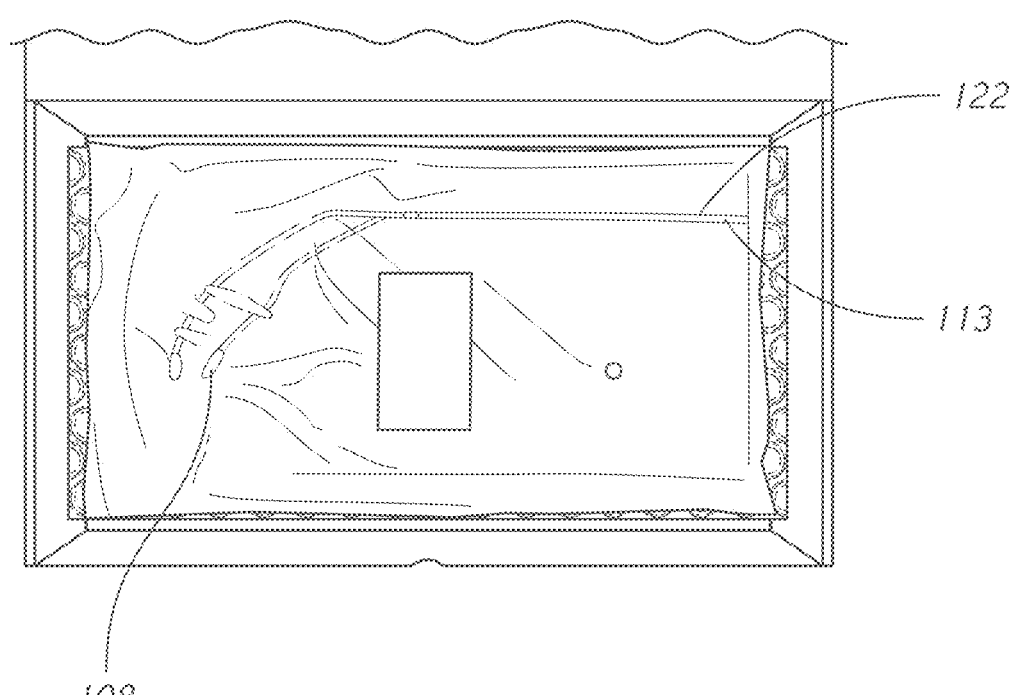
Figure 9E:
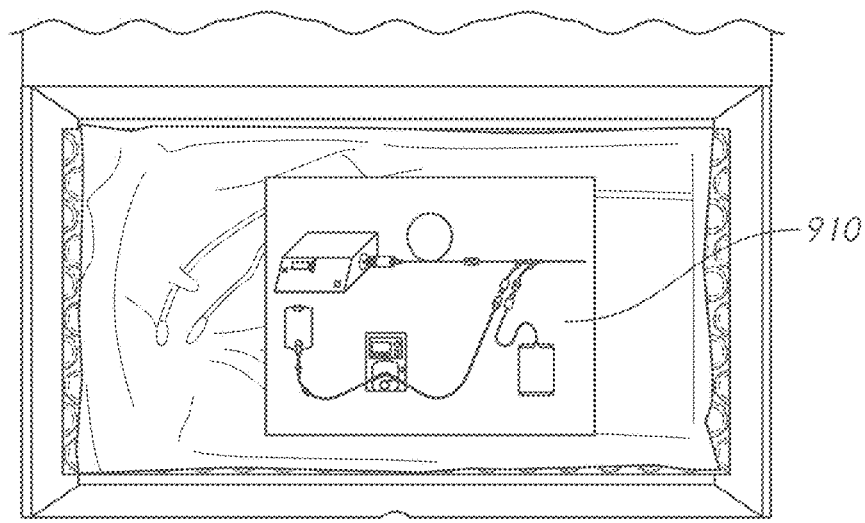
Figure 9F:
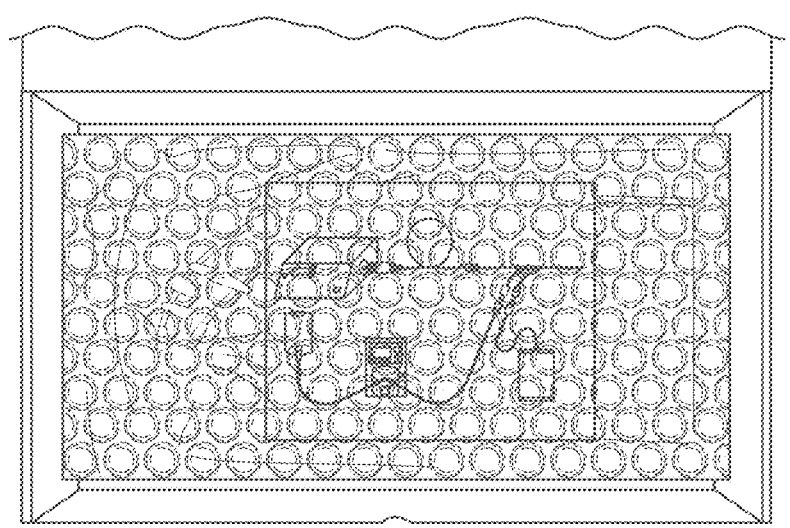
Figure 9G:
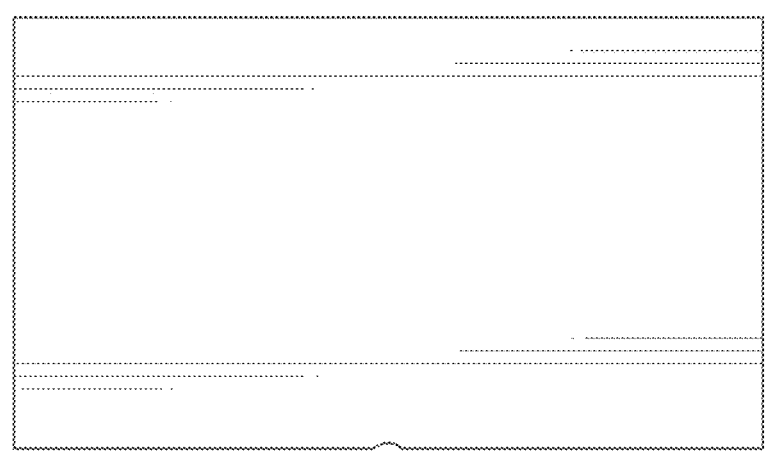

Some embodiments pertain to kits for use in laser therapy as described elsewhere herein. FIGS. 9A-9G show an embodiment of a kit, which can comprise one or more components of the laser illuminating system. In some embodiments, as shown in FIG. 9A a container with packing material can be provided. In some embodiments, the kit comprises an optical diffuser pack as shown in FIG. 9B. In some embodiments, the optical diffuser pack comprises an optical fiber 202 with an optical fiber tip and an optical fiber connector as described elsewhere herein. In some embodiments, the optical diffuser pack comprises a optical fiber sheath that protects the fiber and/or the diffuser tip. In some embodiments, the kit comprises a coolant supply set as shown in FIG. 9C. In some embodiments, the coolant supply set comprises one or more of a coolant reservoir, a coolant inlet conduit, an inlet conduit connector, a coolant recovery bag, a coolant outlet conduit, and/or a coolant outlet connector. In some embodiments, the kit comprises a laser catheter assembly packet. In some embodiments, the laser catheter assembly kit comprises one or more of a laser catheter assembly 101. In some embodiments, the introducer probe 113 of the laser catheter assembly is protected using a protective sheath 122 as shown in FIG. 9D. In some embodiments, the further comprises instructions 910 (e.g., on the assembly or use of the laser catheter assembly) shown in FIG. 9E. In some embodiments, the instructions may comprise drawings such as those shown in FIG. 1. In some embodiments, the method for using the laser catheter system as disclosed elsewhere herein is provided as part of the instructions. In some embodiments, as shown in FIG. 9F, an additional layer of packing material is used to cover the kit. In some embodiments, as shown in FIG. 9G, the packing container can be closed and sealed to provide a kit that is ready to ship. While not shown, in some embodiments, the kit may further comprise the coolant pump, the trocar and devices related there to, the grid assembly, etc. Additionally, one or more of the components shown in FIGS. 9A-9G can be excluded from the kit.

Some embodiments have been described in connection with the accompanying drawings. Some of the figures are drawn to scale, but such scale should not be limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

EXAMPLES

Example 1: Laser Catheter Testing

It has been observed that certain laser introducer probe tips of cooled catheter laser systems melt during clinical procedures and result in the formation of char on the tips with the consequent loss of light penetration into tissue. This char also results in non-specific coagulation and thermal fixation. The heating of the embodiments having a domed laser catheter tip was compared side-by-side to a Visualase® Cooled Catheter System (CCS) (having a ground conical tip). It was determined that the conical tip of the CCS created a significant focus of heat, greatly exceeding that of the domed laser catheter tip. The experiments described in this example show that the heating of the CCS is concentrated in the conical tip and that from one-third to over one-half of this heating is the result of end losses from the laser diffusing fiber (LDF). This conclusion was reached by using both the Visualase Laser Diffusing Fiber and embodiments having a domed laser catheter tip in the same conical Visualase Cooled Catheter System under the same conditions. When the embodiments having a domed laser catheter tip was used, the evolved heat was 34-57% less than when the Visualase LDF was used in the same Visualase conical-tipped catheter. Without being bound to a particular theory, the excess light leakage out of the end of the Visualase LDF and the conical catheter tip itself both contribute to the development of a device-destroying hot spot. The remainder of tip heating results from the shape and material of the catheter itself. In contrast to the 22-57° C. temperature rise using a CCS, the temperature rise in a domed laser catheter tip under similar experimental conditions was less than 2° C.

Test Organization

The Visualase CCS and a laser catheter assembly comprising a domed laser catheter tip were configured similarly to each other, with an isotropic diffuser tipped optical fiber secured within a transparent, dual lumen, liquid-cooled 16G catheter. Tests were performed in open air representing a "worst case scenario" in that there is no thermal coupling and/or heat transfer to tissue, which would tend to aid in the dissipation of heat away from the tip. The CCS was assembled as part of a standard Visualase Cooled Laser Applicator System (VCLAS). The tip of the 11 meter LDF was advanced to within 2 mm of the terminus of the CCS tip. The coolant inlet and outlet were supplied with a VCLAS tubing set (not including the extension set) supplied from a 1 L flask of room temperature water. Coolant was supplied by a Visualase K-Pump.

Figure 10B:
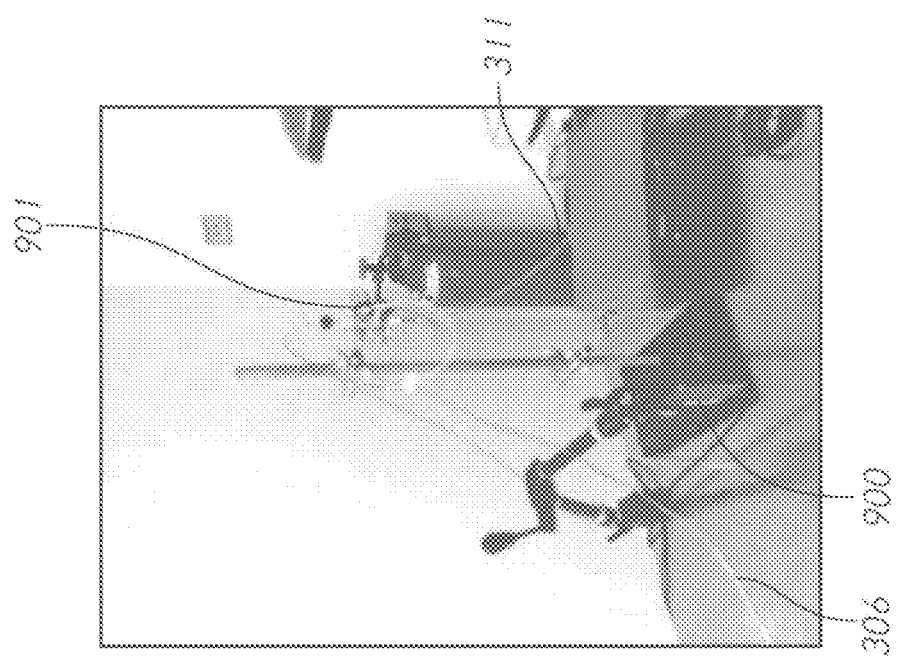
FIGS. 10A-10B are photographs of an experimental set-up for the testing of a laser catheter having a conical tip and a laser catheter assembly having a transmissive tip.
Figure 10A:
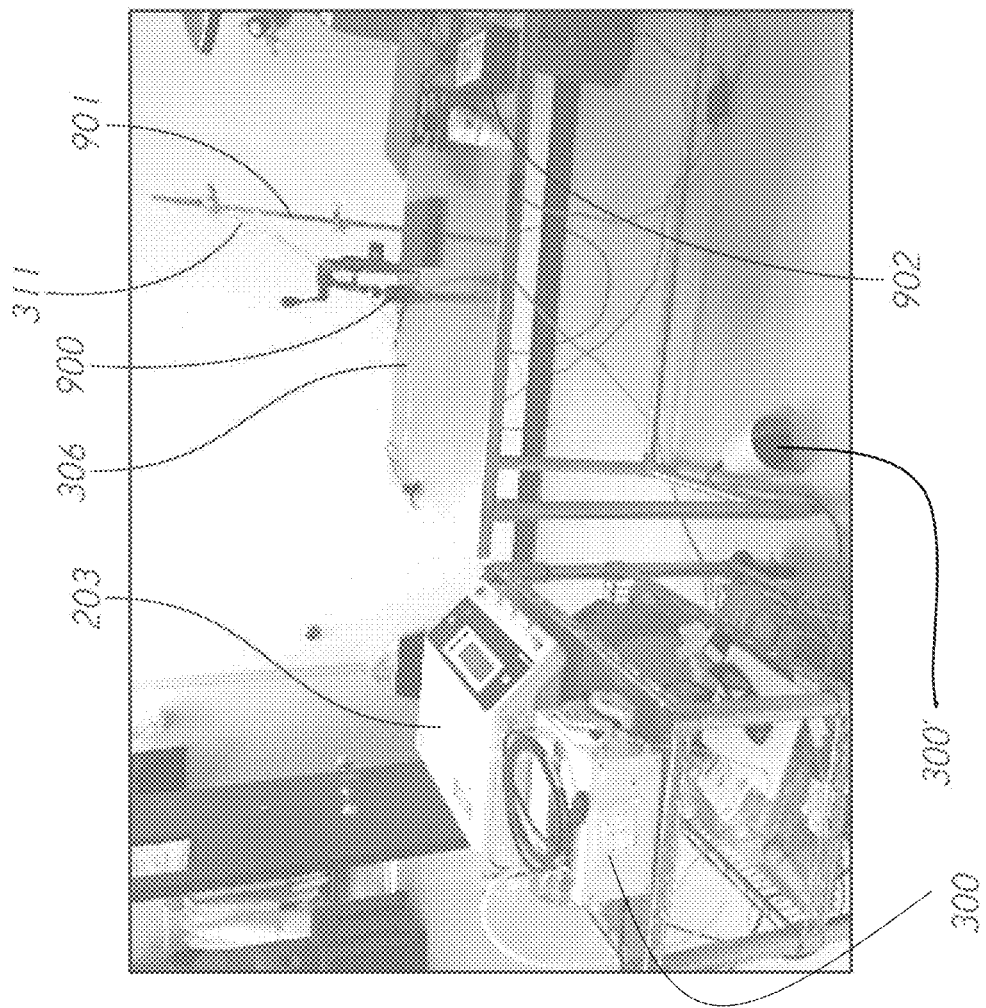

The experimental layout for the experiments performed is shown pictorially in FIGS. 10A and 10B. The coolant pump 307 and laser 203 were placed on a cart (at left of FIG. 10A) and were connected to the CCS/LDF assembly 901 via a coolant tubing set. A thermal camera 900, the small object mounted to the adjustable arm at the center of both FIGS. 10A and 10B, was operated from a laptop computer. A power source 902 is also shown. The CCS/LDF assembly is suspended on the ring stand shown in FIG. 10B. The laser power meter is at the right in the FIG. 10A.

Tests
1. Heating of the CCS/LDF assembly 4.5, 6.0, and 12.0 W laser power, measured in air, with nominal coolant flow.
2. Heating of the CCS assembly with an 18 mm AuroLase Optical Fiber Diffuser substituted for the Visualase LDF.

Test Conditions
Air: non-physiological condition that permits ready measurement by a thermal camera, and which represents a "worst case scenario" for thermal conductivity;
Orientation: in all cases the CCS assembly 901 was mounted vertically with the tip downward;
Laser output: 4.5±0.1 W for 10 mm diffuser, 6.0±0 0.1 W for 18 mm diffuser, and 12.0±0.1 W, 2× standard laser power (and near the maximum available laser output);
Nominal coolant flow: 7.9±0.2 mL/min water at room temperature (20-21° C.).

CCS Experimental Setup
Laser: Diomed 15+#10000126
Coolant pump: Visualase K-pump, property #10000125
Coolant supply: standard AuroLase Therapy CSS
Optical power optometer: Gigahertz-Optik P9710-2, NBI property #10000242/243
Thermal camera 900: ICI model 3720.
Data recording and image control software: Lenovo Ultrabook Yoga 2 pro running custom ICA IRFlash application Test Articles
The Cooled Catheter Assembly with Laser Diffusing Fiber advanced to 2 mm from catheter tip;
Cooled Catheter Assembly with 18 mm Optical Fiber Diffuser advanced to 2 mm from catheter tip.

Heating of the CCS/LDF Assembly

Figure 11A:
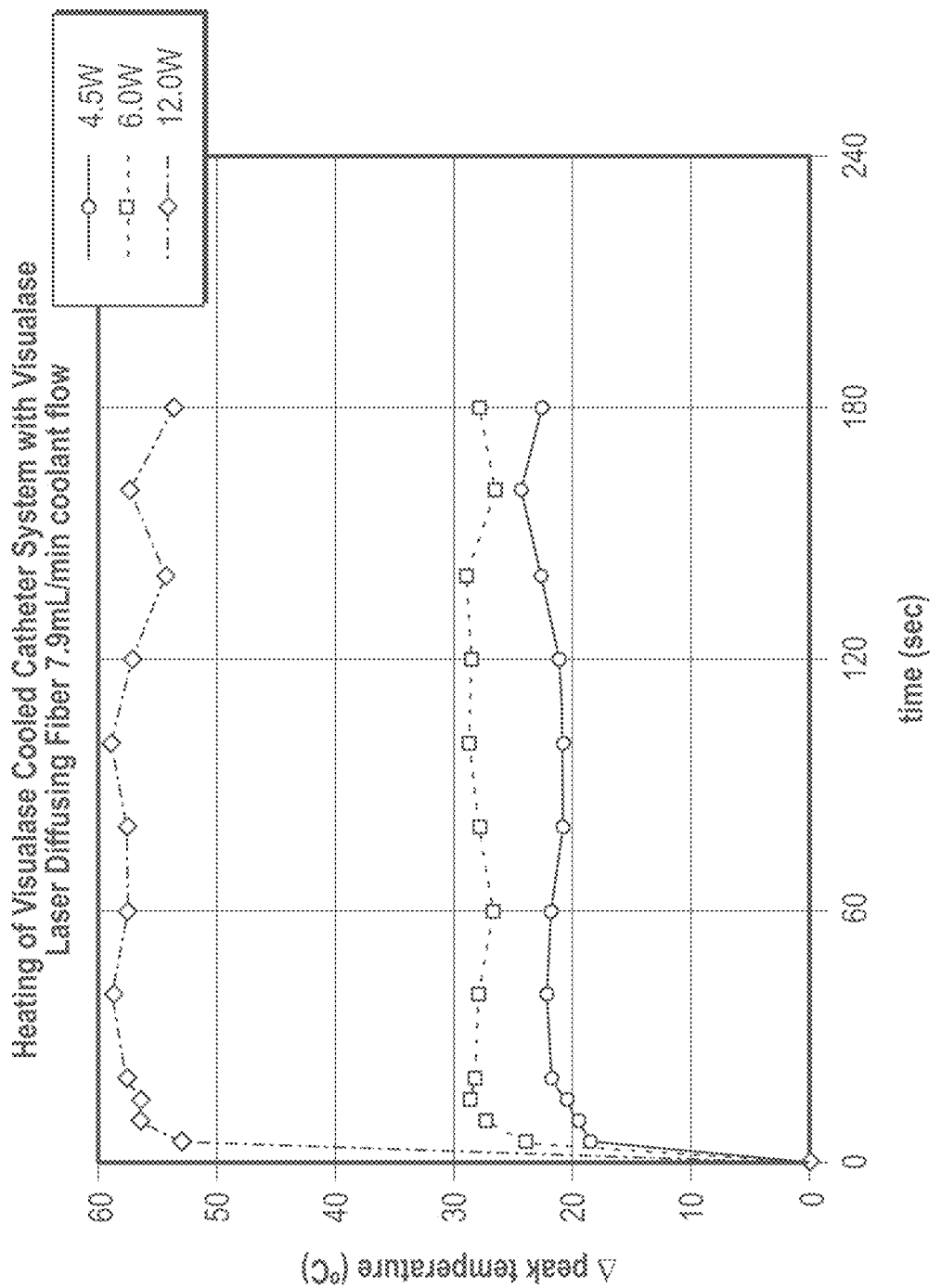
FIGS. 11A-11B are graphs showing the heating of a laser catheter having a conical tip (11A) and of a laser catheter assembly having a rounded transmissive tip (11B).
Figure 11B:
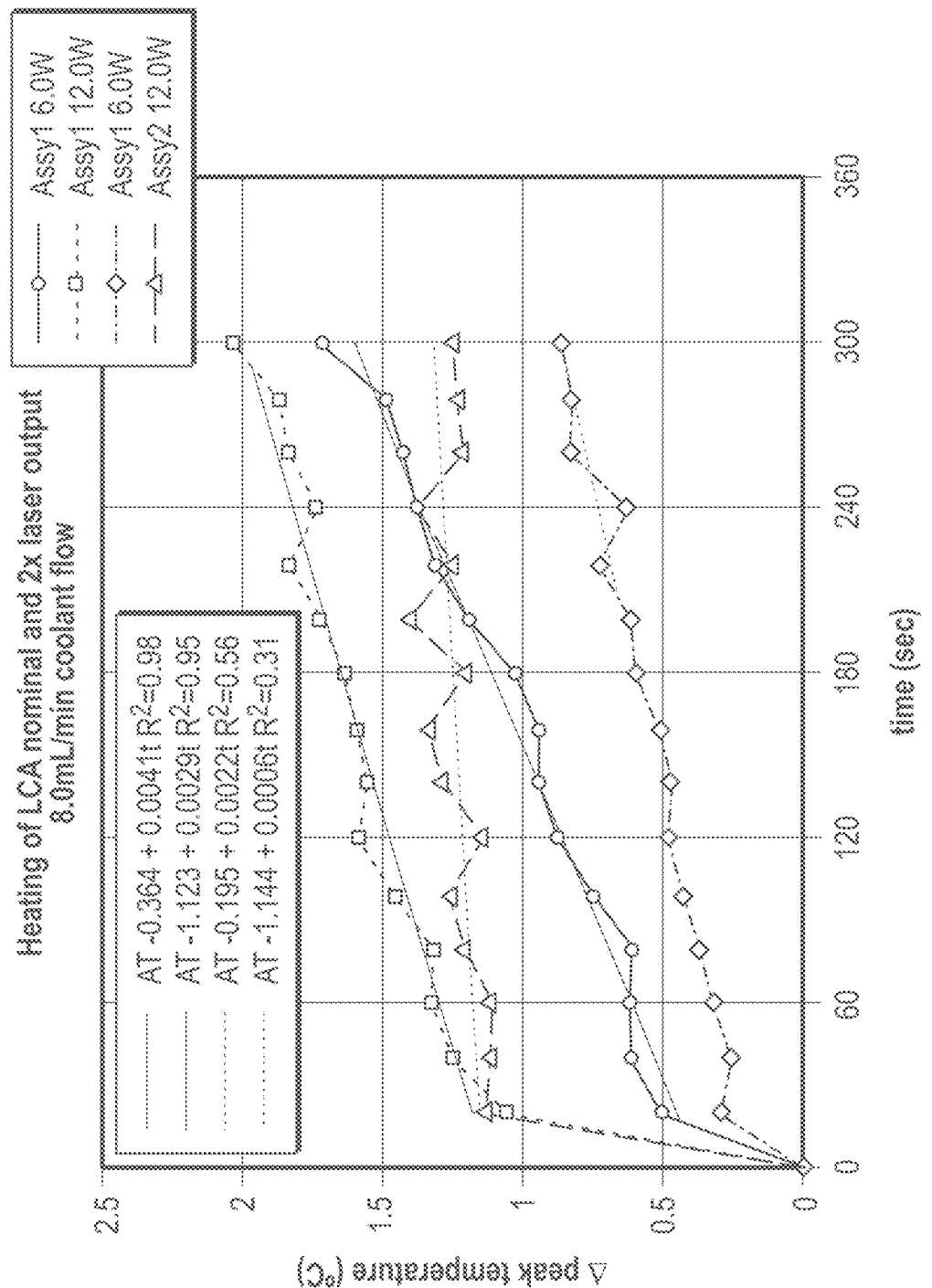

FIGS. 11A and 11B show the data for a Visualase® Cooled Catheter System (CCS) (having a ground conical tip; FIG. 11A) and for a domed laser catheter tip as disclosed elsewhere herein (FIG. 11B). FIG. 11A shows the increase in peak temperature of the distal end of the CCS assembly over 3 minutes of 4.5, 6.0, and 12.0 W of laser output. The coolant flow was un-interrupted and set at 7.9 mL/min sourced from a room temperature (20° C.) 1 liter reservoir. The temperatures followed a characteristic first order transient response. At 4.5 W the temperature rose 22°, at 6.0 W the rise was 28° C., and at 12.0 W the rise was 57° C. Settling at the final temperature was rapid, with a time constant of 1.9-2.9 seconds, effectively coming to equilibrium within 15 seconds in all cases.

FIG. 11B shows the heating of the laser catheter assembly comprising a domed laser catheter tip under heating conditions coinciding to those of previous irradiation of the Visualase system in FIG. 11A. By comparison, for the laser catheter assembly comprising a domed laser catheter tip at 12.0 W irradiation, the temperature rose 1.2-1.6° C. above ambient temperature during the course of a standard 3-minute treatment. FIG. 11B shows heating of the laser catheter assembly comprising a domed laser catheter tip under nominal (6.0 W/18 mm diffuser) and 2× laser output for both Assembly #1 (circles) and Assembly #2 (squares). Assemblies #1 and #2 are two identical optical fiber/laser catheter assemblies that were tested under identical conditions. The assemblies were cooled at 8.0 mL/min with room temperature water. FIGS. 11A and 11B are scaled differently in order to clearly show the temperature evolution in detail. For instance, FIG. 11B shows an expanded view of the temperature.

Figure 12A:
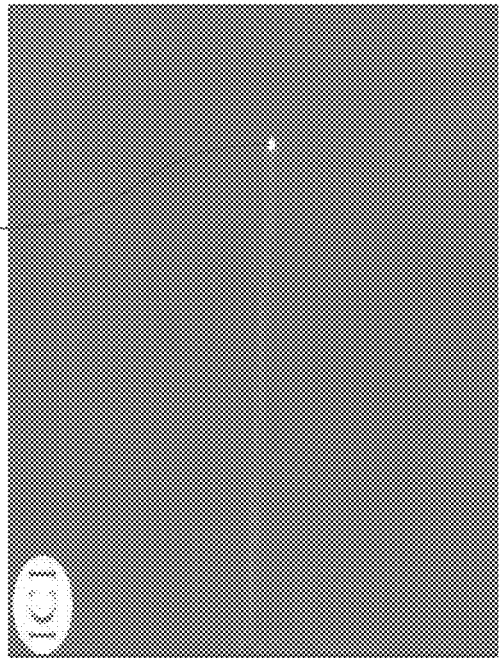
FIGS. 12A-12B depict thermal images of the distal end of a laser catheter having a conical tip after 6.0 W irradiation.
Figure 12B:
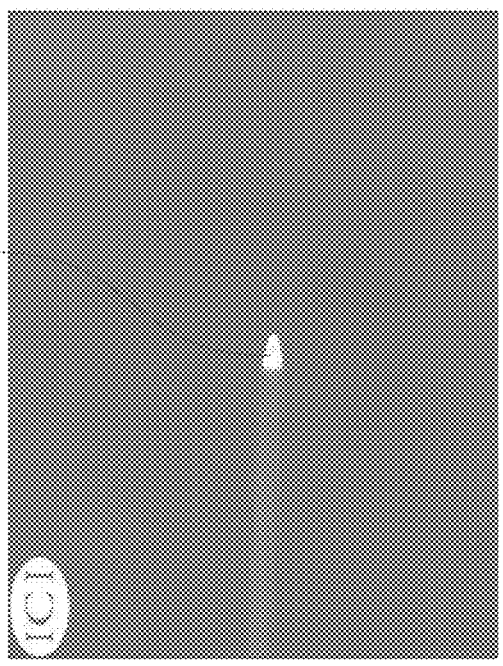
Figure 12C:
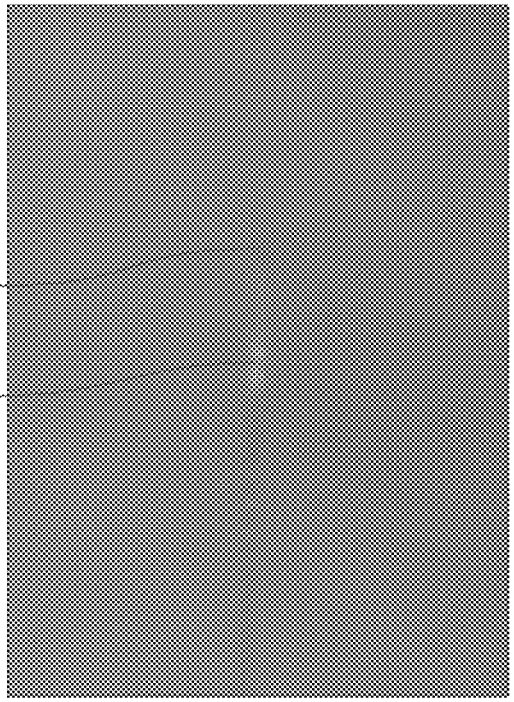
FIGS. 12C-12D depict thermal images of the distal end of a laser catheter having a domed tip after 6.0 W irradiation.
Figure 12D:
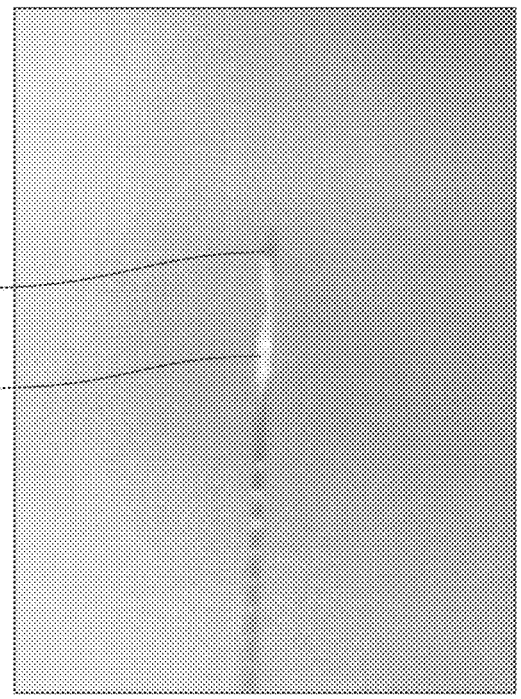

FIGS. 12A and 12B show false-color thermal images of the distal end 950 of the CCS/LDF assembly and the end of the 6.0 W irradiation. FIGS. 12C and 12D show false-color thermal images of the distal end of an embodiment of a domed catheter at the end of the 6.0 W irradiation. Heat is concentrated at the very tip of the CCS, which is 52.4° C., or 280 above ambient. FIG. 12B shows a close-up of the CCS/LDF tip under 6.0 W irradiation clearly showing heat buildup at the extreme end of the conical tip. From FIG. 12A, it is immediately apparent and clear that the heating is concentrated within the conical tip. This is further demonstrated by the close-up of the CCS tip in FIG. 12B where the hottest portion is seen to be the extreme tip of the CCS. From FIGS. 12C and 12D it is apparent that heat does not build in the tip of the domed cooled catheter.

2. Heating of the CCS/OFD Assembly

The evolution of heat by the different laser catheters has two sources: the optical fiber diffuser itself and the material and conformation of the enclosing catheter. In order to distinguish between these two contributions an optical fiber diffuser of the laser catheter system described elsewhere herein was substituted into the CCS and the laser irradiations were repeated.

Figure 13:
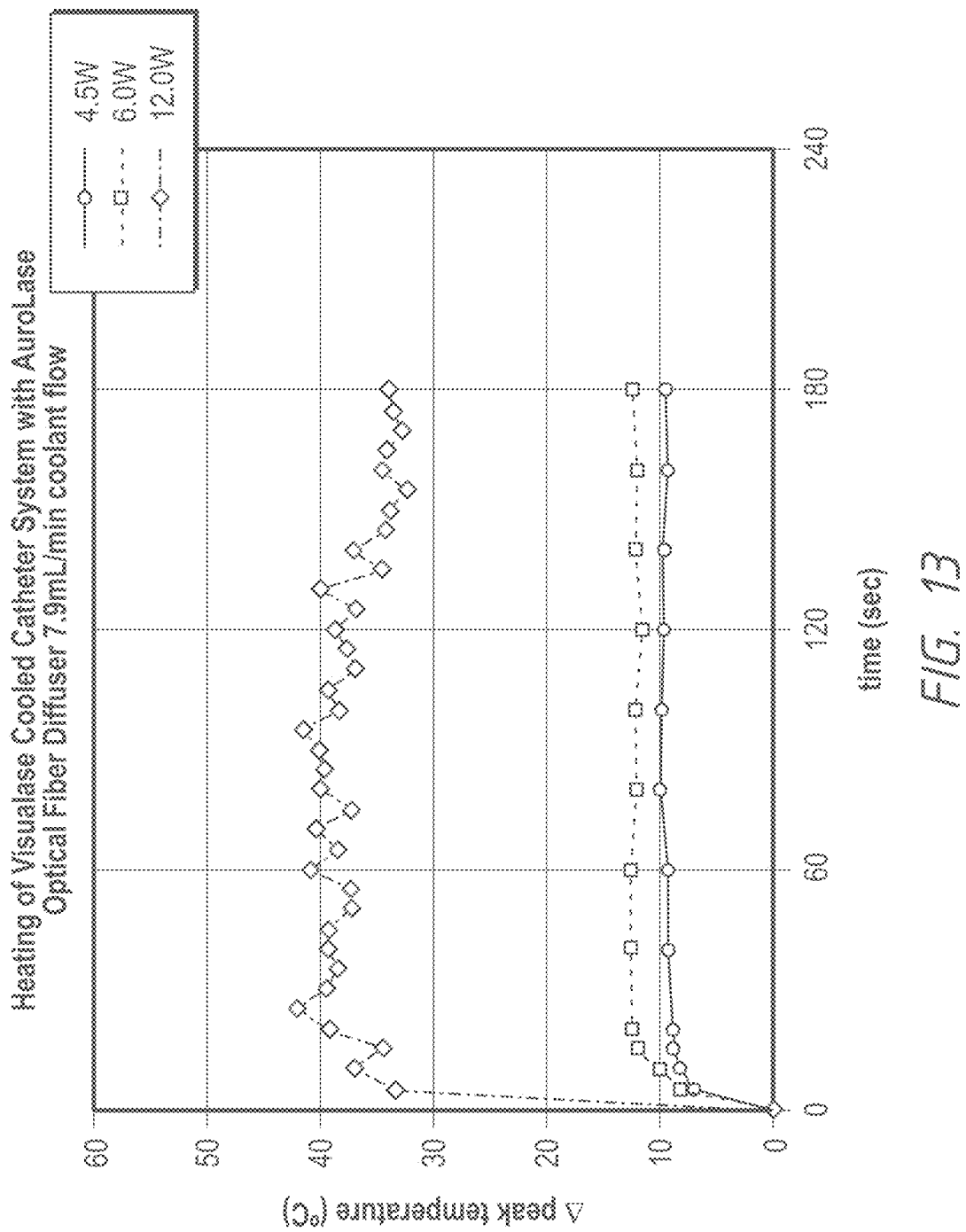
FIG. 13 depicts the heating of a conical tip laser catheter when an optical fiber having an 18 mm diffuser is used.

FIG. 13 shows the increase in temperature of the CCS using an embodiment of a laser diffuser disclosed herein (having an 18 mm diffuser tip) instead of the Visualase Laser Diffusing Fiber. FIG. 13 records the increase in peak temperature of the distal end of the CCS/OFD assembly over 3 minutes of 4.5, 6.0, and 12.0 W of laser output. The coolant flow was un-interrupted and set at 7.9 mL/min sourced from a room temperature (20° C.) 1 liter reservoir. The temperatures also followed a characteristic first order transient response. At 4.5 W the temperature rose 9.4°, 12.3° C. at 6.0 W, and 38° C. at 12.0 W. Settling at the final temperature was less rapid than previously, with a time constant of 2.2-4.8 seconds, effectively coming to equilibrium within 25 seconds. Overall, the change from the LDF to the OFD reduced the evolved heat by 57% for the 4.5 W output, 56% for the 6.0 W output, and 34% for the 12.0 W output. Since the heating of the CCS is overwhelmingly in the conical tip it was concluded that: 1) the 34-57% reduction in heating afforded by switching to an optical diffuser disclosed herein is the result of greatly reduced end loss from the diffuser tip, and 2) the appreciable heat is the result of light being focused within the conical tip.

CONCLUSION

The observed tendency for the conical tips of Cooled Catheter Systems to melt during clinical procedures results in the formation of char on the tips with the consequent loss of light penetration into tissue and in non-specific coagulation and thermal fixation. The experiments described herein demonstrate that this heating of the CCS is in fact concentrated in the conical tip, from ⅓ to over ½ of this heating is the result of end losses from the Laser Diffusing Fiber, and the remainder from the shape and material of the catheter itself. By contrast, with the 22-57° temperature rise in the CCS, the temperature rise using embodiments of laser catheter assemblies as disclosed herein (e.g., an embodiment as disclosed herein having a domed tip) under near-identical conditions was less than 2° C.

Example 2: Treatment of a Prostate Tumor

This is a single-arm study with a single group of patients. An objective of the study is to determine the efficacy of using MRI/US fusion imaging technology to direct focal ablation of prostate tissue using nanoparticle-directed laser irradiation.

The patient population consists of men with low to intermediate risk localized prostate cancer with MRI visible and confirmed focal areas of prostate cancer using MRI/US Fusion Guided Biopsy. The patient also has no disease detected via ultrasound guided biopsy outside of areas visualized on MR imaging.

There is one arm/group to this study: Up to forty five (45) patients receive a single intravenous infusion of AuroShell particles 12 to 36 hours prior to MRI/US guided laser irradiation using an FDA cleared laser and an interstitial optical fiber.

Efficacy and acute volume of ablation is assessed by contrast-enhanced MRI 48-96 hours after laser illumination to allow time for the appearance of coagulative necrosis and prior to reconfiguration of tissue by lytic action. An appearance of a 'void' on MRI is more generally expected than lesion shrinkage.

Efficacy of focal ablation of prostate tissue is assessed by MRI/Ultrasound guided biopsy at 90 days (primary endpoint) and again at 1 year after laser treatment. Per standard of care patient follow-up is on a 6 month basis beyond the one year follow up but is outside the scope of the initial study.

Nanoparticle Dose: in this study AuroShells are used. These are gold nanoshells. AuroShell Dose: Each patient receives an infusion of up to 7.5 mL/kg of AuroShell particles concentrated to 100 Optical Density (approximately $2.77 \times 10^{11}$ particles/mL or 36 mg particles/kg of patient weight). AuroShell particles are administered intravenously through a standard non-DEHP infusion set, and are infused at rates ranging from 120 mL/hour to the nominal 600 mL/hour at the investigator's discretion.

Laser Dose: Laser illumination takes place under ultrasound guidance 12 to 36 hours after particle infusion. An isotropic fiber in a water-cooled jacket with an isotropic diffusing tip is inserted via transperineal approach. The urethra is cooled by circulating saline (or water) through a urethral catheter. Up to 5.0 Watts per cm of optical fiber diffuser length of measured output of 810±10 nm laser power is delivered for a period of up to 4 minutes for each treatment site. If necessary, the laser fiber is repositioned and a separate zone illuminated.

Inclusion Criteria

Patients have documented histological or cytological evidence of tumor(s) of the prostate. Patients are ≥45 years of age. Patients or their legal representative are able to read, understand and sign an informed consent. Organ confined clinical T1C or clinical T2a prostate cancer that is visualized on MR imaging. Prostate cancer is diagnosed by MR image guided biopsies. Gleason Score ≤7; and 2 or less positive lesions on prior MR US fusion guided prostate biopsy. If the standard biopsy cores are positive, they should be from the same location in the prostate as MR lesion was biopsied and proven to be cancerous. (Left/Right, Base, Mid Gland, Apex). Prior MRI results dated within 120 days prior to ablation. No metastatic disease as per NCCN guidelines (www.nccn.org)—Bone scan indicated to r/o metastatic disease if clinical T1 and PSA >20 or T2 and PSA >10 PSA <15 ng/ml or PSA density <0.15 ng/ml2 in patients with a PSA >15 ng/ml. The patient has given written informed consent after the nature of the study and alternative treatment options have been explained.

Exclusion Criteria

Patients with known hypersensitivity to any of the components of a PEGylated gold nanoshell suspension (polyethylene glycol, gold). Patients who are receiving concurrent investigational therapy or who have received investigational therapy within a period of 5 half-lives of the investigational therapy in question prior to the day of dosing with the PEGylated nanoshell particles.

Introduction

Prostate cancer is the most commonly diagnosed cancer in men. In 2014, approximately 233,000 men in the United States were diagnosed with prostate cancer and an estimated 29,000 died from the disease. The average annual incidence of prostate cancer among African American men was 60% higher than among non-Hispanic white men, and the average annual death rate was more than twice that of non-Hispanic white men.

Existing treatment modalities for primary prostate cancer include "active surveillance", surgical resection, and radiation (including brachytherapy). These modalities have a significant level of side effects, including erectile dysfunction, urinary incontinence, and rectal damage. Focal therapeutic approaches that reduce the adverse effects associated with treatment, eradicate the current disease, or potentially increase the time to progression are needed.

The optical properties of tissues inherently limit the depth of propagation of optical energy, thereby enabling a truly focal therapy. Heat evolved from an energy source is inherently diffuse and non-specific. Although thermally ablative heat can be made to propagate on the millimeter scale, it is not specific to tumor conformation. Nanoshell particles offer the opportunity for more precisely localized conformal therapy and result in tumor specific damage on the millimeter scale.

The MRI fusion imaging approach, using ultrasound guidance based on a priori MRI fusion imaging, should permit the precise placement of the optical fiber catheter within or adjacent to the prostate lesion(s) targeted for ablation.

A merging of MRI fusion imaging and the subsequent directed placement of the laser catheter represents a means of establishing the efficacy and utility of nanoshell therapy for the focal therapy treatment of prostate tissue. The MRI-Ultrasound fusion approach resolves limitations identified using an ultrasound only approach; given the ability of MR US fusion technology to allow:

1) pre-treatment target planning, and 2) guided imagery to be used as an additional level of safety after the initial use of ultrasound for planning placement of the catheters using a brachytherapy stepper which allows for the accurate placement of the laser catheter in proximity to the lesion to be ablated.

The methods can also be used in squamous cell carcinomas of the head and neck, canine melanomas and carcinomas of the oral cavity, and in canine and human prostate all serve to demonstrate the inherently focal nature of particle-directed photothermal energy. Incorporation of an imaging modality can enable precise lesion treatment. Further, the ability of particles to co-locate to neoplastic tissue can further enable lesion ablation conformal to the target tumors.

The potential benefit of nanoshell therapy is highly selective and rapid tumor destruction with minimal damage to surrounding tissue enabling a potentially curative treatment of tumors with minimum toxicity. Preclinical studies have demonstrated that nanoshell therapy is effective and causes no detectable systemic toxicity.

Investigational Devices and Systems

Nanoshells and the laser illuminating system disclosed herein selectively destroy solid tumors using near infrared illumination from a laser. Unlike other energy-based ablation methods, which rely upon the endogenous absorption and transduction of the deposited energy into heat, nanoshell particles, delivered systemically to the tumor, serve as an exogenous absorber of this laser illumination to generate a lethal thermal response specific to tumor tissue.

Nanoshell therapy is comprised of three components: (i) a near infrared laser source, (ii) an interstitial fiber optic probe for delivery of the laser energy to a site near and/or inside the tumor, and (iii) nanoshell particles, a near-infrared absorbing inert material designed to absorb and convert the laser energy into heat. Nanoshell particles are delivered systemically, and allowed to accumulate selectively at the tumor site and then illuminated by a near-infrared laser. The particles absorb and convert this illumination into heat, resulting in the thermal destruction of the tumor and the blood vessels supplying it with minimal damage to surrounding healthy tissue. Since the accumulation of the particles within the peri-vascular space of tumors is passive and depends only upon the fenestrated neo-vasculature characteristic of solid tumors, nanoshell therapy may be used in patients previously treated with chemotherapy and radiation. During the procedure, needle thermocouples placed around the tumor may be used to monitor margins of treatment. In some embodiments, this will provide monitoring of temperatures around the ablation zone and permit the operator to minimize the risk of overheating critical structures or areas outside of the intended target tissue. Low temperature control points (about 45° C. to about 50° C. threshold) are used near critical structures, such as the urethra, urinary sphincter and rectal wall, in order to avoid damage to these tissues.

Nanoshell therapy is useful in recurrent and refractory head and neck cancer and metastatic lung tumors.

There is one arm/group to this study. Up to forty five (45) patients receive a single intravenous infusion of nanoshell particles 12 to 36 hours prior to ultrasound-guided laser irradiation using an FDA cleared laser and interstitial laser fiber. Acute efficacy and volume of ablation is assessed by contrast-enhanced MRI 48-96 hours following the laser illumination in order to allow time for the appearance of coagulative necrosis but, prior to reconfiguration of tissue by lytic action. An appearance of a 'void' on MRI would be more generally expected than lesion shrinkage.

Nanoshell/laser catheter therapy is a system for the photothermal ablation of solid tumors using near-infrared energy. The system utilizes an interstitial fiber optic probe to deliver near-infrared energy emitted by an FDA-cleared laser to a site proximate to and/or inside a solid tumor. Unlike other energy-based ablation methods, which rely upon the endogenous absorption and transduction of the deposited energy into heat, Nanoshell/laser catheter therapy particles, delivered systemically to the tumor, serve as an exogenous absorber of this laser illumination to generate a lethal thermal response specific to tumor tissue.

Nanoshell/laser catheter therapy is comprised of three components: (i) a near infrared laser source, (ii) an interstitial fiber optic probe for delivery of the laser energy to a site near and/or inside the tumor, and (iii) nanoshell particles, a near-infrared absorbing inert investigational material designed to absorb and convert the laser energy into heat.

Nanoshell/laser catheter therapy may be used with an FDA-cleared clinical laser that emits near infrared energy with the desired parameters (energy, duty cycle, cycle time) and with an interstitial fiber optic probe for percutaneous energy delivery. The nanoshell particles used in this study consist of a gold metallic shell and a non-conducting, or dielectric, core that serves as the exogenous absorber of the near infrared laser energy delivered by the fiber.

Nanoshell/laser catheter therapy in this study uses an FDA-cleared laser, either the Diomed 15-PLUS (K013499) or LiteCure, LLC (K093087) as an infrared energy source and an interstitial, liquid-cooled optical fiber source.

The steps involved in Nanoshell/laser catheter therapy can include one or more of: (i) the intravenous infusion of a dose of nanoshell particles, (ii) a time delay of 12 to 36 hours to allow the accumulation of the nanoshell particles within the tumor by the enhanced permeability and retention (EPR) effect, and (iii) the illumination of the area with continuous wave (CW) or pulsed coherent light at a desired wavelength, for example, between 800 and 815 nm, for up to 4 minutes at up to 5.0 Watts average delivered output (assuming a 1-cm long isotropic diffusing delivery). The nanoshell particles in the area absorb light, and the metal shell converts the absorbed light to heat, generating heat sufficient to thermally ablate the tumor. The applicator can be positioned externally or inserted interstitially or endoscopically and can use either a collimated or dispersing fiber tip.

Nanoshell particles used in this study consist of a metallic shell and a non-conducting, or dielectric core. These particles can be designed and constructed to absorb or scatter light at desired wavelengths. This "tunability" is achieved by altering the ratio of the thickness of the metal shell to the non-conducting core. The exterior shell of the particle is comprised of gold, which has a long history of use in vivo in particulate form, as an implanted material, or as a coating on implanted devices. The non-conducting core is silica, but can be comprised of any dielectric material. For cancer therapy, nanoshell particles are designed to absorb infrared light at wavelengths where light is not significantly absorbed by human tissue. Human tissue is minimally absorptive in the ranges from 750 nm to 1100 nm, often referred to as the "water window" or "tissue optical window". While solid gold nanoparticles and microparticles absorb light at wavelengths also absorbed by tissue, gold-coated nanoshell particles can be designed to absorb or scatter light within this "tissue optical window", enabling new in vivo applications.

More specifically, the nanoshell particles used in this study are comprised of a thin gold shell, 10 to 20 nm thick, deposited on a solid silica (silicon dioxide) core. To prevent aggregation of the particles in a saline environment and to provide steric hindrance in vivo, a 5,000 molecular weight (MW) methoxy-polyethylene glycol (PEG) chain is attached through a thiol (sulphur) bond. The PEG coating improves the stability of the nanoshell particles in an isotonic aqueous solution, and may also improve circulating half-life on administration. For the studies reported here, the particles are concentrated to a desired level (generally less than 0.1% by volume) and suspended in an isotonic solution for injection (10% trehalose in water).

Mechanisms of Action

Lasers and radiofrequency ablation devices are used to thermally destroy tissue by delivery of energy at a rate in excess of the tissue's ability to dissipate the energy through blood perfusion thermal diffusion. In addition, some lasers provide energy at wavelengths naturally absorbed by chromaphores within tissue or blood, using the properties of tissue or blood as a natural absorber to convert the light to thermal energy. The result is either thermal coagulation of cells or tissue thermal fixation and the disruption of the vasculature.

Nanoshells particles are infused intravenously and are known to accumulate in tumor stroma as a result of the fenestrated vasculature associated with tumors. This method of accumulation has been established by other particles and is termed the EPR effect. SEM analysis of tumor tissue following nanoshell particle intravenous injections indicates particle accumulation is preferentially near the tumor vasculature.

Nanoshell particles are designed to absorb near-infrared energy, transducing it into heat via surface plasmon resonance. The near-infrared dose level utilized by Nanoshell/laser catheter therapy is below that which would cause significant damage to tumor or normal tissue without the presence of nanoshell particles. In the presence of nanoshell particles in tissue, the near-infrared dose will generate a thermal response that may be sufficient to result in photothermal coagulation, leading to cell death. It is likely that this to include the disruption or occlusion of tumor vasculature in a manner similar to the FDA-cleared embolism microspheres.

Preparation of Nanoshells

The nanoshell particles used in this study are packaged in units of 80 mL in a sterile IV bag and maintained at 2 to 8° C. For infusion, the package should be removed from refrigeration and allowed to warm to room temperature over 30 minutes. The bag should be gently kneaded or shaken to ensure the uniform dispersion of the material. The tubing for infusion should be C-Flex, non-DEHP, medical grade tubing. A 1.2 micron filter (Pall TNA1 or comparable) should be installed between the infusion tubing and the patient catheter.

Particle Dose and Administration

The nanoshell particles are infused at a rate of 600 mL/hour (10 mL/minute). During the three days prior to and first 6 hours after administration, vasoconstrictive medications are avoided to maximize particle accumulation in tumor. Each patient receives an intravenous infusion of up to 7.5 ml/Kg of nanoshell particles concentrated to 100 Optical Density (approximately $2.77 \times 10^{11}$ particles/mL or 36 mg particles/kg of patient weight.

Laser Application

Laser illumination will take place under MRI/US fusion guidance 12 to 36 hours after particle infusion. The urethra may be cooled by circulating saline (or water) through a urethral catheter (typ. 6-10 mL/min). An optical fiber with an isotropic diffusing tip in an enclosed catheter is inserted interstitially using a transperineal approach employing 14G needle/cannula introducers. Up to 5.0 Watts of measured output of 810±10 nm laser power is delivered for a period of up to 4 minutes for each treatment site. If necessary, the laser fiber may be repositioned and a separate zone illuminated.

The specific procedures are described in the Instruction Manual for AuroLase Therapy (IFU), but a summary of the procedure is as follows:

Prior to use, calibrate the laser and verify laser output through the laser fiber to up to 5.0 Watts/cm average output. Prior to use, verify that the cooling system for the laser fiber is functioning properly. Using ultrasound guidance, insert needle/cannula introducers into the prostate proximal to the index lesion to be treated, avoiding the urethra and other critical structures. The MRI generated fusion images are not used for guidance of the laser placement, but serve only as a check on the placement via ultrasound guidance. Withdraw the needle from the introducer and replace it with the laser catheter. Withdraw the cannula to expose the emitting portion of the laser catheter. If indicated by the proximity of the target lesion to a sensitive or critical structure (e.g., urethra, prostate capsule, or nerve bundle) a needle thermocouple may be inserted at clinician discretion alongside the laser catheter in order to monitor temperatures near the treatment zone. Position the fiber to illuminate a zone within the prostate for up to 4 minutes. If indicated by the size of the lesion to be treated, withdraw the fiber a distance of 2 mm less than the illumination length and illuminate the new zone. Repeat as required to illuminate the entire lesion. If additional target lesions are to be treated, repeat steps at the new site. If a single target lesion is treated, the investigator will make a single laser treatment in the contralateral prostate hemisphere to serve as a negative control of the laser treatment (i.e., no thermal damage to normal tissue in the absence of the accumulation of particles in the perivasculature of tumor tissue). In the event of the treatment of two lesions with one in each hemisphere of the prostate, this negative control procedure will not be performed. At the discretion of the investigator, if a Foley catheter was used to cool the urethra during the laser procedure it may remain in order to prevent occlusion of the urethra as a consequence of thermally-induced edema. The Foley catheter may remain in place until the follow-up MRI on Day 4/5.

Complete physical examination (general appearance, skin, neck, ears, eyes, nose, throat, lungs, heart, abdomen, back, rectal, lymph nodes, extremities, neurological status) is performed at baseline and the 90 day follow-up.

A follow up MRI fusion biopsy is taken at the 90 day follow-up visit to assess the efficacy of the tumor ablation with a view to ascertain the presence of viable cancer cells within the treatment zone and therefore the efficacy of focal ablation of prostate tissue. The patient has the standard of care reassessment biopsy at Year 1 and six months thereafter per physician treatment considerations. This includes MRI/US fusion biopsy and a standard 12 core biopsy.

Results

The patients have an 70-80 percent reduction of tumor size 6 months after therapy. In 25% of the patients, the prostate cancer is completely eradicated. In 50% of the patients, no side effects are noted and normal prostate function is maintained.

Example 3 Treatment of a Head and Neck Tumors

A Pilot Study of AuroLase Therapy in Patients with Refractory and/or Recurrent Tumors of the Head and Neck.

This is an open-label, multicenter, single-dose pilot study of AuroLase Therapy in the treatment of patients with refractory and/or recurrent tumors of the head and neck. Three (3) treatment groups of five (5) patients each are enrolled and observed for six (6) months following treatment. Each group receives a single dose of AuroShell particles. This dose may be increased by up to 67% for the second and third group if no significant unanticipated adverse device effects are observed in the first group. The laser illumination for each group consists of one or more interstitial illuminations (based on tumor size) with an escalating laser dosimetry for the second and third groups.

The first group of five patients are treated with the lowest treatment level of 4.5 ml/Kg of AuroShell particles concentrated to 100 Optical Density (approximately $1.3 \times 10^{12}$ particles/Kg or 20 mg particles/Kg). An isotropic fiber in a water-cooled jacket with a one cm diffusing tip is inserted interstitially within and/or proximate to the tumor and up to 3.5 Watts measured average output of 800-810 nm laser power is delivered at a 75% duty cycle, 1.25 pulses per second for a period of up to four (4) minutes. The fiber may be repositioned at distances of 1 cm from the original placement to provide illumination to other sides of the tumor, or different tumors, with appropriate precautions. For tumors greater than 1.0 cm in estimated thickness at the point of fiber placement, the fiber may be retracted within the catheter to provide illumination of the tumor mass.

Following treatment of the first three (3) patients, safety data (including data from the fourth week visit after treatment) for each patient is submitted per FDA's request. In the absence of unanticipated adverse device effects, enrollment and treatment is continued for the two additional patients being treated at the lowest concentration of 4.5 ml/Kg (totaling (5) patients in the first group of the study). The AuroShell dose is increased from 4.5 ml/Kg to 7.5 ml/Kg of AuroShell particles concentrated to 100 Optical Density (approximately $2.1 \times 10^{12}$ particles/Kg or 34 mg particles/Kg) for the second and third group if no unanticipated adverse device effects related to AuroShell dose are observed in the first group.

For the second treatment group of five (5) patients, laser illumination may be increased to 4.5 Watts measured average output of 800-810 nm laser power delivered at a 75% duty cycle, 1.25 pulses per second for a period of up to 4 minutes if no unanticipated adverse device effects are observed in the first group.

For the third treatment group of five (5) patients, laser illumination may be increased to 5.0 Watts measured average output of 800-810 nm laser power delivered at a 100% duty cycle (continuous wave) for a period of up to 4 minutes if no unanticipated adverse device effects attributable to AuroLase Therapy are observed in the second group.

In each treatment group, the AuroShell particles is administered intravenously at a rate of 2 ml/minute for the first 15 minutes, and then increased to up to 10 ml/minute. At approximately 0.5, 2, 4, 8, 24 and 48 hours following administration of the AuroShell particles, a 2 ml blood sample is obtained and the concentration of the particles determined by dynamic light scattering analysis (DLS) and neutron activation analysis (NAA).

Approximately 12 to 36 hours after intravenous infusion of the particles, the target tumor(s) is illuminated by laser as described. Subsequent to the AuroLase treatment of the target lesions, biopsies is performed and the gold accumulation measured by neutron activation analysis.

In addition to the observations through the first day after laser treatment, patient follow-up occurs on weeks 1 and 2, and monthly thereafter for the 6 months following treatment.

INTRODUCTION

In the United States, approximately 46,000 cases of head and neck cancer are diagnosed on an annual basis, resulting in approximately 11,000 deaths annually. Unfortunately, despite multidisciplinary treatment efforts including surgery, radiation therapy, and chemotherapy, all of which are associated with substantial morbidity to patients, five year survival rates have not improved significantly over the last several years.

Nanoshell therapy can be used to selectively destroy solid tumors using near infrared illumination from a laser. Particles delivered systemically to the tumor serve as an exogenous absorber of this laser illumination to generate a thermal response.

Nanoshells

The nanoshells (e.g., Auroshells) can comprise a silica core approximately 110 to 125 nm in diameter (total diameter of particle including the gold shell is 140 to 170 nm); a functionalizing molecule to allow gold colloid to adhere to the silica, APTES (3-aminopropyltriethoxysilane); a thin layer of gold (10-20 nm thick) affixed to the functionalized surface of the silica core. The process of affixing the gold shell to the silica core includes the production of small colloidal gold nanoparticles 2 to 6 nm in diameter and the attachment of these nanoparticles to the amine groups present in the APTES. These colloidal nanoparticles act as nucleating sites for the reduction of gold salt (HAuC14) in the presence of formaldehyde, to complete the shell layer. The gold shell comprises approximately 95% of the particle mass. The attachment of a layer of 5,000 MW PEG-thiol to the surface.

Dose and Administration

In order to increase the EPR effect and AuroLase efficacy, at one hour prior to administration, the body temperature of the patient should be elevated by blankets or heating pads. A heating pad should be applied to the tumor area. If the tumor is in the oral cavity or proximate to the mouth or esophagus, cold beverages should be avoided.

AuroShell particles are administered intravenously at a rate of 2 ml per minute for the first 15 minutes of the infusion, increasing the rate to up to 10 ml per minute for the remainder of the infusion. Blood samples are taken at 0.5, 2, 4, 8, 24 and 48 hours for determination of blood clearance of AuroShell particles.

During the first 6 hours after administration, vaso-constrictive medications should be avoided to maximize efficacy. The first group of five (5) patients receives an intravenous infusion of 4.5 ml/Kg of AuroShell particles concentrated to 100 Optical Density (approximately $1.3 \times 10^{12}$ particles/Kg or 20 mg particles/Kg). The AuroShell dose is increased from 4.5 ml/Kg to 7.5 ml/Kg of AuroShell particles concentrated to 100 Optical Density (or approximately $2.1 \times 10^{12}$ particles/Kg or 34 mg particles/Kg) for the second and third group if no significant unanticipated adverse device effects related to AuroShell dose are observed in the first group.

Laser Application

Calibration and verification of proper operation of the AuroLase system is carried out prior to initiating the laser procedure and are summarized below. Based on MRI, CT or similar imaging technique, the tumor region is mapped to a grid by the surgeon to allow a systematic laser exposure of areas up to 1.0 cm outside the estimated tumor margin. This technique is based on an estimated 1 cm³ tissue treatment volume per laser application. At a point 12 to 36 hours after AuroShell infusion the patient is prepared for therapy. The patient may be sedated or anesthetized as determined by the physician. The laser and the cooling pump is plugged in and connected together with the interlock cable. The optical fiber is connected to the laser and threaded into the catheter. A sterile saline bag (1 liter) is hung and connected to the Laser Fiber cooling tubing set. The Laser Fiber cooling tubing is routed through the peristaltic cooling pump and connected to the inlet port of the catheter. The drain tube is connected to the outlet port of the catheter and to a fluid collection bag. The cooling pump is turned on and allowed to prime the cooling lines. The laser settings should be adjusted to deliver the desired average power. The power output of the fiber is checked by inserting the catheter into a sterile tube mounted in the integrating sphere optometer. The LASER POWER knob is adjusted to produce an average output power of as specified. The interstitial catheter is placed proximal (within about 1 cm) to the tumor to be treated using the 14 gauge introducing catheter to avoid tumor seeding. The laser is applied for the specified time, then the fiber repositioned (using a fresh introducer if changing grid coordinates) to illuminate additional areas of the tumor as previously mapped and the laser re-applied. Immediately after the laser illumination of the patient's target lesion, a biopsy that will provide at least 6 mg of tumor tissue (such as an 18 gauge Tru-Cut needle biopsy 1 cm in length or similar technique) is performed to measure the gold accumulation by neutron activation analysis. If more than one tumor is being treated in a single patient, biopsies need only be obtained for the odd-numbered lesions (1st, 3rd, 5th, etc.).

Endpoints

For each patient, up to five (5) index lesions are identified. Index lesions are those that are accessible to direct examination (examination by fiberoptic nasopharyngoscopy or laryngoscopy is permitted) and to biopsy. Each index lesion should have at least one dimension with longest diameter ≥15 mm using conventional techniques or ≥10 mm with spiral CT scan, and also be able to provide at least 6 mg of tumor tissue by biopsy (such as an 18 gauge Tru-Cut needle biopsy 1 cm in length or similar technique) for assessment by neutron activation analysis. Tumor measurements are assessed from physical measurements and imaging techniques as appropriate for the lesion(s), e.g. CT, MRI, X-rays. Baseline measurements should be performed as close to AuroLase treatment as possible. All measurable lesions up to a maximum of five lesions are identified as target lesions and recorded and measured at baseline. Target lesions are selected on the basis of their size (lesions with the longest diameter) and their suitability for accurate repeated measurements (either by imaging techniques or clinically). A sum of the longest diameter (LD) for all target lesions will be calculated and reported as the baseline sum LD. The baseline sum LD will be used as reference by which to characterize the objective tumor.

All other lesions (or sites of disease) are identified as non-target lesions and should also be recorded at baseline. Measurements of these lesions are not required, but the presence or absence of each should be noted throughout follow-up.

Results

The patients have an 60-80 percent reduction of tumor size 6 months after therapy. In 15% of the patients, the cancer is completely eradicated. In 40% of the patients, no side effects are noted and normal prostate function is maintained.

Example 4

The following study describes results achieved using nanoparticles (Auroshells) with an embodiment of a laser catheter assembly as described elsewhere herein.

A completed Pilot Study of AuroLase Therapy (e.g., the use of nanoparticles and irradiation with a laser catheter assembly as described elsewhere herein) in 11 human subjects with head and neck cancer under a cleared FDA IDE revealed no safety-related issues in either particle delivery or the laser procedure.

Similarly, a pilot study of AuroLase Therapy in 22 human subjects with biopsy-diagnosed prostate cancer resulted in no Serious Adverse Events in either particle delivery or the laser procedure. In total, as of the current study, 33 human subjects have undergone AuroShell® particle infusion and 26 have additionally undergone the related laser therapy with no reported Serious Adverse Events.

Preclinical safety has been established for AuroShell® particles in vitro and in vivo in animal testing. Proof of concept studies have been carried out using particles systemically directed against inoculated tumors in the brain, directly injected into canine prostate and in human prostate tumors grown orthotopically in mice.

With the basics of animal and human safety established, the focus of the current study was to determine the efficacy of treatment with nanoshells and subablative infrared irradiation of those nanoshells using a laser catheter as disclosed herein. The treatment was performed on patients suffering from prostate disease in a 22 patient pilot study. All 22 patients were infused with nanoshells at 3 different dosing levels. Fifteen of these patients subsequently had the laser procedure as well. In a different study a further 13 patients were infused with nanoshells and subsequently underwent an ultrasound-guided focal laser ablation of tumor tissue.

While this study was conceived and organized as a safety trial, a number of whole-mount prostate sections of varying quality were available for histopathological analysis. From these analyses it was possible to draw additional conclusions about treatment efficacy.

The prostate study was carried out under the auspices of the Mexican health safety commission, COFEPRIS, as an open-label, multi-center, single-dose pilot study of AuroLase Therapy in the treatment of subjects with primary resectable prostate cancer. Only subjects that were scheduled for a radical prostatectomy were enrolled. The trial was divided into two arms: 1) Group 1 whose patients were infused with AuroShell particles one (1) day prior to a scheduled radical prostatectomy, and 2) Group 2 whose patients were given an infusion of AuroShell Particles one (1) day prior to a laser treatment, and 5±1 days prior to a scheduled radical prostatectomy. Patients were followed for 6 months following particle infusion with regular checks of vital signs, hematology, blood chemistry, and urinalysis. In total, seven (7) subjects completed the study in Group 1 and fifteen (15) subjects completed the study in Group 2.

Prostate Results

Between January 2011 and July 2012 we enrolled 22 prostate cancer patients in México. Each of these patients was infused with clinical AuroShell particles (nanoshells as disclosed elsewhere herein), and 15 of these underwent AuroLase Therapy laser treatment. Apart from the safety results, two general conclusions were made based on the results: 1) over a narrow range of power settings, laser energy goes from producing no observable thermal damage to producing thermal lesions up to 1 cm across, and 2) Nuclear Activation Analysis (NAA) indicates there is enhanced AuroShell particle accumulation in prostatic adenocarcinoma as opposed to normal prostatic tissue.

Adverse Events

Only two Adverse Events were attributed to the infusion element of AuroLase Therapy: a patient who suffered an apparent allergic reaction at the time of infusion, which resolved with intravenous medication, and a patient who suffered a single episode of a burning sensation of the epigastrium, for which no treatment was given, and which resolved spontaneously. No Adverse Events were attributed to the laser treatment.

Infusion and Laser Dose

All patients were infused with the same 7.5 mL/kg (100 OD) dose of particles. This scales the particle dose by weight, and hence by blood volume. Fifteen (15) subjects in Group 2 received a laser treatment on the day following infusion. A trans-rectal ultrasound probe was used to direct a single placement of the optical fiber system within the cortex of each hemisphere of the prostate. Adjustment of the position of the optical fiber catheter within each hemisphere was based on the location of the highest Gleason score indicated by the needle biopsy. The goal of the laser treatment was to demonstrate the safety of the procedure by developing a laser dose that was ablative of tumor tissue, but not of healthy gland. Though this was a safety study, insights into efficacy by varying the laser dose beginning at 3.0 W-3.5 W delivered for 3 min at each site based on the optimal laser dose was established. In total, 6 patients were treated at 3.5 W or below. Over the course of the fifteen laser-treated patients this dose was increased incrementally to 5.0 W (3 patients) delivered for 3 min, and then reduced to 4.5 W delivered for either 3 or 4 min at each treatment site (6 patients).

Limitations of the Mexico Study and Interpretation of Results

Although quite satisfactory as an evaluation of safety, the Mexico prostate study was limited in its ability to determine treatment efficacy in the following ways:

1) The standard 12-punch biopsy used to diagnose and stage patients for the trial did not provide accurate mapping of the number, extent, or specific location of patient tumor(s),
2) The small, portable ultrasound system available, while sensitive enough to insert the laser catheter into the general area of a particular prostate hemisphere, did not provide the millimeter scale resolution for reliably placing the laser catheter within or adjacent to a tumor, which was in any event invisible to the ultrasound system,
3) The logistics of fixing, cutting, embedding, transporting, assessing, and reporting on a given case rarely provided information timely enough to adjust treatment parameters prior to a subsequent case, and
4) The private clinic where the research was performed was able to provide whole mount slides for discrete, but incomplete sections of the laser-treated prostates.

FIGS. 14A-14I show representative whole-mount sections from the last 9 of the 15 laser-treated patients (those treated at >3.5 W; scale bars=1 cm). These H&E sections (Hematoxylin and Eosin) show the spatial relationship between the tumor tissue present 1001 and the optical fiber placement 1002 in the prostate 1000, and any resulting zones of coagulo-necrosis 1003. For patients 208 and 210-215 at least one laser fiber placement was within or adjacent to regions of tumor. It is generally the case that treatments at the 4.5 W level produced coagulo-necrosis conformal to tumor boundaries, but generally not in normal gland, while treatments at the 5.0 W level tended to produce thermal lesions generally. It is further noted that in no case was the prostate capsule breached by the coagulo-necrotic zones.

Figure 14A:
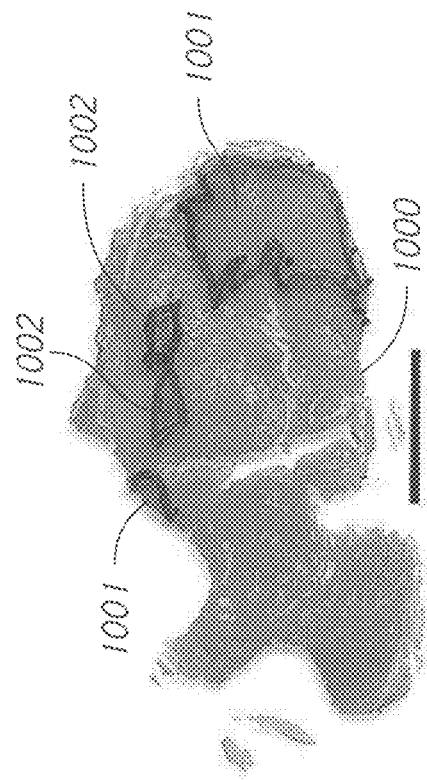
Figure 14B:
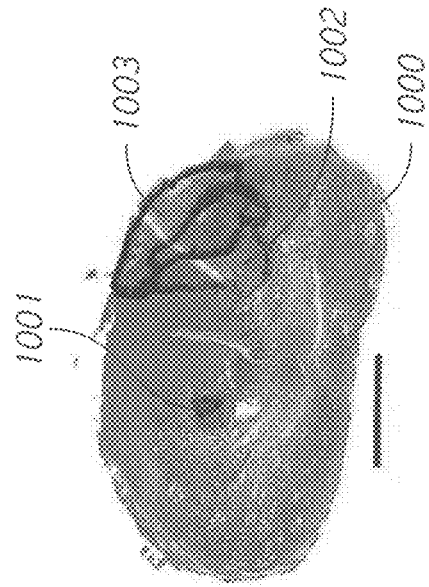
Figure 14C:
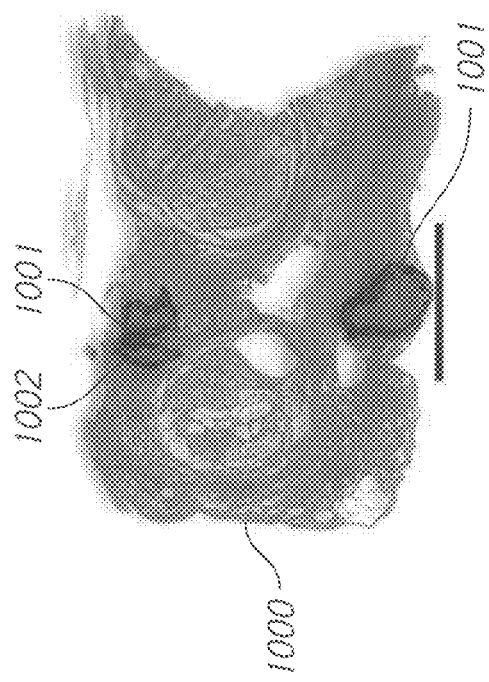
Figure 14D:

FIG. 14A shows 4.4 W irradiation for 3 min and no damage in normal gland. FIG. 14B shows 4.4 W irradiation for 3 min with no damage in normal gland. FIG. 14C shows 5.0 W irradiation for 3 min with non-specific damage in normal gland. FIG. 14D shows 5.0 W irradiation for 3 min with no damage to normal gland and non-specific damage at periphery of carcinoma. FIG. 14E shows 4.5 W irradiation for 4 min and a damage zone conformal to tumor boundary (1003) with no damage at a secondary site (1002). FIG. 14F shows 4.5 W irradiation for 4 min with no damage in normal gland and no damage at periphery of carcinoma. FIG. 14G shows 4.5 W irradiation for 3 min with a thermal lesion that overlaps carcinoma and normal tissue, a thermal lesion in the normal gland enhanced by hemorrhage (upper left region, 1003). FIG. 14H shows 4.5 W irradiation for 3 min with thermal damage in normal hemorrhagic gland. FIG. 14I shows 5 W irradiation for 3 minutes with thermal damage in the normal hemorrhagic gland (arrow to region, 1003).

Figure 15:
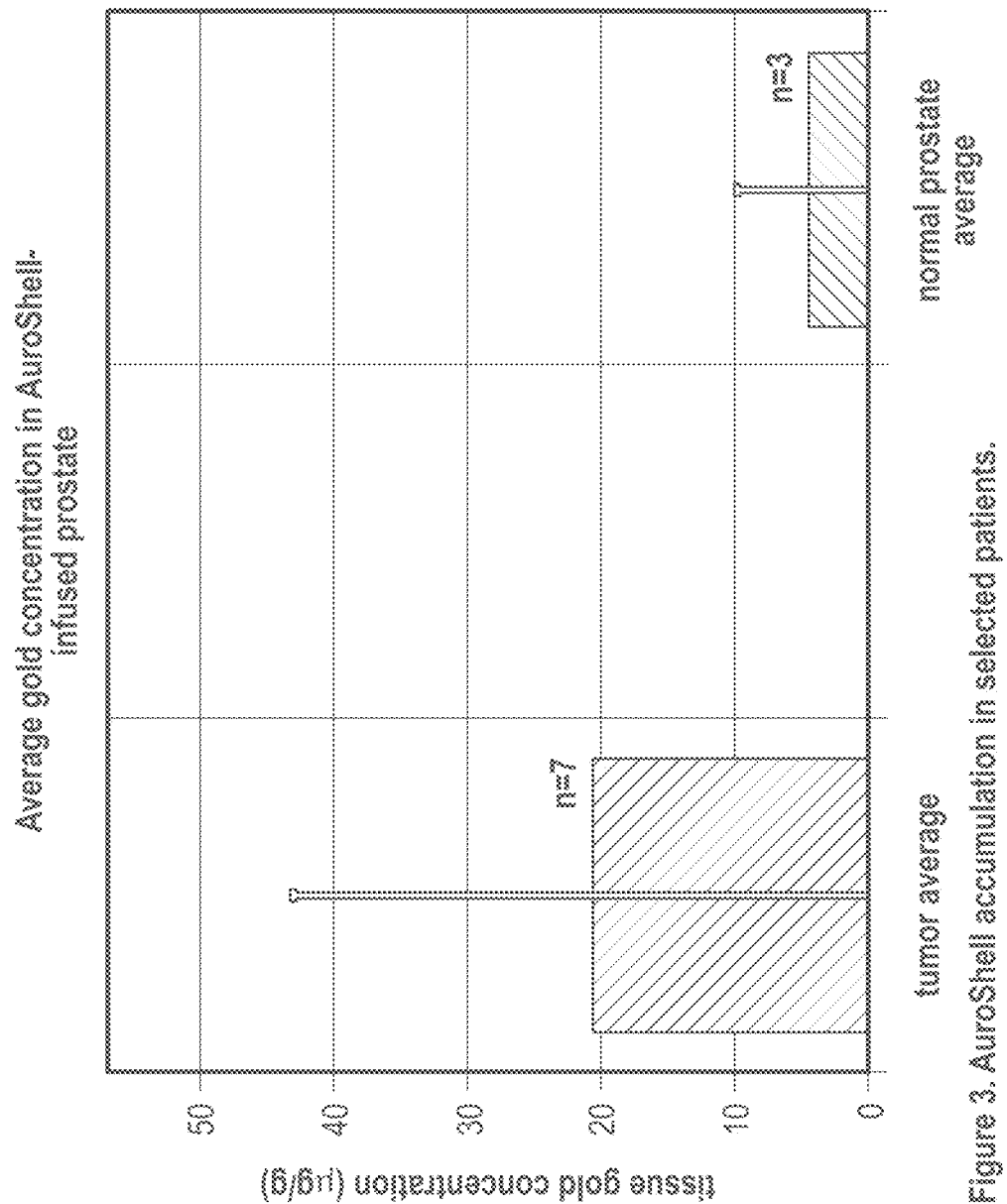
FIG. 15 is a graph showing the relative accumulation of nanoparticles in samples tumor tissue versus healthy tissue from two patients.

FIG. 15 shows the relative accumulation of AuroShell particles in representative samples taken from patients 210 and 211 (see FIGS. 14D and 14E) as determined by NAA. Although the selected samples vary considerably as does the tumor grade as determined from the Gleason score, there is clearly a distinctly greater accumulation of particles in tumor tissue.

Concept for Demonstrating Treatment Efficacy

The optical properties of tissues limit the depth of propagation of optical energy, thereby enabling a truly focal therapy. Heat evolved from an energy source is inherently diffuse and nonspecific. Although thermally ablative heat can be made to propagate on the millimeter scale, it is not specific to tumor conformation. AuroShell particles offer the opportunity for more precisely localized conformal therapy and result in tumor specific damage on the millimeter scale. The MRI fusion imaging approach, using ultrasound guidance based on a priori MRI fusion imaging, should permit the precise placement of the optical fiber catheter within or adjacent to the index prostate lesion targeted for ablation.

Details for Demonstrating Treatment Efficacy

Particle-directed treatment can be made very focal. Over a narrow range of laser power settings, 4.0-5.0 W/cm, photothermal treatments can be made to spare normal glandular tissue and thermally ablate particle-containing adenocarcinoma and BPH.

As a result of the enhanced optical absorption resulting from the presence of particles, AuroLase Therapy is able to generate photothermal lesions by elevating target tissues to 55-65° C. over the course of a 3-4 minute treatment time. These temperature profiles generate coagulo-necrotic regions, which re-granulate and dissolve over the course of days, as opposed to thermally fixed lesions that tend not to resolve, while additionally appearing live on most histopathological examinations. Results of photothermal ablation are fully realized within 48-72 hours post treatment and are observable under MRI.

Since the accumulation of particles is a function of neovasculature and not cell surface biomarkers of vessel and cell walls, AuroLase Therapy can be performed soon after (or prior to) chemotherapy and radiation therapy. There is, as yet, no evidence that AuroLase Therapy efficacy is affected by previous therapies.

Summary

Questions of safety have been answered both in terms of particle safety and laser delivery.

A merging of MRI fusion imaging and the subsequent directed placement of the laser catheter represents a means of establishing the efficacy and utility of AuroLase Therapy for the treatment of localized prostate disease, and represents the logical next step in the utilization of AuroLase Therapy. The MRI-Ultrasound fusion approach is useful for resolving limitations identified in previous studies of AuroLase Therapy given the ability to do: 1) pre-treatment target planning, and 2) guided imagery for the accurate placement of the laser catheter in proximity to the index lesion to be ablated.

Three-dimensional localization of the optical fiber catheter within the prostate, coupled with near real-time thermal data (ideally MRTI) would permit the appropriate treatment power to be confirmed and the treatment time to be either lengthened or shortened in order to produce focal ablation that conforms to the index lesion to be treated.

Testing in squamous cell carcinomas of the head and neck, canine melanomas and carcinomas of the oral cavity, and in canine and human prostate all demonstrate the focal nature of particle-directed photothermal energy. Incorporation of an imaging modality can enable precise lesion treatment. Further, the ability of particles to co-locate to neoplastic tissue can further enable lesion ablation conformal to the target tumors.

The potential benefits of AuroLase Therapy comprise a highly selective and rapid tumor destruction with minimal damage to surrounding tissue enabling a potentially curative treatment of tumors with minimum toxicity. Preclinical studies have demonstrated that AuroLase therapy is effective and causes no detectable systemic toxicity.

In summary, various embodiments and examples of methods, systems, and devices for treating tumors have been disclosed. Although the methods, systems, and devices have been disclosed in the context of those embodiments and examples, it will be understood by those skilled in the art that this disclosure extends beyond the specifically disclosed embodiments to other alternative embodiments and/or other uses of the embodiments, as well as to certain modifications and equivalents thereof. For example, some embodiments of the method are configured to be also used with other types of devices and systems. This disclosure also expressly contemplates that various features and aspects of the disclosed embodiments can be combined with, or substituted for, one another. Accordingly, the scope of this disclosure should not be limited by the particular disclosed embodiments described above, but should be determined only by a fair reading of the claims that follow or that may be presented in the future.

What is claimed is:

1. A method of treating a tumor, the method comprising:
infusing nanoparticles into a patient systemically wherein the nanoparticles are adapted to transduce infrared light into heat energy;
allowing the nanoparticles to preferentially accumulate in the tumor;
inserting a trocar assembly comprising a trocar and a catheter sheathed around the trocar into the patient at a first insertion point;
positioning the trocar assembly in the patient by passing the trocar assembly through the tumor such that the trocar assembly terminates at a distal side of the tumor creating a first path within the tumor;
removing the trocar from the patient and leaving the catheter in the patient within the first path;
inserting an introducer probe of a laser illuminator assembly into the catheter wherein the laser illuminator assembly comprises:
the introducer probe, the introducer probe being elongate and comprising a first lumen and terminating in a sealed domed end configured to allow laser light transmission;
an internal tube located within the first lumen of the introducer probe, the internal tube comprising a second lumen;
an optical fiber configured to receive photons from a laser source, wherein the optical fiber is positioned within the second lumen of the introducer probe and is configured to transmit laser radiation through the domed end of the introducer probe;
wherein the first lumen is in fluidic communication with the second lumen; and
wherein the domed end is configured to allow laser light transmission and to dissipate heat caused by electromagnetic radiation from the laser source to reduce incidences of melting of the introducer probe;
guiding the introducer probe to a first position within the first path in the tumor, wherein the first position is located at or near the distal side of the tumor; and
activating the laser source when the introducer probe is at the first position within the first path to generate non-ablative infrared radiation at the first position for a first period of time;
wherein the infrared radiation causes heating of the nanoparticles to an ablative temperature.

2. The method of claim 1, wherein the tumor is a prostate tumor.

3. The method of claim 1, further comprising withdrawing the catheter and the introducer probe to a second position within the first path in the tumor, the second position being proximally located relative to the first position; and
activating the laser source when the introducer probe is at the second position to generate non-ablative infrared radiation for a second period of time wherein the infrared radiation causes heating of the nanoparticles to an ablative temperature.

4. The method of claim 3, wherein the first position and the second position of the first path are about 8 mm apart.

5. The method of claim 1, further comprising removing the catheter and the laser illuminator from the first path;
inserting the trocar assembly into the patient at a second insertion point that is laterally disposed on the proximal side of the tumor from the first insertion point;
positioning the trocar assembly in the patient by passing the trocar assembly through the tumor such that the trocar assembly passes through the proximal face of the tumor and terminates at the distal side of the tumor and creates a second path through the tumor;
removing the trocar from the catheter;
inserting the introducer probe into the catheter;
guiding the introducer probe to a first position within the second path in the tumor, wherein the first position is located near the distal side of the tumor;
activating the laser source when the introducer probe is at the first position within the second path to generate non-ablative infrared radiation at the first position of the second path for a second period of time wherein the infrared radiation causes heating of the nanoparticles to an ablative temperature.

6. The method of claim 5, further comprising withdrawing the catheter and the introducer probe to a second position within the second path in the tumor, the second position being proximally located relative to the first position in the second path; and
activating the laser source when the introducer probe is at the second position of the second path to generate non-ablative infrared radiation for a third period of time wherein the infrared radiation causes heating of the nanoparticles to an ablative temperature.

7. The method of claim 6, wherein the first position and the second position of the second path are about 8 mm apart.

8. The method of claim 5, wherein a template grid is used to position the trocar assembly at the first insertion point and at the second insertion point.

9. The method of claim 5, further comprising inserting the trocar assembly into the patient at additional insertion points that are laterally disposed on the proximal side of the tumor from the first insertion point and second insertion points.

10. The method of claim 9, wherein a template grid is used to position the trocar assembly at the additional insertion points.

11. The method of claim 1, wherein the laser illuminator assembly comprises a coolant outlet in fluidic communication the first lumen and a coolant inlet in fluidic communication with the second lumen wherein the laser illuminator assembly is configured to allow the passage of a coolant from the coolant inlet through the second lumen into the first lumen and out of the coolant outlet.

12. The method of claim 1, wherein the laser illuminator is activated by an actuator that is controlled by a user.

13. The method of claim 12, wherein when the user activates the laser illuminator using the actuator, coolant flows into the first inlet of the laser illuminator assembly and wherein when the laser illuminator is not active, coolant does not flow laser illuminator assembly.

14. The method of claim 13, wherein the actuator is a foot pedal.

15. The method of claim 1, wherein the laser illuminator emits radiation having a near infrared wavelength.

16. The method of claim 1, wherein the laser illuminator emits radiation having a near infrared wavelength ranging from about 805 nm to about 810 nm.

17. The method of claim 1, wherein the laser illuminator emits radiation that is of insufficient power to induce photothermal coagulation of tissue.

18. The method of claim 1, wherein the optical fiber comprises a diffuser tip that distributes the non-ablative infrared radiation within the tumor.

19. A method of treating a prostate tumor, the method comprising:
infusing nanoparticles into a patient systemically wherein the nanoparticles are adapted to transduce infrared light into heat energy;
allowing the nanoparticles to preferentially accumulate in the prostate tumor;
inserting a trocar assembly comprising a trocar and a catheter sheathed around the trocar into the patient at a first insertion point;
positioning the trocar assembly in the patient by passing the trocar assembly through the prostate tumor such that the trocar assembly terminates at a distal side of the prostate tumor creating a first path within the prostate tumor;
removing the trocar from the patient and leaving the catheter in the patient within the first path;
inserting an introducer probe of a laser illuminator assembly into the catheter wherein the laser illuminator assembly comprises:
the introducer probe, the introducer probe being elongate and comprising a first lumen and terminating in a sealed domed end configured to allow laser light transmission;
an internal tube located within the first lumen of the introducer probe, the internal tube comprising a second lumen; and
an optical fiber configured to receive photons from a laser source, wherein the optical fiber is positioned within the second lumen of the introducer probe and is configured to transmit laser radiation through the domed end of the introducer probe;
wherein the first lumen is in fluidic communication with the second lumen; and
wherein the domed end is configured to allow laser light transmission and to dissipate heat caused by electromagnetic radiation from the laser source to reduce incidences of melting of the introducer probe;
guiding the introducer probe to a first position within the first path in the prostate tumor, wherein the first position is located at or near the distal side of the prostate tumor;
activating the laser source when the introducer probe is at the first position within the first path to generate non-ablative infrared radiation at the first position for a first period of time wherein the infrared radiation causes heating of the nanoparticles to an ablative temperature;
withdrawing the catheter and the introducer probe to a second position within the first path in the prostate tumor, the second position being proximally located relative to the first position; and
activating the laser source when the introducer probe is at the second position to generate non-ablative infrared radiation for a second period of time wherein the infrared radiation causes heating of the nanoparticles to an ablative temperature.

20. A method of treating a tumor, the method comprising:
obtaining a laser illuminator assembly, the laser illuminator assembly comprising:
an introducer probe, the introducer probe being elongate and comprising a first lumen and terminating in a sealed domed end configured to allow laser light transmission;
an internal tube located within the first lumen of the introducer probe, the internal tube comprising a second lumen; and
an optical fiber configured to receive photons from a laser source, wherein the optical fiber is positioned within the second lumen of the introducer probe and is configured to transmit laser radiation through the domed end of the introducer probe;
wherein the first lumen is in fluidic communication with the second lumen; and
wherein the domed end is configured to allow laser light transmission and to dissipate heat caused by electromagnetic radiation from the laser source to reduce incidences of melting of the introducer probe;
positioning the introducer probe in a tissue comprising the tumor by passing the introducer probe through a proximal face of the tissue to a distal side of the tissue to a first position; and activating the laser source while the introducer probe is at the first position to transmit sub-ablative infrared radiation to the tissue for a first period of time.

\* \* \* \* \*